United States Patent
Basu et al.

(10) Patent No.: US 8,247,551 B2
(45) Date of Patent: *Aug. 21, 2012

(54) LEAD SENSOR AND METHODS OF USE

(75) Inventors: Partha Basu, Pittsburgh, PA (US);
Barbara Serli Mitasev, Melrose, MA (US); Lauren E. Marbella, Pittsburgh, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 347 days.

This patent is subject to a terminal disclaimer.

(21) Appl. No.: 12/583,294

(22) Filed: Aug. 18, 2009

(65) Prior Publication Data

US 2010/0041158 A1 Feb. 18, 2010

Related U.S. Application Data

(63) Continuation-in-part of application No. 12/020,343, filed on Jan. 25, 2008, now Pat. No. 7,888,506.

(60) Provisional application No. 60/897,576, filed on Jan. 26, 2007, provisional application No. 61/189,317, filed on Aug. 18, 2008.

(51) Int. Cl.
*C07D 241/36* (2006.01)
*G01N 21/76* (2006.01)
*G01J 3/30* (2006.01)

(52) U.S. Cl. ........... 544/343; 349/70; 356/317; 436/172

(58) Field of Classification Search ..................... None
See application file for complete search history.

(56) References Cited

OTHER PUBLICATIONS

Bradshaw et al., "Stable pyrano[2,3-b] quinoxalines and pyrano[2,3-g] pteridines related to molybdopterin", Chemistry Communications, (2001) pp. 123-124 (Bradshaw).*

* cited by examiner

*Primary Examiner* — Krishnan S Menon
*Assistant Examiner* — Dirk Bass
(74) *Attorney, Agent, or Firm* — K&L Gates LLP

(57) ABSTRACT

A fluorophore that forms a complex with Pb ions is disclosed. The fluorophore/lead complex fluoresces with an intensity greater than complexes formed by the fluorophore with other metals. The fluorophore may be used as a sensor/detector for lead ions in various samples. Methods for detecting and calculating the concentration of lead ions in samples are also disclosed.

19 Claims, 50 Drawing Sheets

Figure 2. Synthetic scheme for the preparation of the different components of fluorophores.

Figure 3. Synthetic schemes for generating a wide variety of fluorophores from compound 5. Note that the thiol group in 11 can be further functionalized for cellular application such as to attach an antibody or other recognition motifs.

Figure 4. Synthetic schemes for generating a wide variety of fluorophores from compound 4

Figure 5. Synthetic schemes for generating a wide variety of fluorophores. Similar compounds shown in Figures 3 and 4 have already been prepared and characterized.

Figure 8. Fluorescence spectra of solutions containing metal ion in question, and compound 7 in the presence of NH$_4$OH.

Figure 9. Electronic spectrum of compound 7 in MeOH.

Figure10. Fluorescence spectrum of compound 7 in the mixed solvent described in the text.

Figure 11. Use of the fluorophores in metal binding.

Fig. 22 Compound 7 – 2.5×10⁻⁵ M + NEt₄OH (1:2) in methanol after 17 days $Pb^{2+}$ + other metal = grey
Other metal = black

LEAD SENSOR AND METHODS OF USE

CROSS REFERENCE TO RELATED APPLICATIONS

This application is a Continuation-In-Part of U.S. Application Ser. No. 12/020,343 filed Jan. 25, 2008, now U.S. Pat. No. 7,888,506, issued Feb. 15, 2011, which claims priority to U.S. Provisional Application Ser. No. 60/897,576 filed Jan. 26, 2007; and claims priority thereto under 35 U.S.C. §120 and also claims priority under 35 U.S.C. §119(e) to U.S. Provisional Application Ser. No. 61/189,317 filed Aug. 18, 2008, the disclosures of each of which are incorporated in their entirety by this reference.

GOVERNMENTAL INTEREST

Portions of this invention was made with Government support under grant GM061555 awarded by the National Institutes of Health. The Government may have certain rights in the invention.

FIELD OF THE TECHNOLOGY

The present invention relates to a new fluorophore that forms a complex with lead ions that fluoresces with a greater fluorescence emission intensity than complexes formed between the fluorophore and other metal ions. Detectors and sensors, as well as methods for detecting and quantifying lead ions in a sample are also disclosed.

BACKGROUND

Fluorescent molecules are of great interest because of their potential uses, for example, but not limited to, in labeling and detection of substrates or molecules in cell based assays, as components in organic electronic materials in molecular electronics, as pH sensors, and as metal sensors. There are currently several general classes of fluorescent molecules. These have been divided based on their structural motifs. For example, some common fluorescent structures include xanthene based fluorescein and rhodamine compounds, coumarins, pyrenes, and molecules based on the cyanine dyes. Other common fluorophores include, for example, auramine, acridine orange, dipyrrin, and porphyrin. The basic structures of these common fluorophores are presented in FIG. 1.

Molecular fluorescence is a type of photoilluminescence, which is a chemical phenomenon involving the emission of light from a molecule that has been promoted to an excited state by absorption of electromagnetic radiation. Specifically, fluorescence is a luminescence in which the molecular absorption of a photon triggers the emission of a second photon with a longer wavelength (lower energy) than the absorbed photon. The energy difference between the absorbed photon and the emitted photon results from an internal energy transition of the molecule where the initial excited state (resulting from the energy of the absorbed photon) transitions to a second, lower energy excited state, typically accompanied by dissipation of the energy difference in the form of heat and/or molecular vibration. As the molecule decays from the second excited state to the ground state, a photon of light is emitted from the compound. The emitted photon has an energy equal to the energy difference between the second excited state and the ground state.

Many fluorescent compounds absorb photons having a wavelength in the ultraviolet portion of the electromagnetic spectrum and emit light having a wavelength in the visible portion of the electromagnetic spectrum. However, the absorption characteristics of a fluorophore are dependent on the molecules absorbance curve and Stokes shift (difference in wavelength between the absorbed and emitted photon), and fluorophores may absorb in different portions of the electromagnetic spectrum.

The basic structures of the known fluorophores (FIG. 1) may be modified to provide different excitation and emission profiles. For example, two related compounds, fluorescein and rhodamine have different fluorescent characteristics. Fluorescein absorbs electromagnetic radiation having a wavelength of ~494 nanometers ("nm") and emits light having a wavelength at ~525 nm, in the green region of the visible spectrum, whereas rhodamine B absorbs in radiation having a wavelength of ~510 nm and emits light with an emission maximum of ~570 nm, in the yellow-green region of the visible spectrum. Other fluorophores have different absorption and emission profiles. For example, coumarin-1 absorbs radiation at 360 nm and emits light at ~460 nm (blue light); and pyrene absorbs radiation at ~317 nm and emits light having a wavelength of ~400 nm (violet light).

Exposure to lead is considered by the Center for Disease Control (CDC) as one of the United States' most serious environmental health threats for children. Exposure to lead may lead to damage to neurological, reproductive, and cardiovascular systems in children and adults and leads to other developmental problems. As a result of these concerns, the United States Environmental Protection Agency (EPA) has set a limit for lead in drinking water at 15 parts-per-billion (ppb). It is currently estimated that 1 in 11 children in the United States are at risk of adverse health effects from exposure to lead and that nearly 1.7 million children have lead blood levels of greater than 10 µg/dL.

Current methods for detecting and quantifying levels of lead in samples, such as environmental samples, include atomic absorption spectroscopy, inductively coupled plasma mass spectroscopy ("ICPMS"), and anodic stripping voltammetry which can measure lead at levels of ppb, ppb and parts-per-million (ppm), respectively. However, these methods have certain disadvantages, including being instrumentally intensive, generally expensive, lacking in spatial information, and restricted to in vitro measurements.

Despite their versatility, the known fluorophores have a number of disadvantages. For example, the absorption spectra of the fluoroscein class of fluorophores are generally pH sensitive, such that fluorescent yield decreases rapidly at pH levels below 8. Rhodamine and pyrene based fluorescent dyes are hydrophilic and hydrophobic, respectively.

BRIEF SUMMARY

Various embodiments provide for fluorescent compounds that are capable of detecting the presence of $Pb^{2+}$ in samples. Other embodiments relate to uses of the fluorescent compounds as detectors for $Pb^{2+}$ including detection of lead ions in the presence of other metal ions.

In one embodiment, the present disclosure provides a fluorescent binder for $Pb^{2+}$ ions represented in its protected form by Formula IV:

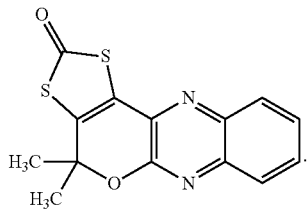

IV

Other embodiments provide for a $Pb^{2+}$ sensor comprising a matrix material and a fluorophore represented in its protected form by Formula IV, wherein the fluorophore is dissolved in, embedded in, affixed in, absorbed in, or suspended in the matrix material and forms a fluorescent complex when bound in its unprotected form to $Pb^{2+}$.

Further embodiments provide for a method for detecting Pb comprising contacting a $Pb^{2+}$ sensor comprising a fluorophore represented in its protected form by Formula IV, with a composition, wherein $Pb^{2+}$ in the composition binds with the fluorophore in its unprotected form to form a complex, and measuring a fluorescence emission intensity of the complex. The method may further comprise exciting the complex by irradiating the complex with a light source and/or calculating the concentration of $Pb^{2+}$ ions in the composition based on the fluorescence emission intensity of the complex.

BRIEF DESCRIPTION OF THE DRAWINGS

The various embodiments of the present disclosure will be better understood when read with reference to the following figures.

DETAILED DESCRIPTION

Figure 1:
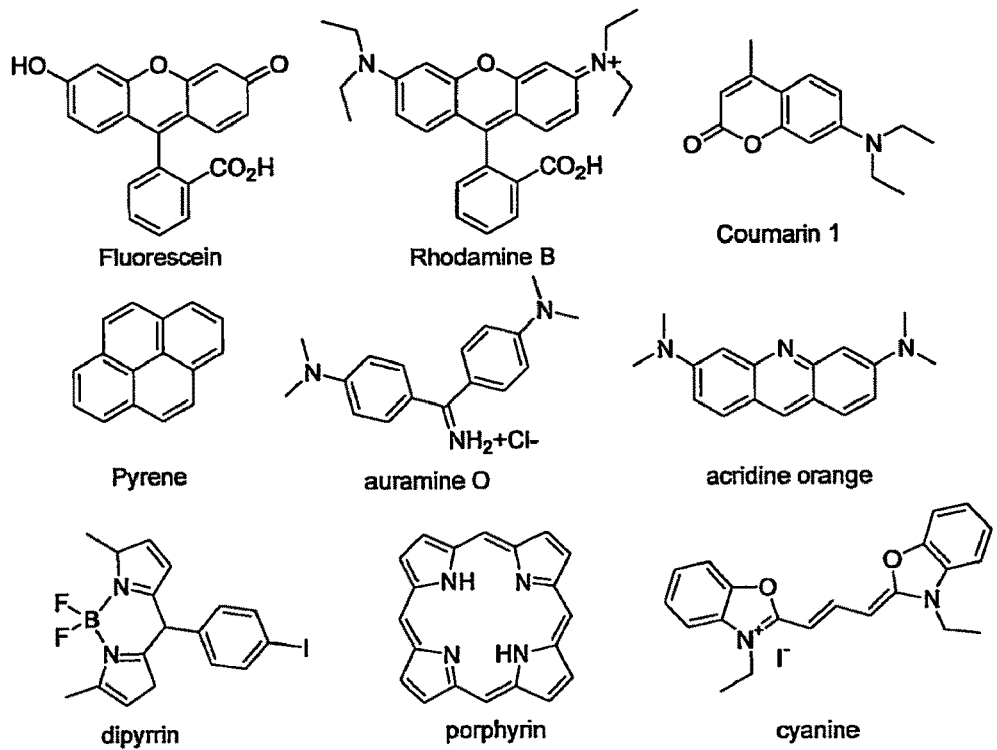
FIG. 1 illustrates various fluorescent molecules known in the prior art.

The present disclosure relates to a new class of fluorophores that may be synthesized from readily available materials. The structure of the fluorophore is designed with the flexibility to have multiple substitution patterns. Various uses of the fluorophores, including for example, as molecular markers, pH sensors, organic electric materials in molecular electronics, and metal binders/sensors, are also disclosed. Particular embodiments include a fluorescent binder for $Pb^{2+}$, a fluorophore that can detect $Pb^{2+}$ ions in the presence of other metal ions in a sample and methods for detecting and quantifying $Pb^{2+}$ ions in a sample.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

The present disclosure relates to the development of a new class of fluorophores having a structure comprising at least three fused rings including a five membered ring containing an ene-dithiolate moiety, a six-membered pyran ring, and a six-membered pyrazine ring. The general structure of the new class of fluorophores is represented by Formula I.

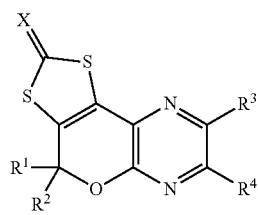

I

In Formula I, X represents a group such as O (i.e., a carbonyl, a "dithiolone"), S (i.e., a thiocarbonyl), Se (i.e., a selenocarbonyl), $NR^x$ (i.e., an imine), $NR^x_2{}^+$ (an iminium ion), or $NNHR^x$ (a hydrazine). Each Rx may independently be a group such as hydrogen, the group -L-$R^y$, $C_1$-$C_6$ alkyl, phenyl, and substituted phenyl. The substituted phenyl may have from 1 to 5 substituents where each substituent may independently be one or more of the group -L-$R^y$, a fluoro, chloro, bromo, nitro, cyano, hydroxy, amino, thiol, $C_1$-$C_6$ alkyl, and $C_1$-$C_6$ alkoxy. As used herein, the term "$C_1$-$C_6$ alkyl" means an alkyl substituent having from 1 to 6 carbon atoms arranged either as a linear chain or as a branched chain. As used herein, the term "$C_1$-$C_6$ alkoxy" means an alkoxy substituent having from 1 to 6 carbon atoms arranged either as a linear chain or as a branched chain and attached via an ether linkage.

Further, in Formula I, $R^1$ and $R^2$ may each independently be hydrogen, the group -L-$R^y$, $C_1$-$C_6$ alkyl, amino $C_1$-$C_6$ alkyl, hydroxy $C_1$-$C_6$ alkyl, thio $C_1$-$C_6$ alkyl, carboxyl $C_1$-$C_6$ alkyl, halo $C_1$-$C_6$ alkyl phenyl, substituted phenyl, aryl, substituted aryl, heteroaryl, or substituted heteroaryl. The substituted phenyl, aryl, or heteroaryl may have from 1 to 5 substituents where each substituent may be one or more of fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxyl $C_1$-$C_6$ alkyl, halo $C_1$-$C_6$ alkyl, and $C_1$-$C_6$ alkoxy. As used herein, the terms "aryl" or "aryl ring" include an aromatic ring (i.e., a single aromatic ring) or ring system (i.e., a polycyclic aromatic ring system) in which all ring atoms are carbon. As used herein, the terms "heteroaryl" or "heteroaryl ring" include an aromatic ring (i.e., a single aromatic ring) or ring system (i.e., a polycyclic aromatic ring system) in which at least one of the ring atoms is a heteroatom, such as nitrogen, oxygen or sulfur heteroatom.

In Formula I, $R^3$ and $R^4$ may independently be the group -L-$R^y$, hydrogen, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, phenyl, substituted phenyl, aryl, substituted aryl, heteroaryl, or substituted heteroaryl. The substituted phenyl, aryl, or heteroaryl may have from 1 to 5 substituents where each substituent may be one or more of a fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, and $C_1$-$C_6$ alkoxy. Alternatively in certain embodiments, $R^3$ and $R^4$ may come together to form one of a benzo ring, a substituted benzo ring, an aryl ring, a substituted aryl ring, a heteroaryl ring, or a substituted heteroaryl ring. The substituted benzo, substituted aryl, or substituted heteroaryl ring(s) may have from 1 to 4 substituents where each substituent may be one or more of the group -L-$R^y$, a fluoro, chloro, bromo, nitro, cyano, hydroxy, amino, thiol, $C_1$-$C_6$ alkyl, amino $C_1$-$C_6$ alkyl, hydroxy $C_1$-$C_6$ alkyl, thio $C_1$-$C_6$ alkyl, carboxy $C_1$-$C_6$ alkyl, halo $C_1$-$C_6$ alkyl, and $C_1$-$C_6$ alkoxy.

For example, according to certain embodiments, the fluorophores of the present disclosure may have a structure as represented by Formula II.

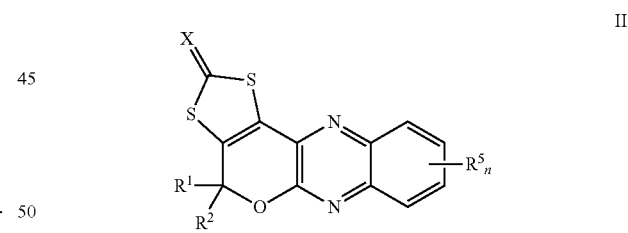

II wherein X, $R^1$ and $R^2$ are as set forth above and $R^3$ and $R^4$ come together to form a benzo ring or substituted benzo ring, wherein n is an integer from 0 to 4 and each $R^5$ is independently a substituent such as, for example, the group -L-$R^y$, fluoro, chloro, bromo, nitro, cyano, hydroxy, amino, thiol, $C_1$-$C_6$ alkyl, hydroxy $C_1$-$C_6$ alkyl, amino $C_1$-$C_6$ alkyl, thio $C_1$-$C_6$ alkyl, carboxyl $C_1$-$C_6$ alkyl, halo $C_1$-$C_6$ alkyl, or $C_1$-$C_6$ alkoxy, or two or more $R^5$ groups come together to form at least one other aromatic ring or heteroaromatic ring (i.e., a aryl ring or heteroaryl ring, respectively).

According to other embodiments, $R^3$ and $R^4$ may come together to form a heteroaryl ring or substituted heteroaryl ring, such as a nitrogen containing heteroaromatic ring as shown in Formula III. As shown in Formula III, each Y in the ring may be either a N or a C, provided that at least one Y is N.

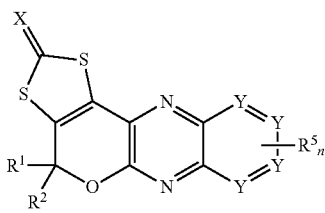

III

Examples of heteroaryl and substituted heteroaryl rings include, but are not limited to, for example, pyridyl, pyrimidyl, pyrazyl, pyridazyl, uracil, thiouracil (2-thiouracil or 4-thiouracil), pyrimidonyl, and the like. With reference to Formula III, the groups X, $R^1$, $R^2$, and $R^5$ may be as described herein and integer n may range from 0 to 3. As will be understood by one having ordinary skill in the art with reference to the synthetic procedures set forth herein, a wide variety of aryl, substituted aryl, heteroaryl and substituted heteroaryl ring structures may be fused to the pyrazine ring of Formula I.

According to the various embodiments, the fluorophores of the present disclosure exhibit fluorescence, for example, when bound to certain metal ions, such as, those metal ions described herein. That is, the fluorophores of the present disclosure absorb electromagnetic radiation. Upon absorption of the electromagnetic radiation, the frontier electron (for single electron excitation) of the fluorophores is promoted to an excited electronic state which then decays to a second excited electronic state concomitant with molecular vibration and/or the release of heat. The fluorophores decay from the second excited state to the ground electronic state with the emission of electromagnetic radiation, wherein the emitted electromagnetic radiation has a wavelength that is longer than the wavelength of the absorbed radiation. For example, certain embodiments of the fluorophores having the structures set forth herein may absorb electromagnetic radiation having a wavelength within the ultraviolet region of the electromagnetic spectrum and fluoresce, that is emit electromagnetic radiation, at a wavelength within the blue light region of the visible spectrum. In certain embodiments, the fluorophores of the present disclosure may fluoresce with an emission maximum at a wavelength within the ultraviolet or visible regions of the electromagnetic spectrum. According to certain embodiments, the fluorophores of the present disclosure may fluoresce with an emission maximum at a wavelength from 200 nm to 850 nm. According to other embodiments, the emission maximum may be at a wavelength from 300 nm to 600 nm. According to other embodiments, the emission maximum may be at a wavelength from 400 rum to 500 nm. As used herein, the term "emission maximum" means the wavelength of the greatest intensity within the fluorescence spectrum of a fluorophore.

Without intending to be limited by any theory or interpretation, it is believed by the inventors that the fluorescent character of the core structure of the fluorophores disclosed herein may depend on and may be manipulated by changing the nature of the conjugated pi system of the fluorophore, the atoms present in the fluorophore, and/or the substituents attached to the fluorophore. As used herein, the term "fluorescent character" includes such characteristics of the fluorophore, such as, but not limited to, the wavelength of light absorbed, the wavelength of the fluorescence emission, the fluorescence emission intensity, and the quantum yield. Thus, the fluorescent character of the fluorophores of the present disclosure may be affected by changing one or more of the nature of the pi system of the fluorophore, the atoms in the fluorophore, or the substitution pattern on the fluorophore.

Changes in the conjugated pi system of the fluorophore having Formula I may be affected, for example, by extending the conjugated pi system of the fluorophore, such as by fusing a benzo group (substituted or unsubstituted), an aryl group (substituted or unsubstituted), or a heteroaryl group (substituted or unsubstituted) to the pyrazine ring of the fluorophore (for example, but not limited to, as set forth in Formula II or III). Alternatively, or additionally, the conjugated pi system of the fluorophore may be extended by attaching a conjugation extending substituent to the pyrazine ring or an aromatic or heteroaromatic ring fused to the pyrazine ring. The aromatic or heteroaromatic ring may be fused directly to the pyrazine ring (that is the rings share two common atoms) or fused indirectly to the pyrazine ring (that is the aromatic or heteroaromatic ring may be fused to an aromatic or heteroaromatic ring that is fused (directly or indirectly) to the pyrazine ring. For example, attaching a substituent, such as an electron withdrawing group or an electron donating group, directly to the pyrazine ring or aromatic ring would alter the electronic nature of the conjugated pi system of the fluorophore. As used herein, the term "electron withdrawing group" means a substituent which withdraws electron density from the fluorophore. As used herein, the term "electron donating group" means a substituent that donates electron density into the fluorophore. Altering the conjugated pi system of the fluorophore, such as, by extending the pi system and/or attaching an electron donating group or electron withdrawing group may change the fluorescent character of the fluorophore, such as, by changing the wavelength of light absorbed and/or emitted or changing the fluorescent quantum yield. As used herein, the term "fluorescence quantum yield" is a measurement of the efficiency of the fluorescence process and is defined by the ratio of the number of photons emitted to the number of photons absorbed by the fluorophore.

Changing the atoms on the fluorophore skeleton may also change the fluorescence characteristics of the fluorophore. For example, and with reference to Formula I, changing the nature of X may affect the fluorescence characteristics of the fluorophore. That is, a fluorophore having Formula I wherein X is O may have a different fluorescence character than a fluorophore having structure I wherein X is S, Se, $NR^x$, $NR^x_2{}^+$, or $NNHR^x$. Thus, each different X group may affect the fluorescence characteristics differently.

In addition, changing the substitution pattern on the fluorophore may also change the fluorescence characteristics of the fluorophore. For example, as set forth herein, attaching a substituent, such as, an electron donating group or an electron withdrawing group may affect the fluorophore and therefore change the fluorescence characteristics of the fluorophore. Alternatively, or in addition, changing the substitution pattern on the fluorophore may also include changing the nature of the substituent $R^1$ and/or $R^2$. For example, changes in the nature of the substituent at $R^1$ and/or $R^2$ may affect the energy of the excited state of the fluorophore, the wavelength of radiation absorbed or emitted, and/or the fluorescent quantum yield. In addition, changing the position of one or more substituent on the ring system of the fluorophore (i.e., changing the ring atom that the one or more substituent is bonded to) may change the fluorescence characteristics of the fluorophore.

According to certain embodiments of the present disclosure, the fluorophores may be used as a molecular probe, such as a biological probe. According to certain embodiments, the fluorophore may be modified with a reactive group that can react with and form a bond to a compound or substrate of interest (i.e., the molecule or substrate to be probed). The product of the chemical reaction between the fluorophore and the compound or substrate of interest will then fluoresce. For example, according to certain embodiments, the fluorophores may contain at least one group -L-$R^y$, wherein $R^y$ is a reactive group that is attached to the fluorophore by a covalent linkage L. Covalent linkage L may be attached to the skeleton of the fluorophore, for example as substituent $R^1$, $R^2$, and/or $R^5$ or any other available covalent attachment site (such as, for example, $R^x$) on the skeleton (as shown in Formulae, I, II, and III). According to certain embodiments, the covalent linkage attaching the fluorophore to $R^y$ may contain multiple intervening atoms that may serve as a spacer, for example an alkylene glycol spacer such as a polyalkylene glycol spacer.

Fluorophores of the present disclosure with one or more reactive groups $R^y$ may label a wide variety of organic or inorganic substances that contain or may be modified to contain functional groups with suitable reactivity to react with reactive group $R^y$. The resulting reaction product may be represented by the formula F-L-Sub, where F represents the fluorophore core, L is the linkage group and Sub indicates the substrate that the fluorophore is now bound to (by the residue of reactive group $R^y$). As used herein, the term "reactive group" means any moiety on the structure L-$R^y$ that is capable of reacting chemically with a functional group on a different compound (i.e., the substrate of interest) to form a covalent or ionic linkage. Examples of suitable reactive groups include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

The covalent linkage L binds the reactive group $R^y$ or the reacted group Sub to the fluorophore, either directly (when L is a single bond) or with a combination of stable chemical bonds, for example, single, double, triple, or aromatic carbon-carbon bonds, carbon-nitrogen bonds, carbon-oxygen bonds, carbon-sulfur bonds, nitrogen-nitrogen bonds, phosphorus-oxygen bonds, phosphorus-nitrogen bonds, and nitrogen-platinum bonds. L may include, for example, ether, alkyl, alkylene glycol, polyalkylene glycol, thioether, carboxamide, sulfonamide, urea, urethane, phosphate ester, and hyrdrazine moieties, including combination of any thereof.

The choice of the reactive group $R^y$, used to attach the fluorophore to the substrate, typically depends on the functionality of the substrate and the type of linkage desired. The types of functionality typically present in organic or inorganic substrates of interest include, but are not limited to, amines, amides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these functionalities. A single type of reactive functionality may be present on a substrate, such as the hydroxyl group on a sugar, or alternatively, multiple different reactive functionality may be present on the substrate (such as with a protein or nucleotide).

According to various embodiments, the fluorophores may be used to bond to or label a variety of organic or inorganic substrates, thereby forming a fluorescent labeled product. For example, according to certain embodiments, the fluorophores may have a reactive group $R^y$ suitable for reacting with a biological monomer or polymer, such as, an amino acid, a peptide, a protein, an enzyme, an enzymatic substrate, an antibody, a nucleic acid base, a nucleoside, an oligonucleotide, or a nucleic acid polymer (single or double stranded). As used herein, the term "enzymatic substrate" includes molecules or compounds capable of binding to an enzyme, for example at the active site of the enzyme or another binding site on the enzyme.

According to certain embodiments, the fluorophore, such as a fluorophore with a reactive group thereon may be reacted with an amino acid or peptide chain to give, respectively, a fluorophore labeled amino acid or peptide chain. The fluorophore labeled amino acid or peptide chain may then be incorporated into a larger peptide or protein chain. In another embodiment, the fluorophore and reactive group thereon may be reacted with a nucleic acid base or nucleoside to give, respectively, a fluorophore labeled nucleic acid base or nucleoside. The fluorophore labeled nucleic acid base or nucleoside may then be incorporated into a larger oligonucleotide or nucleic acid polymer.

For example, according to one embodiment, the fluorophore may be incorporated or bonded to an enzymatic substrate or an antibody to give a fluorescent enzymatic substrate or antibody. The fluorescent enzymatic substrate or antibody may then bind to specific enzymes or antigens, respectively, providing fluorescent labeled enzymes or antigens. In another embodiment, the fluorophore may be incorporated or bonded to a nucleoside which may then be incorporated into a nucleic acid strand to provide a fluorescent labeled nucleic acid.

Various embodiments of the fluorophores disclosed herein may be used according to methods extensively known in the art, such as, use of antibody/protein conjugates in microscopy and immunofluorescent assays or as nucleotide or oligonucleotide conjugates for nucleic acid hybridization assays and nucleic acid sequencing, such as those disclosed in U.S. Pat. Nos. 5,332,666; 5,171,534; 4,997,928; and PCT Published Application WO94/05688, the disclosures of each are hereby incorporated in their entirety by reference.

For example, once a substrate has been labeled by the fluorophore according to various embodiments disclosed herein, the fluorescence emission spectrum of the fluorescent labeled product may be measured. For example, according to certain embodiments, the intensity of the fluorescence emission spectrum may be determined and may be quantitatively correlated to the concentration of labeled product in the composition. In other embodiments, the fluorescence emission spectrum of the fluorescent labeled product may be taken and qualitatively used to determine the presence of labeled product and therefore used to determine the presence of the target molecule (i.e., the substrate) in the composition.

Figure 8:
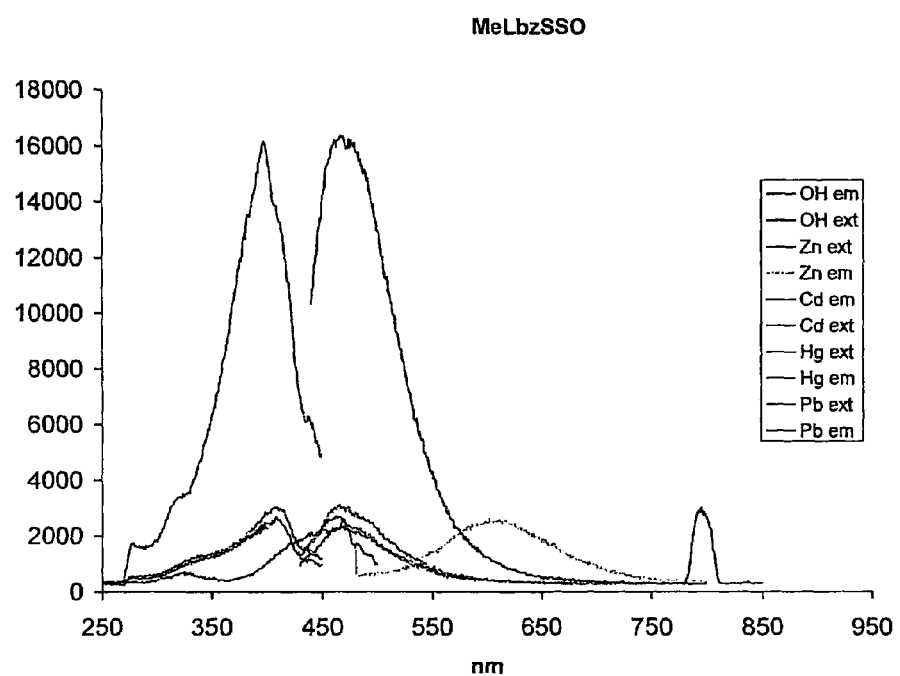
FIG. 8 illustrates the fluorescence emission spectra of metal/fluorophore complexes according to certain embodiments of the present disclosure.
Figure 11:
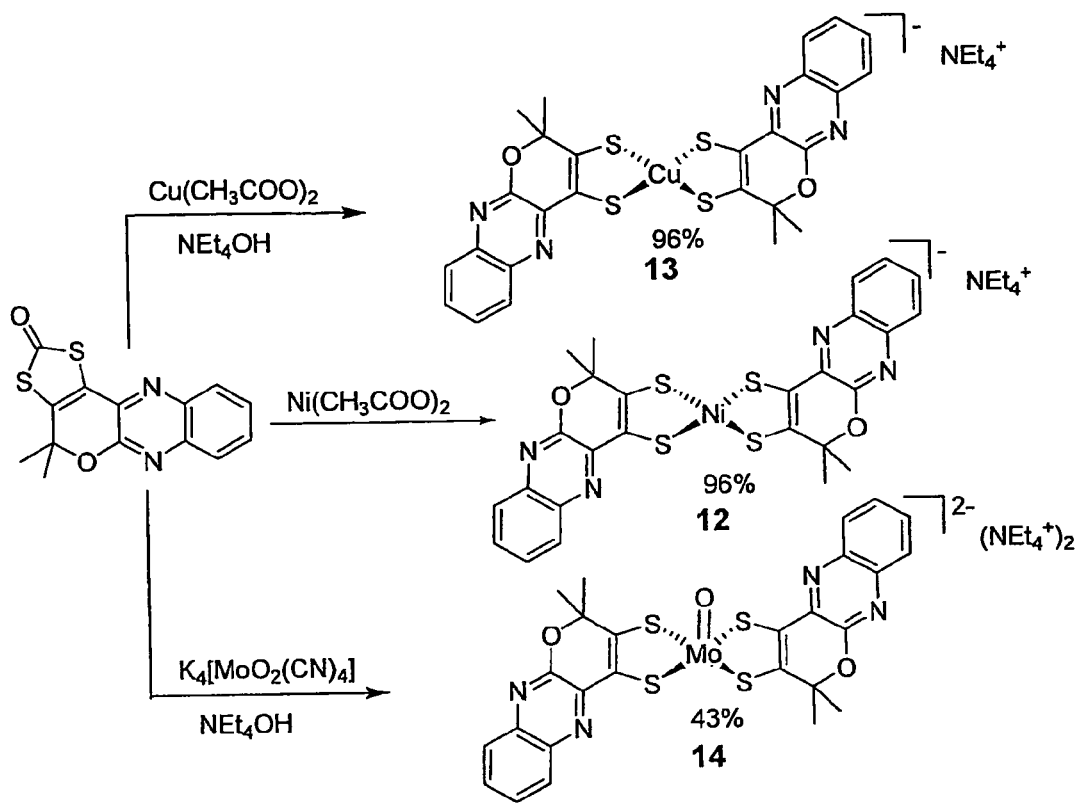
FIG. 11 illustrates the structure of the complexes formed between certain metal ions and a fluorophore according to one embodiment of the present disclosure.
Figure 12:
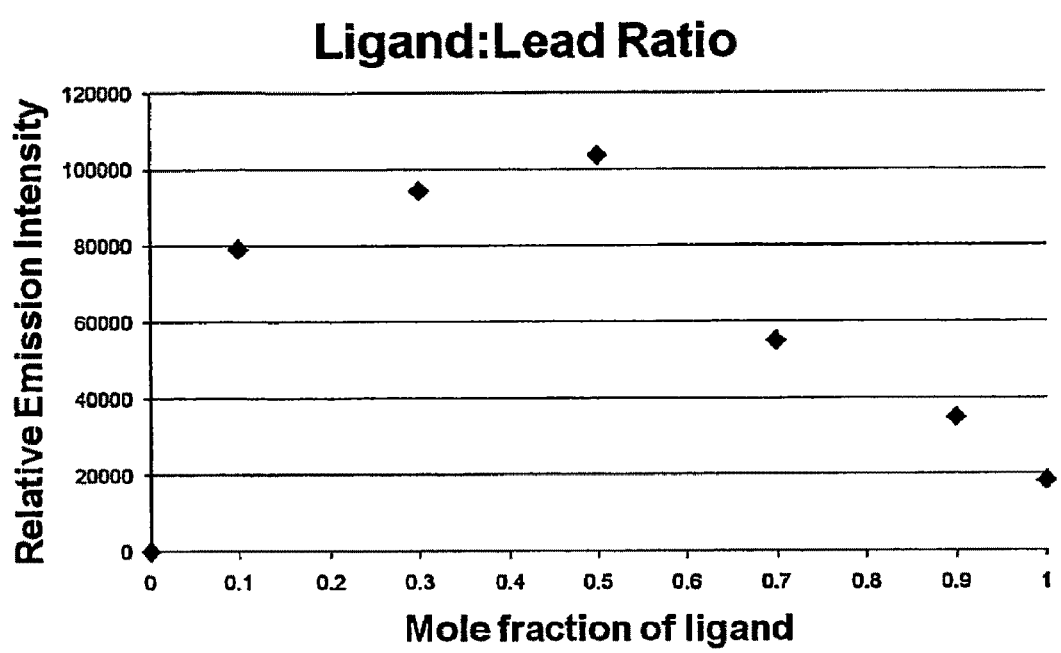
FIG. 12 illustrates a plot of the intensity of the fluorescence emission spectrum relative to ligand/metal complex ratio.
Figure 13:
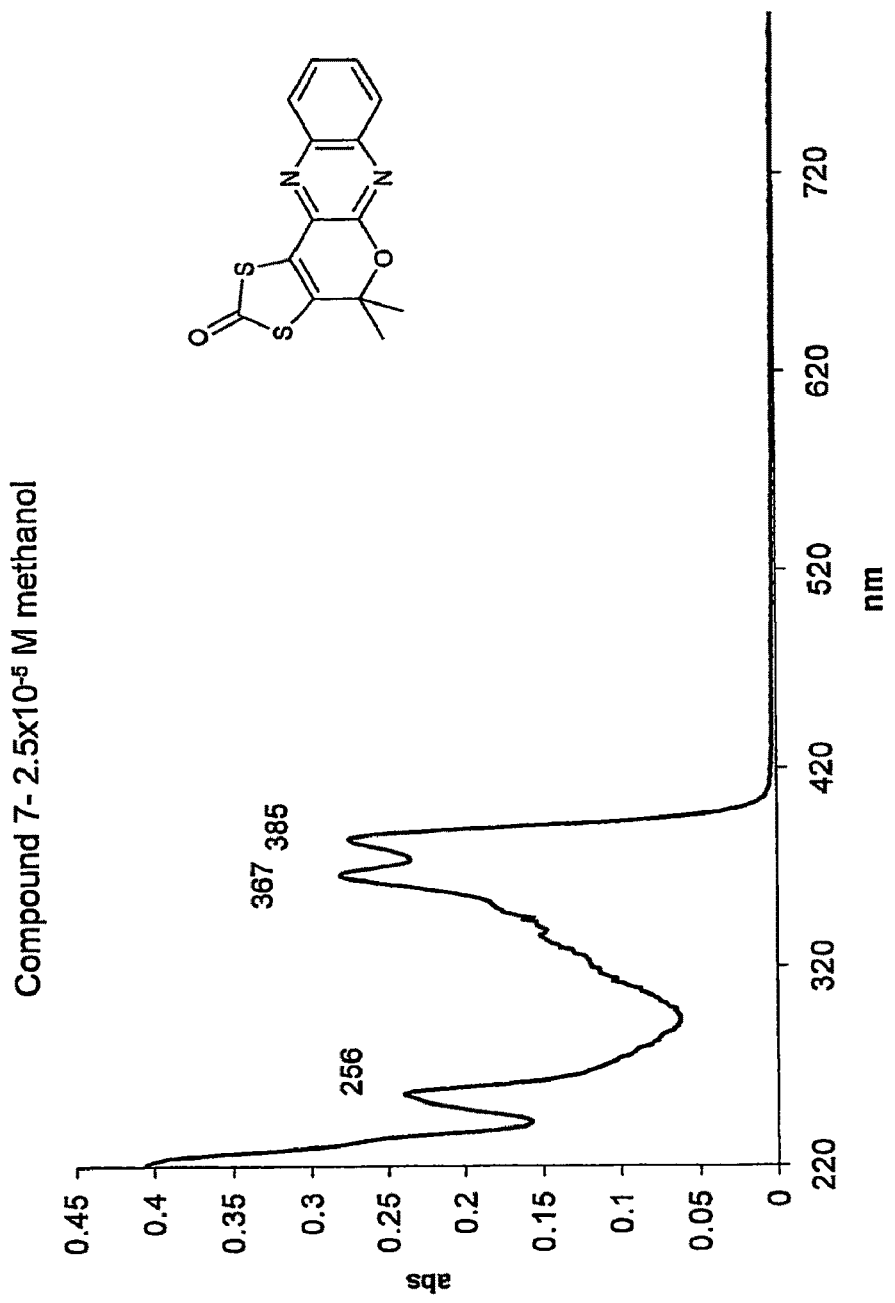
FIGS. 13-14 illustrate electronic spectra and excitation and emission spectra of one fluorophore of the present disclosure in methanol.
Figure 14:
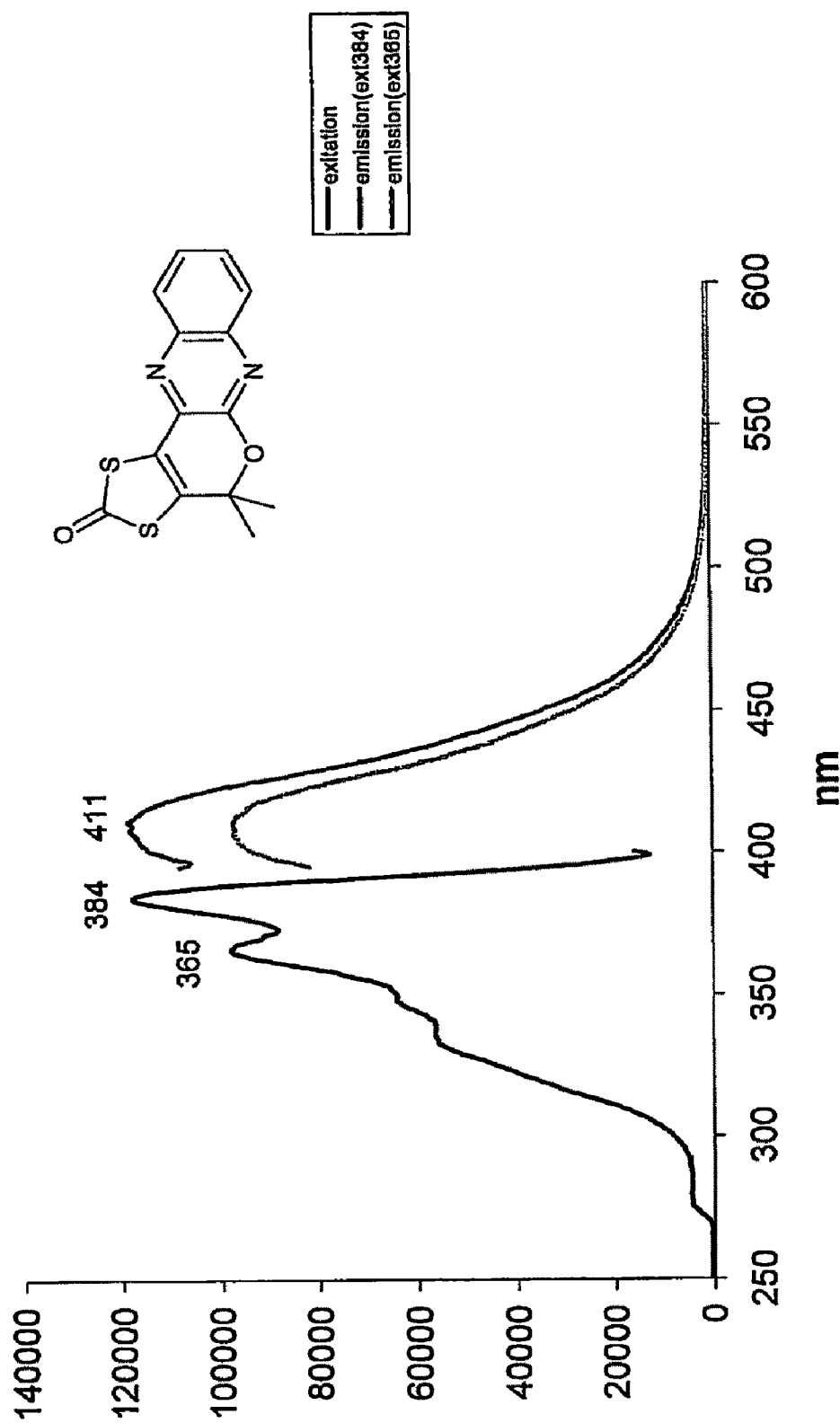
Figure 15:
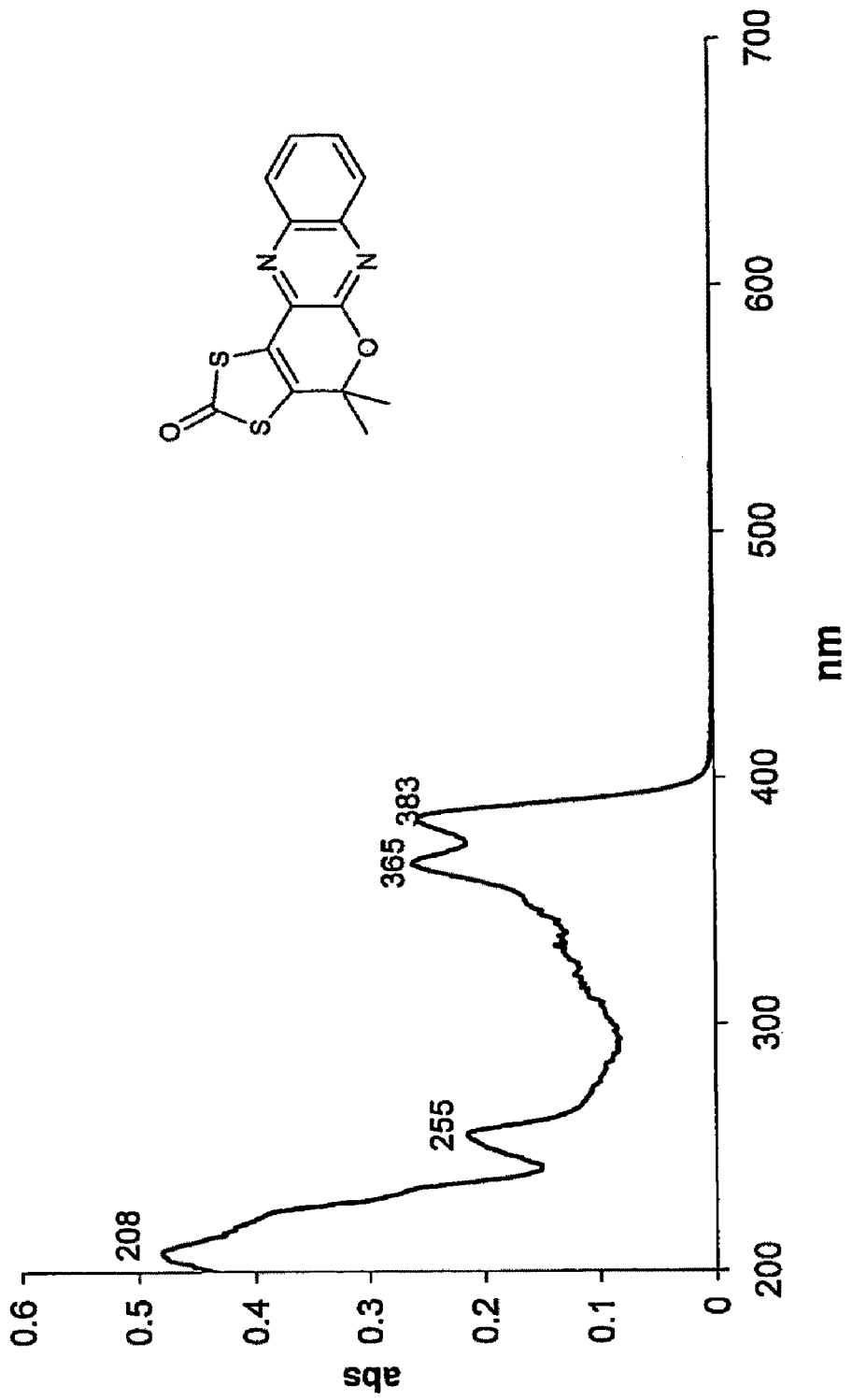
FIGS. 15-18 illustrate electronic spectra and excitation and emission spectra of one fluorophore of the present disclosure in acetonitrile.
Figure 16:
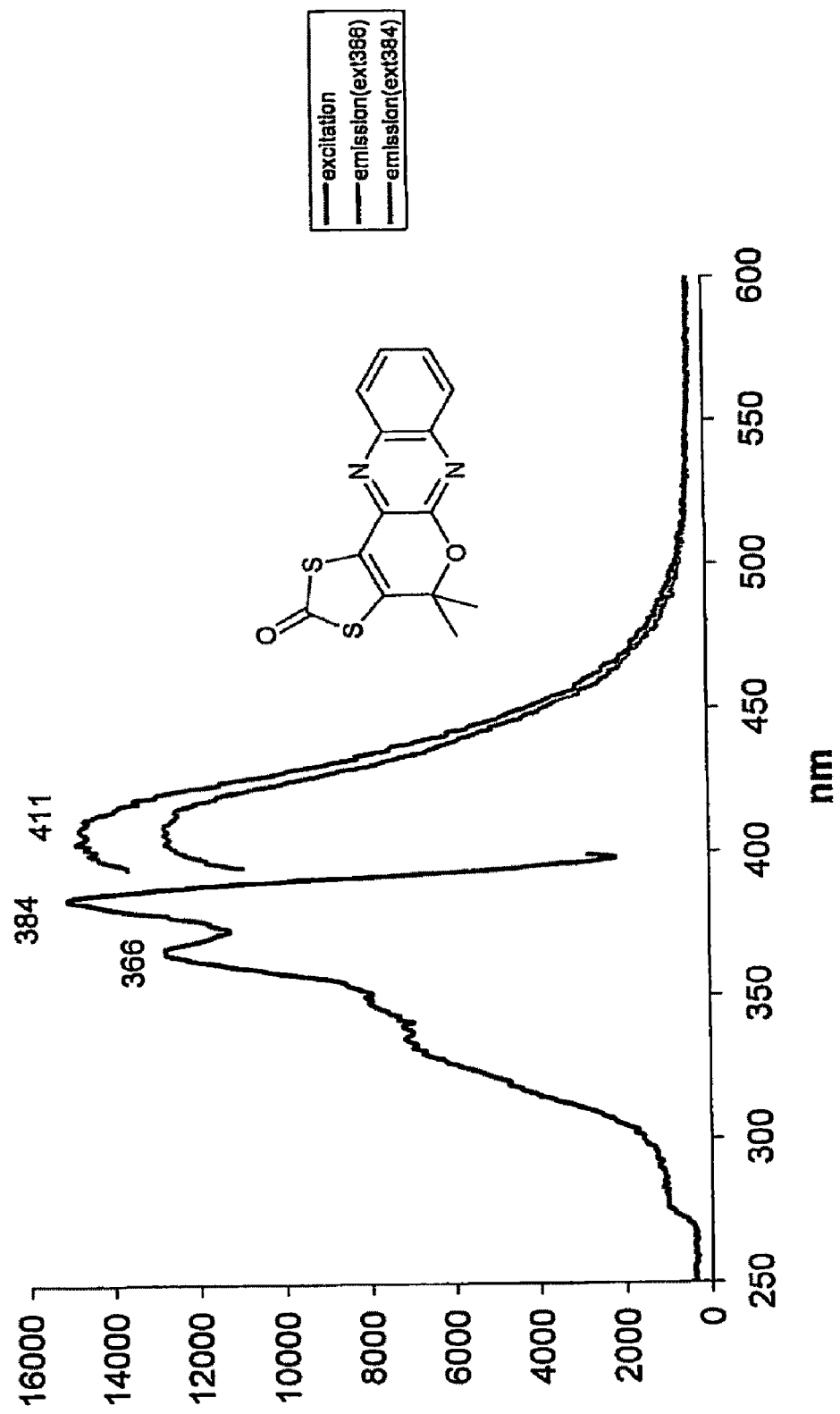
Figure 17:
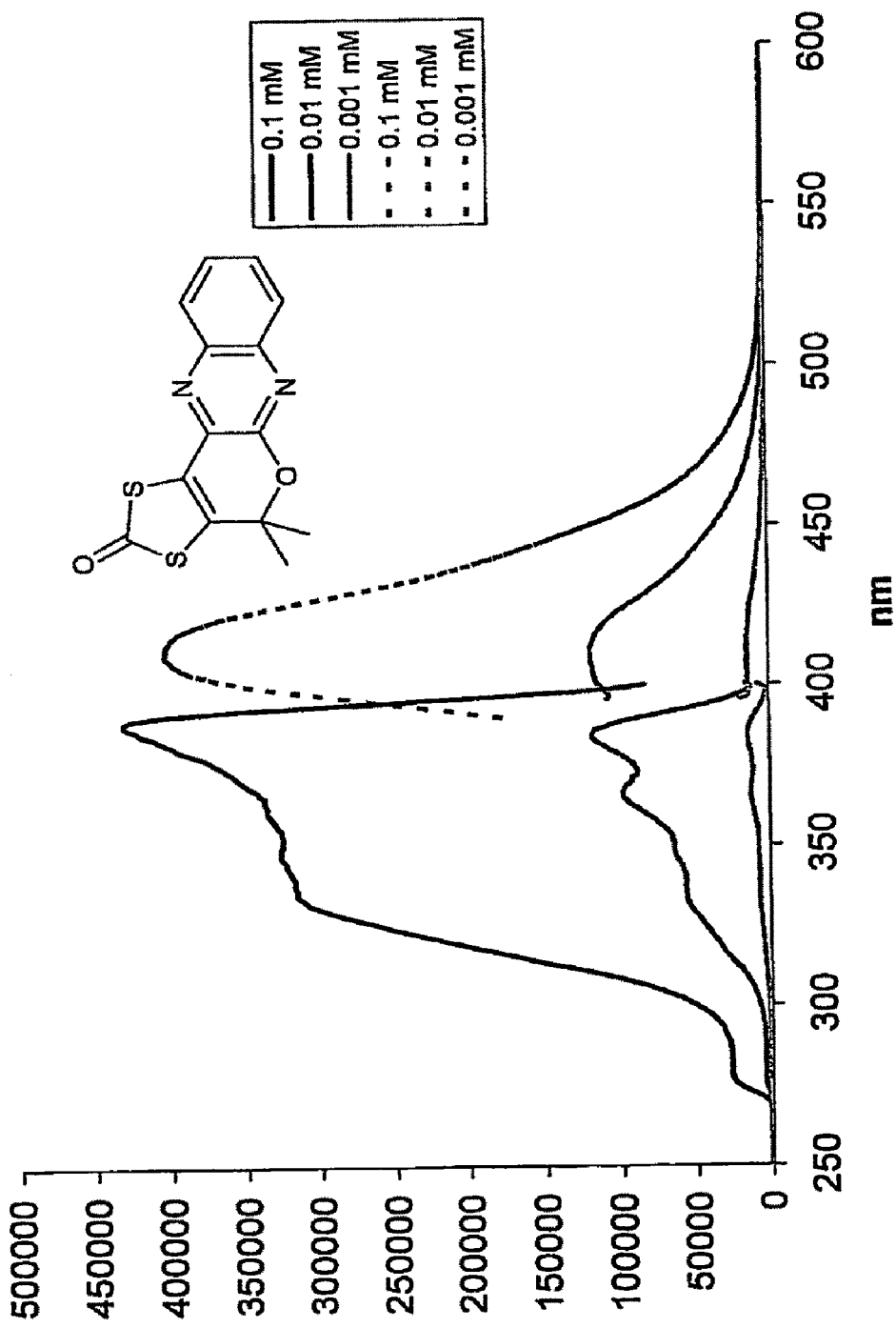
Figure 18:
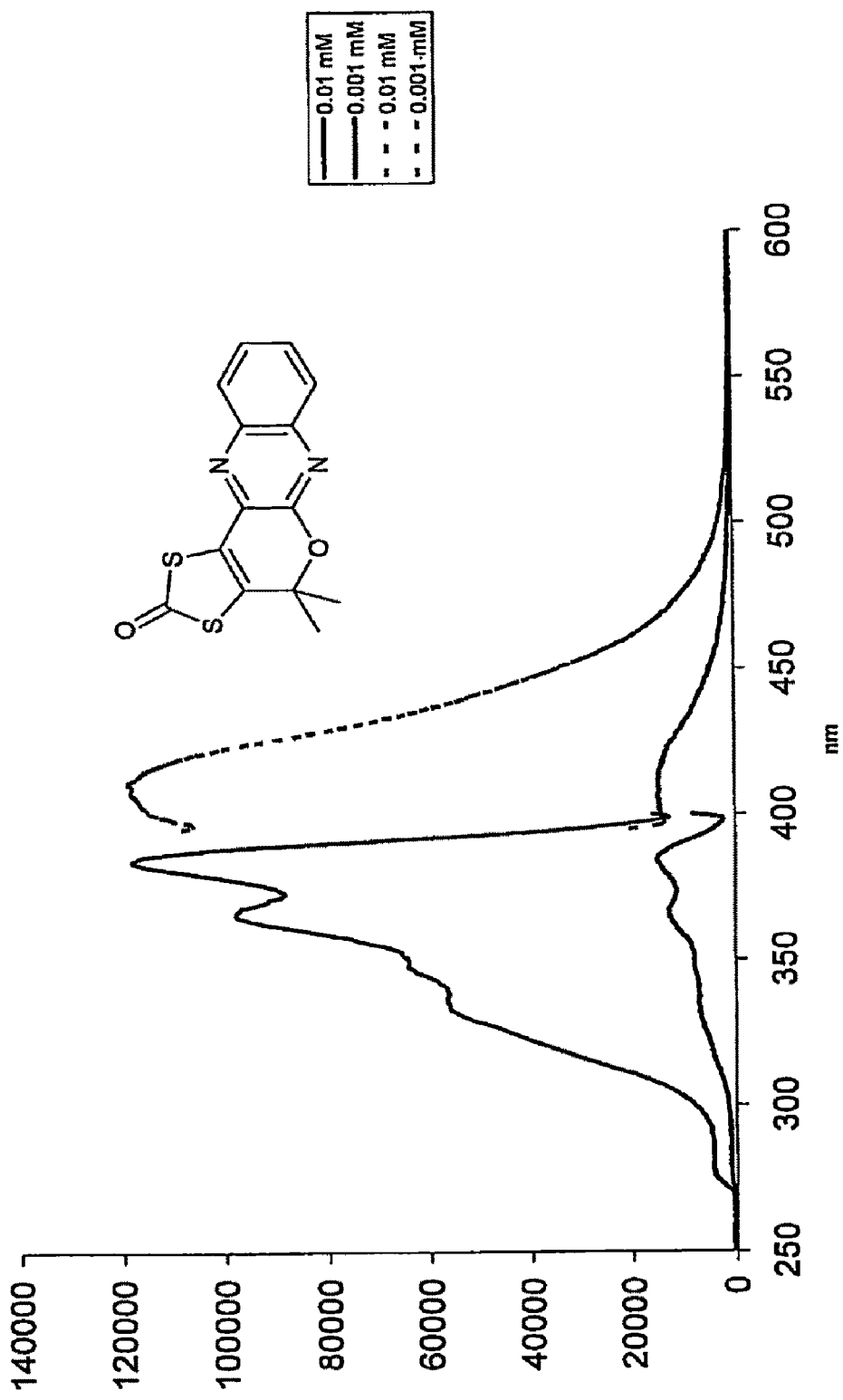
Figure 19:
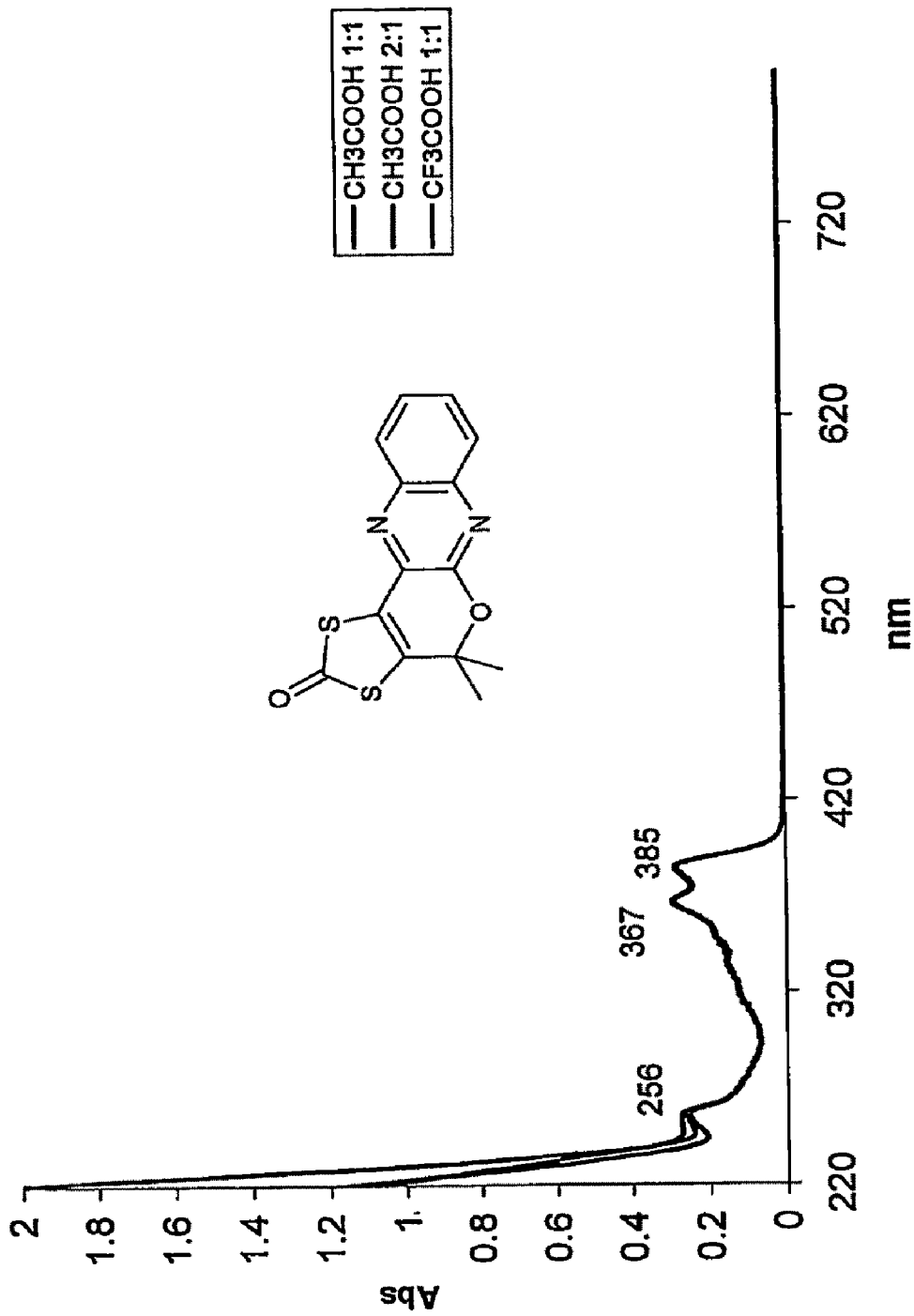
FIGS. 19-23 illustrate electronic spectra and excitation and emission spectra of one fluorophore of the present disclosure in methanol with acid or $Et_4NOH$.
Figure 20:
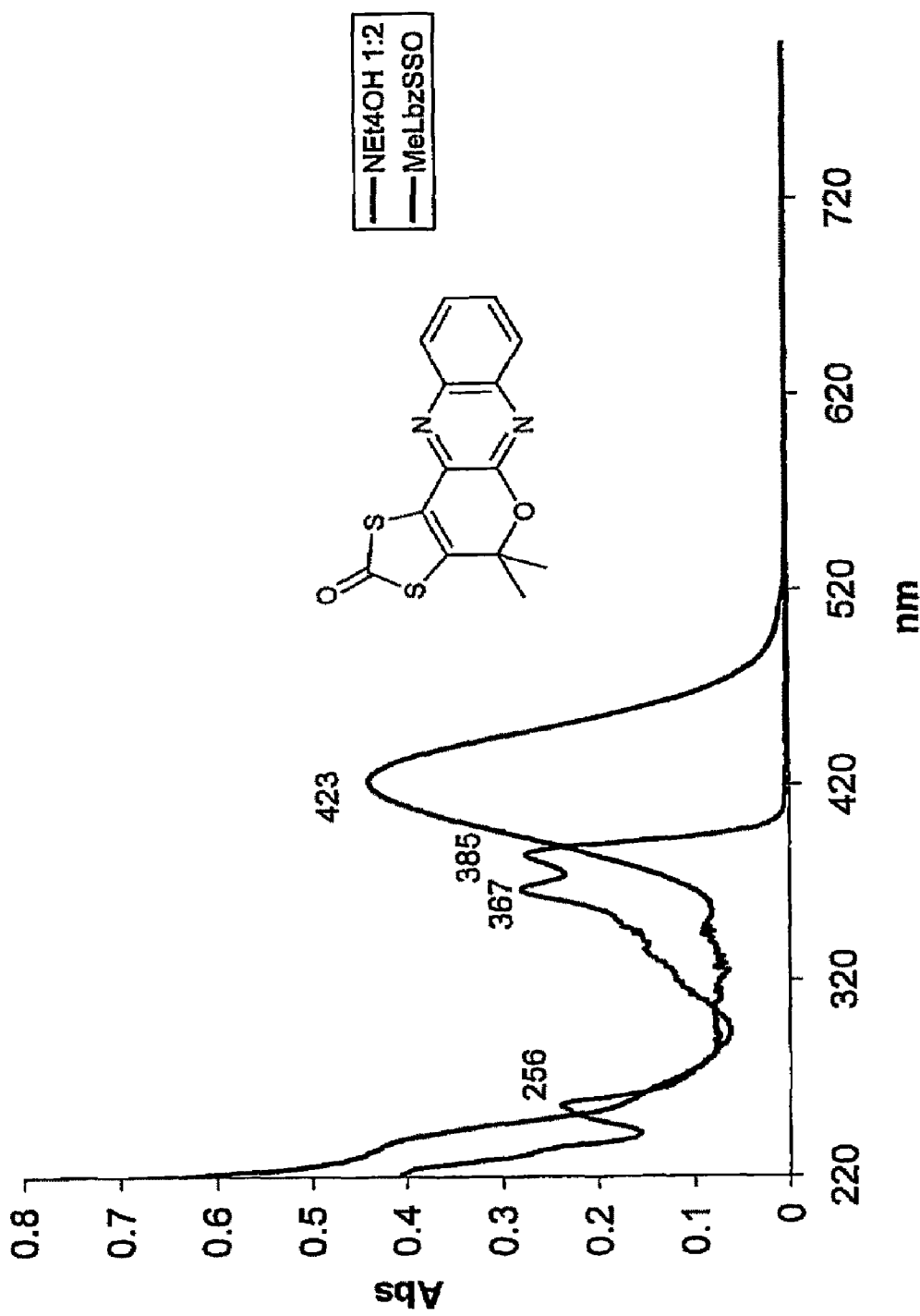
Figure 21:
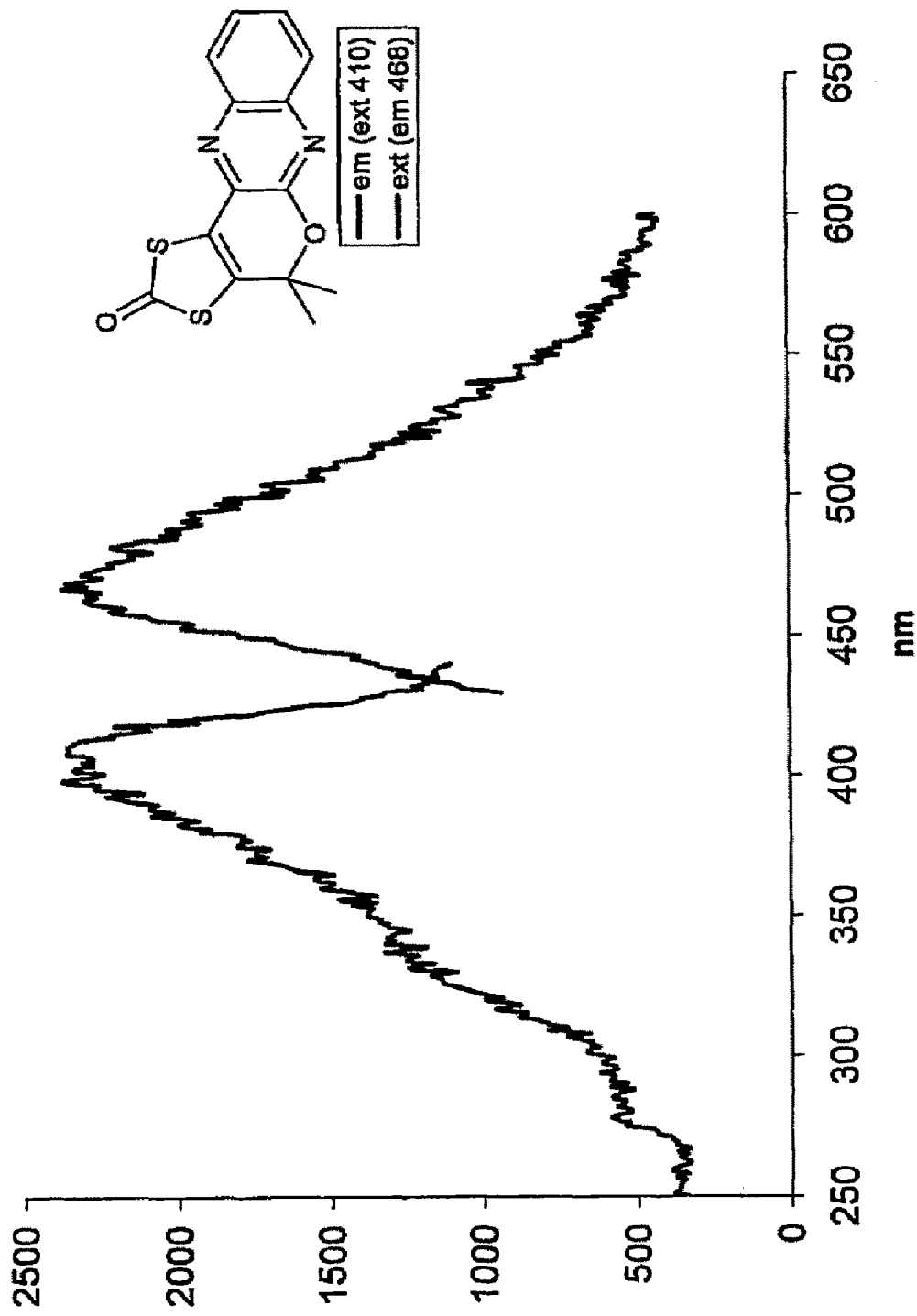
Figure 22:
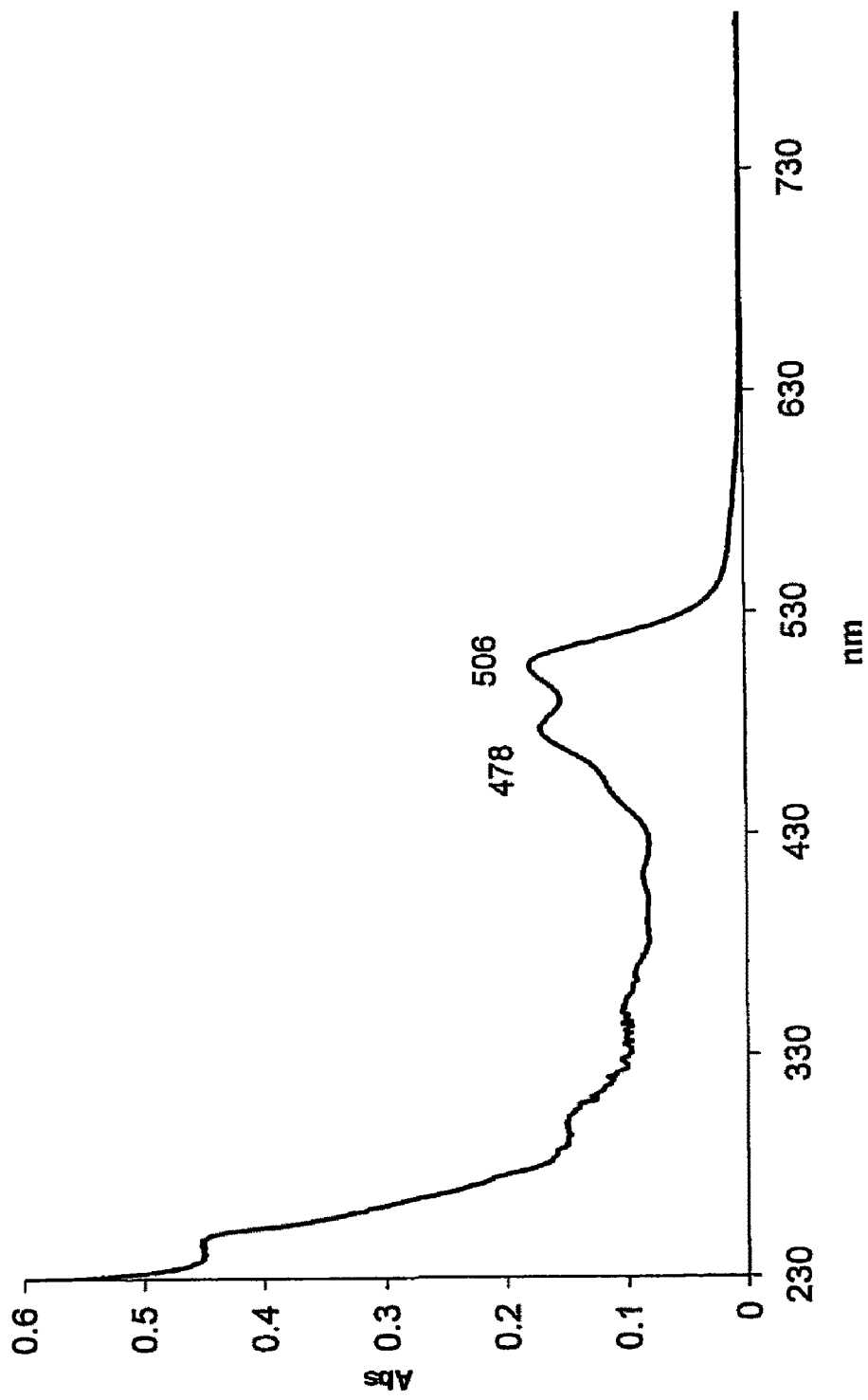
Figure 23:
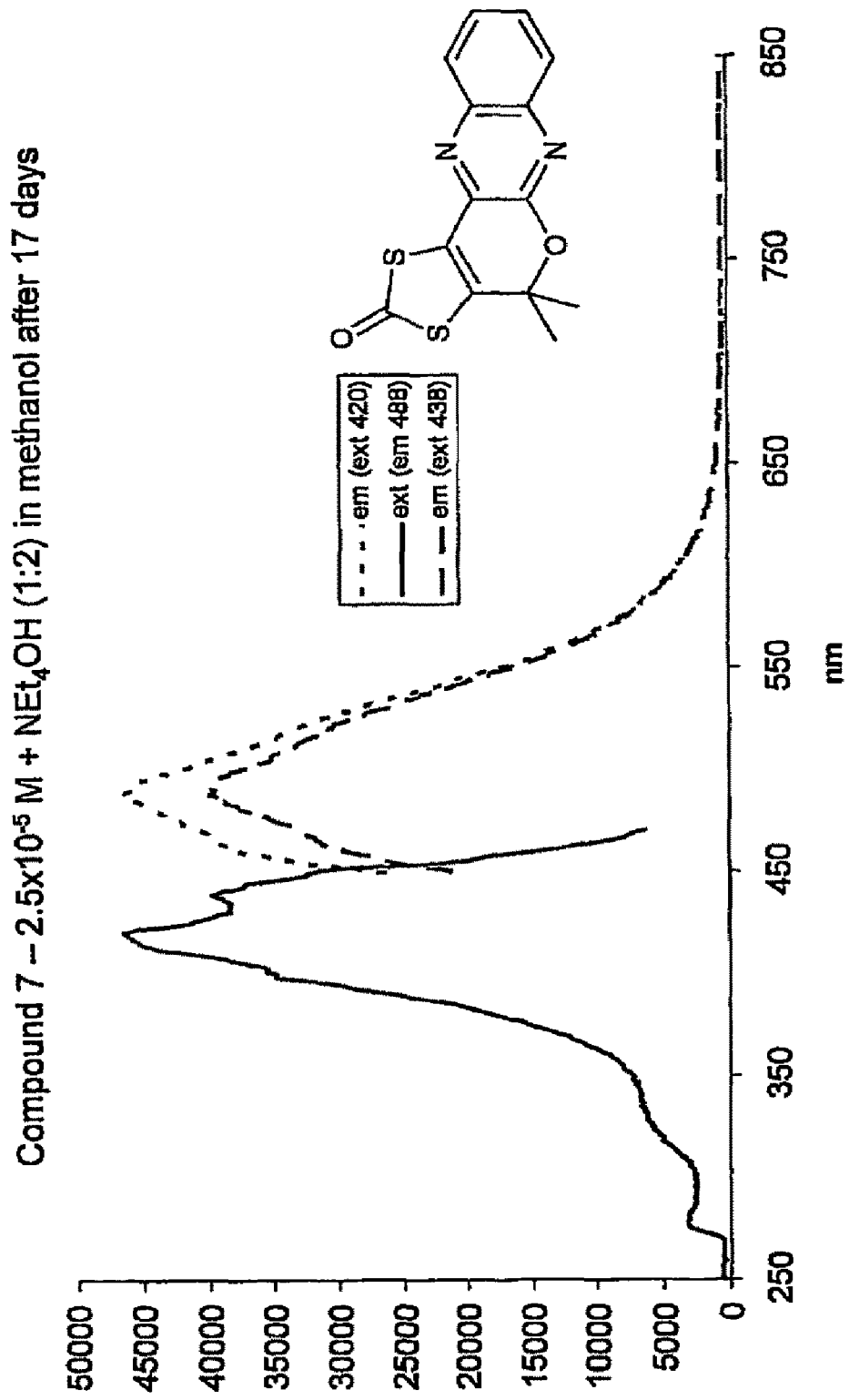
Figure 24:
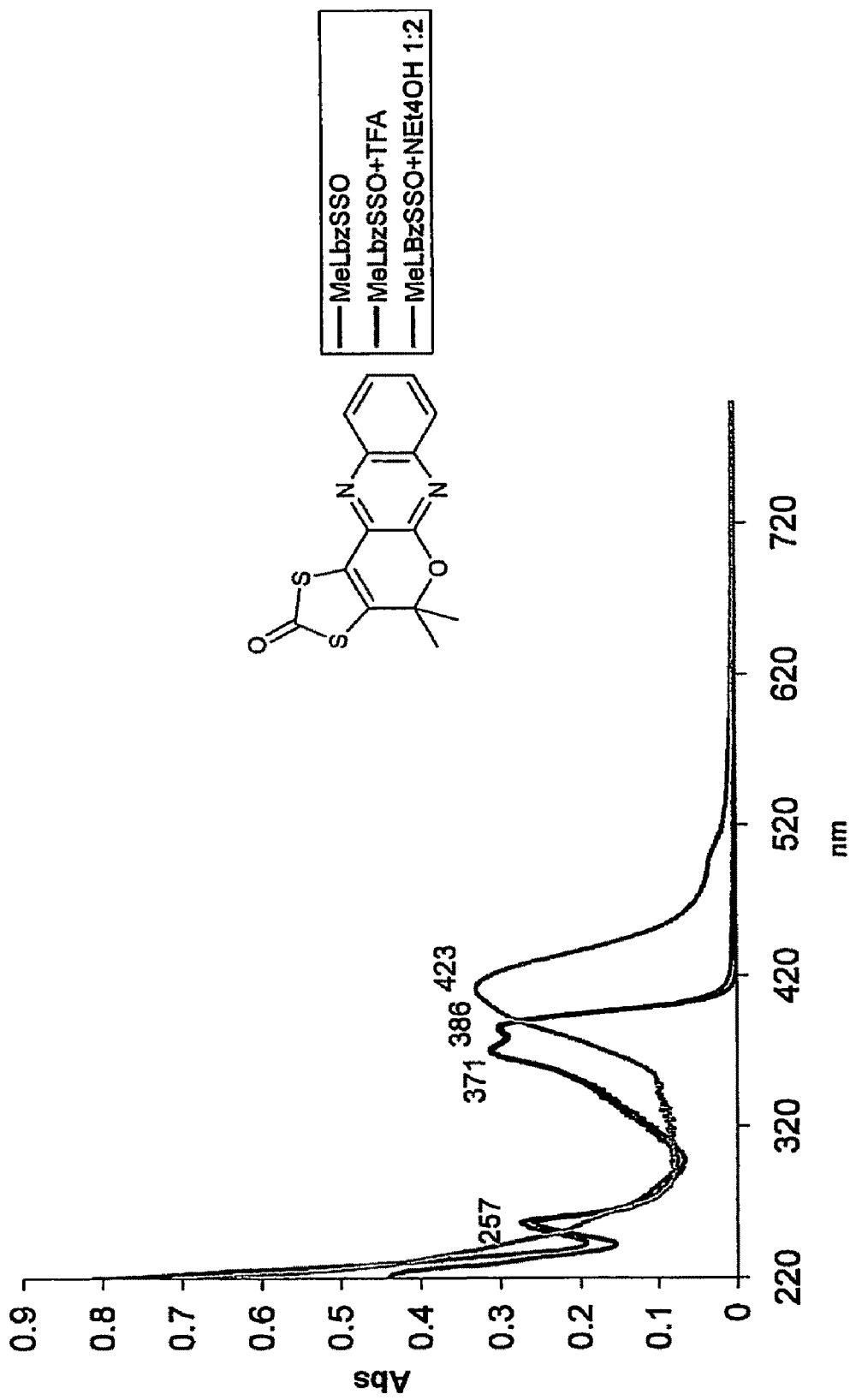
FIGS. 24-28 illustrate electronic spectra and excitation and emission spectra of one fluorophore of the present disclosure in methanol with trifluoroacetic acid (TFA) or $Et_4NOH$.
Figure 25:
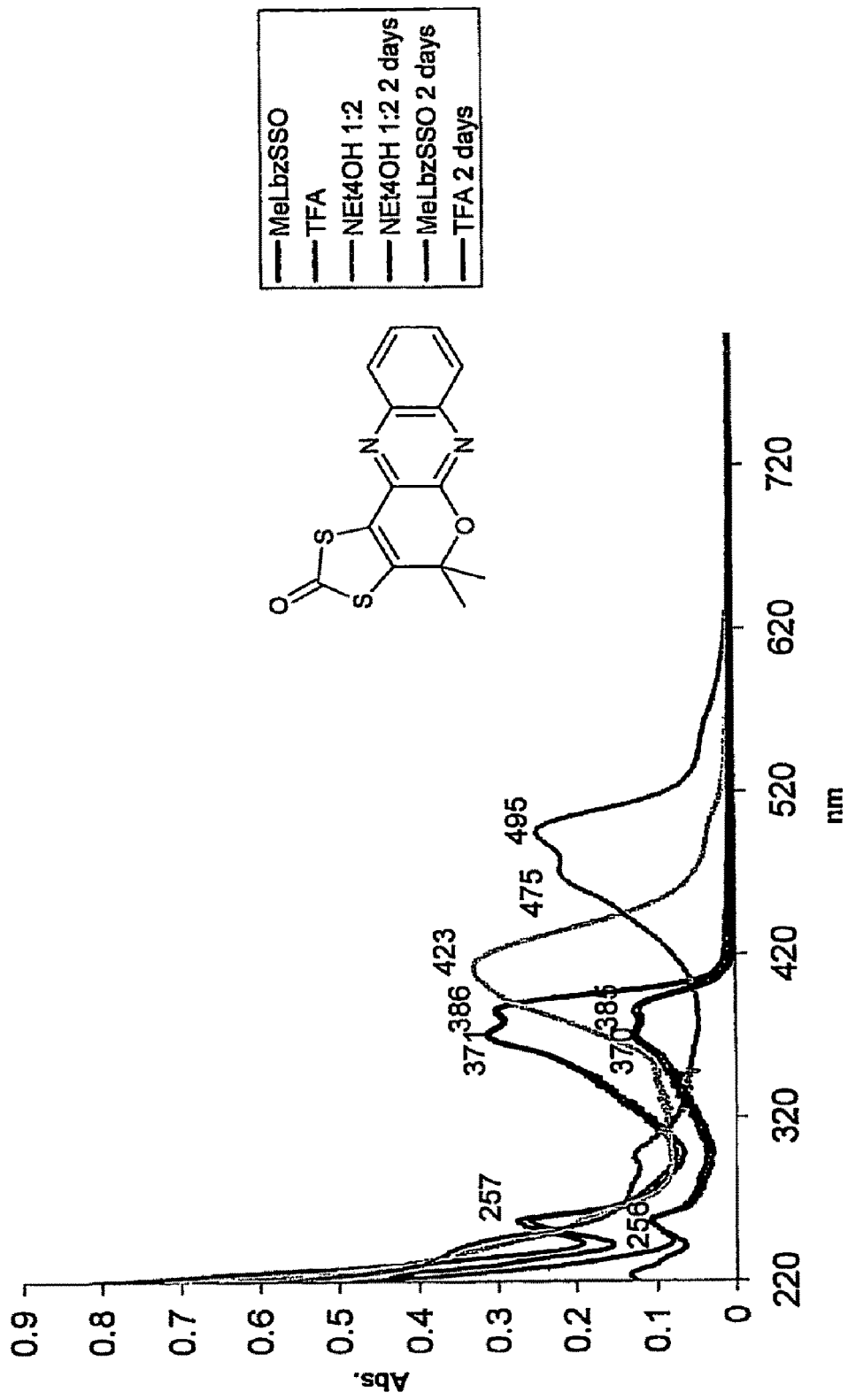
Figure 26:
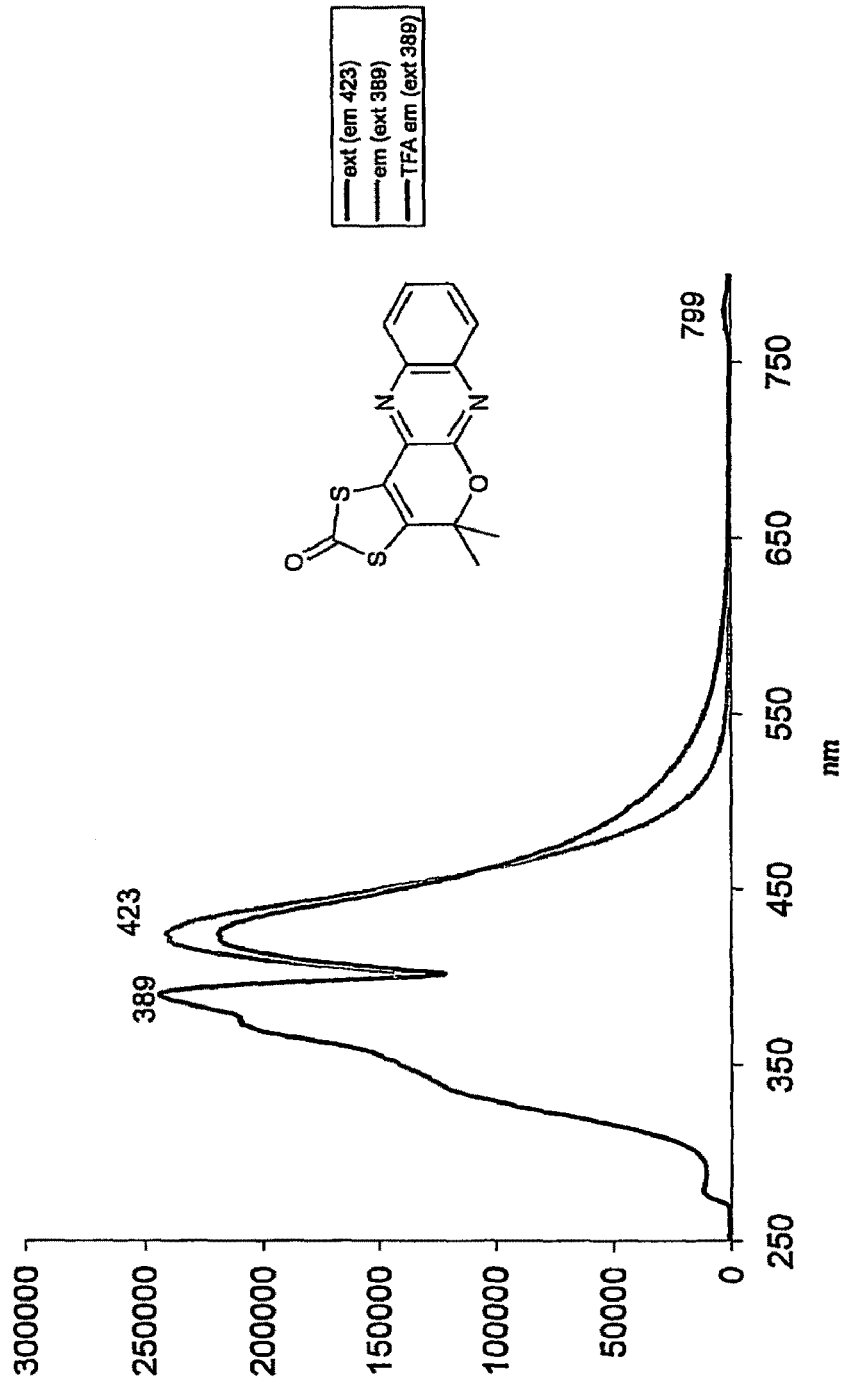
Figure 27:
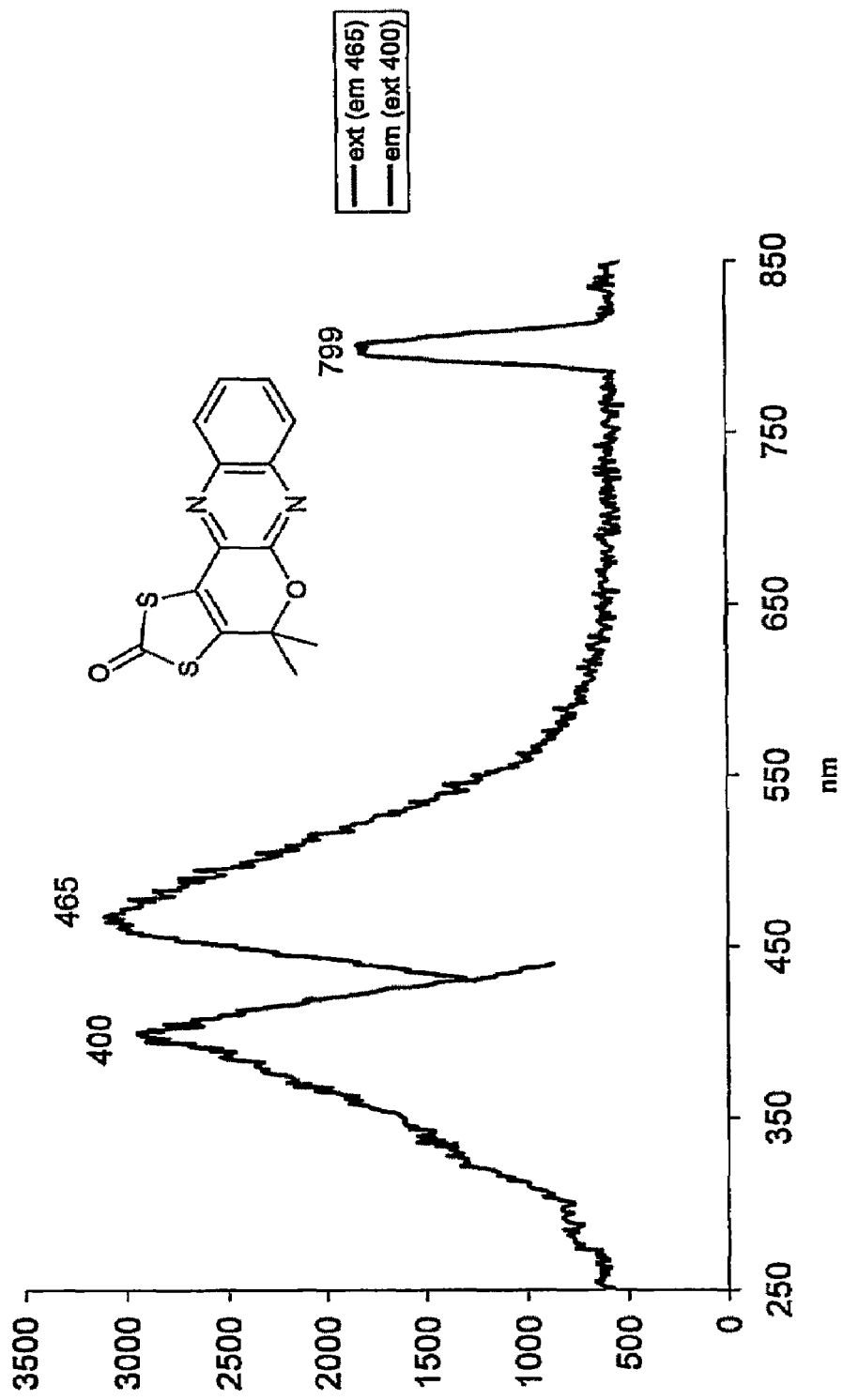
Figure 28:
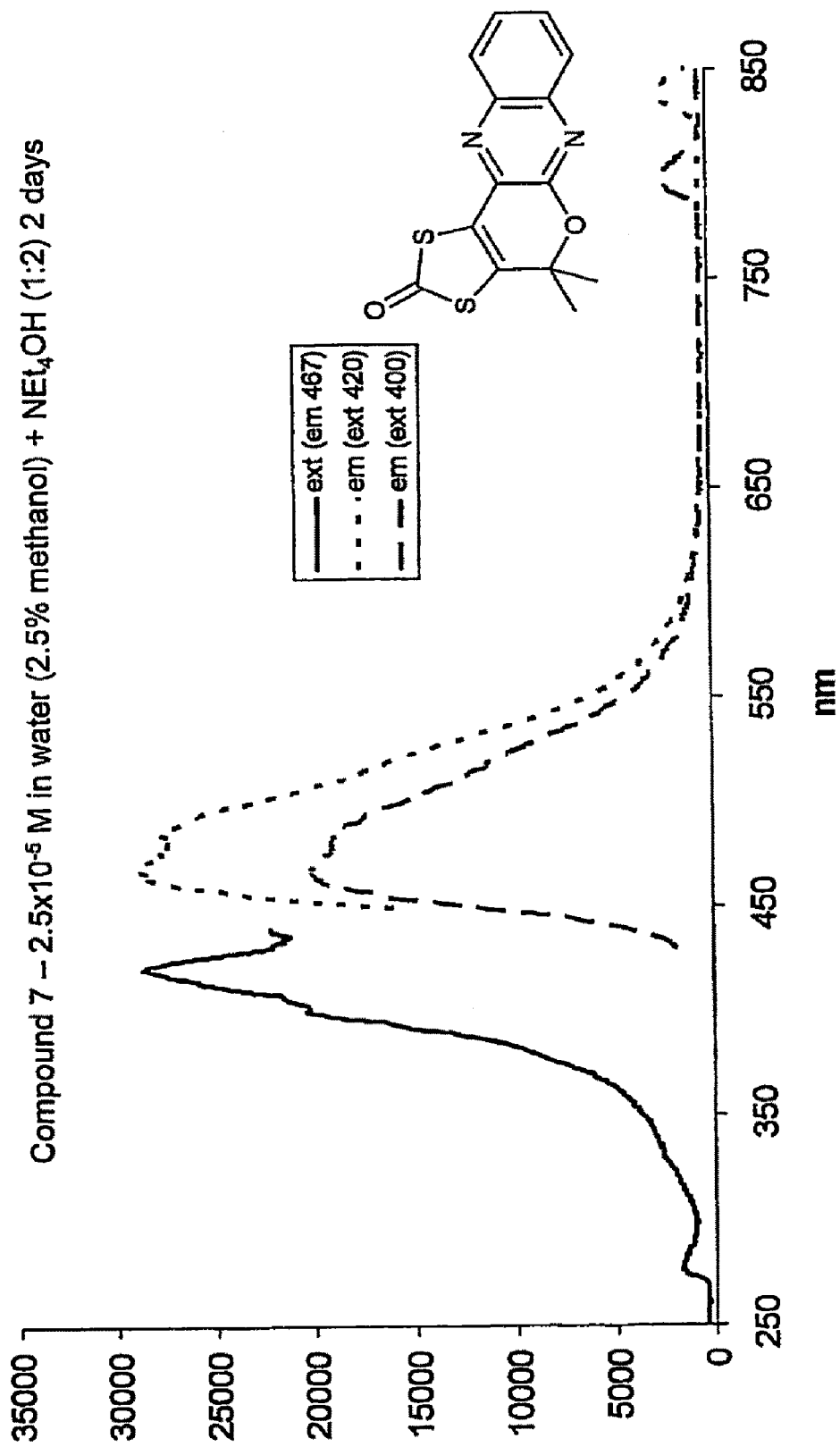
Figure 29:
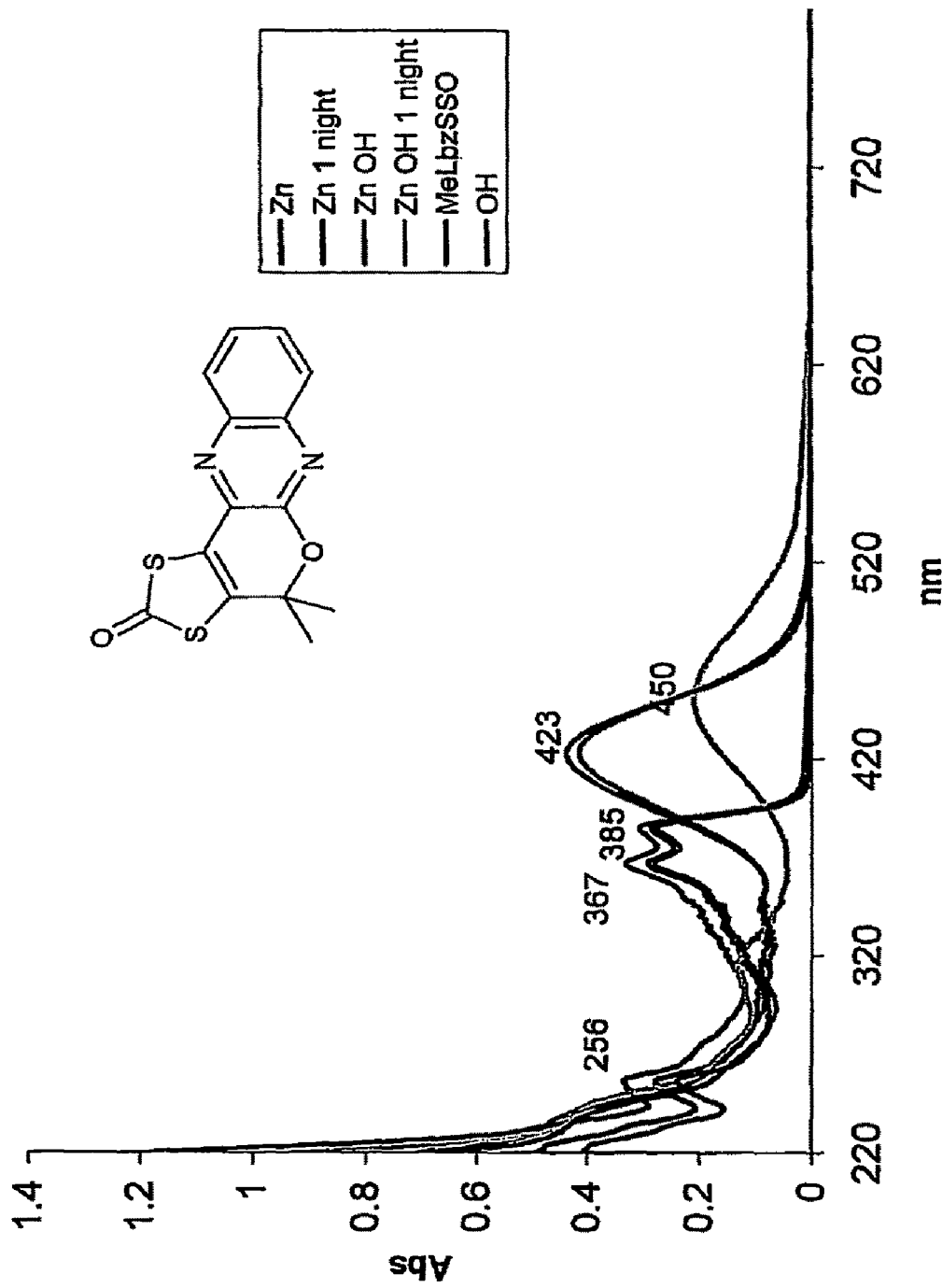
FIGS. 29-37 illustrate electronic spectra and excitation and emission spectra of one fluorophore of the present disclosure complexed to metal ions ($Zn^{2+}$, $Cd^{2+}$, $Hg^{2+}$, and $Pb^{2+}$).
Figure 30:
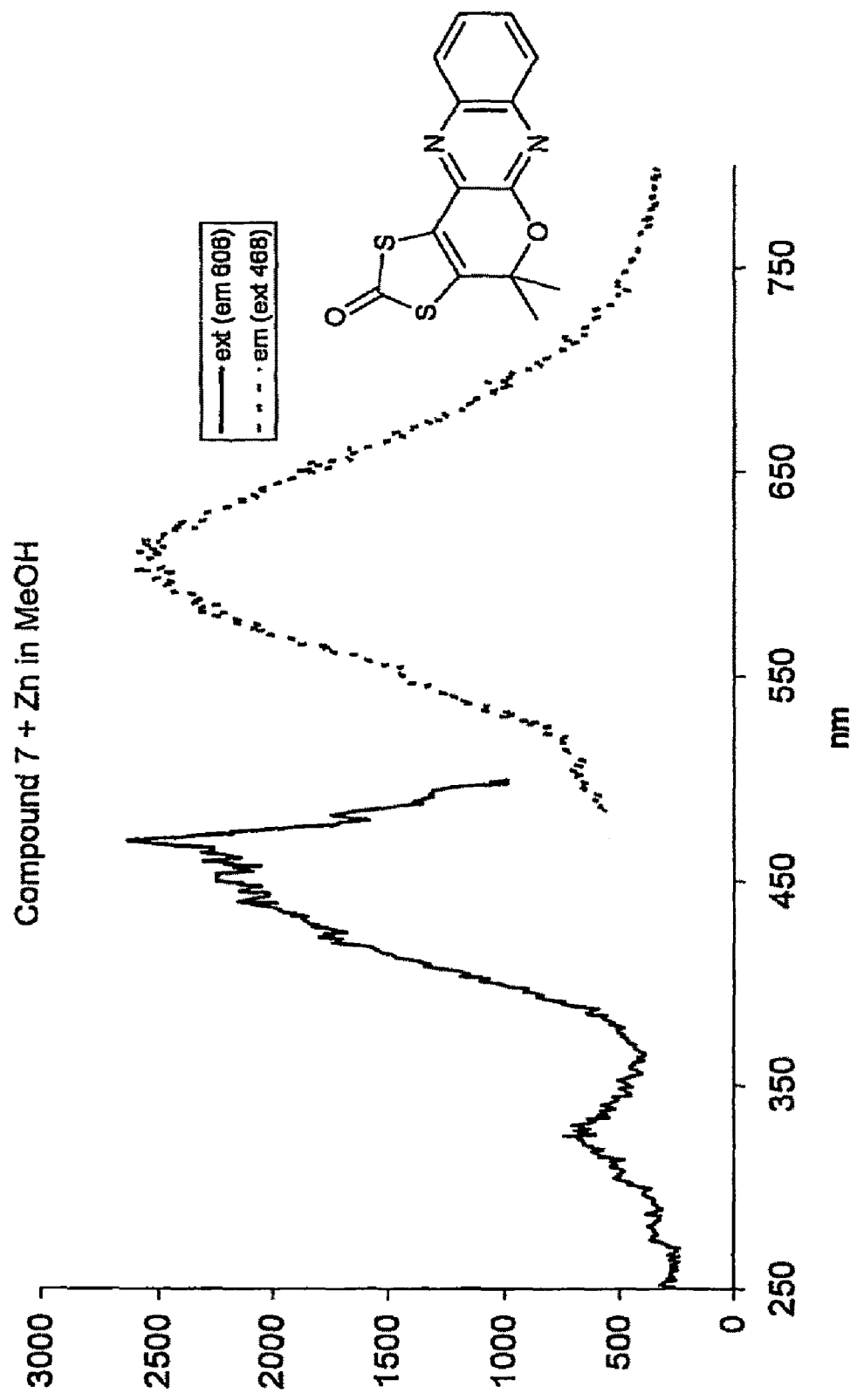
Figure 31:
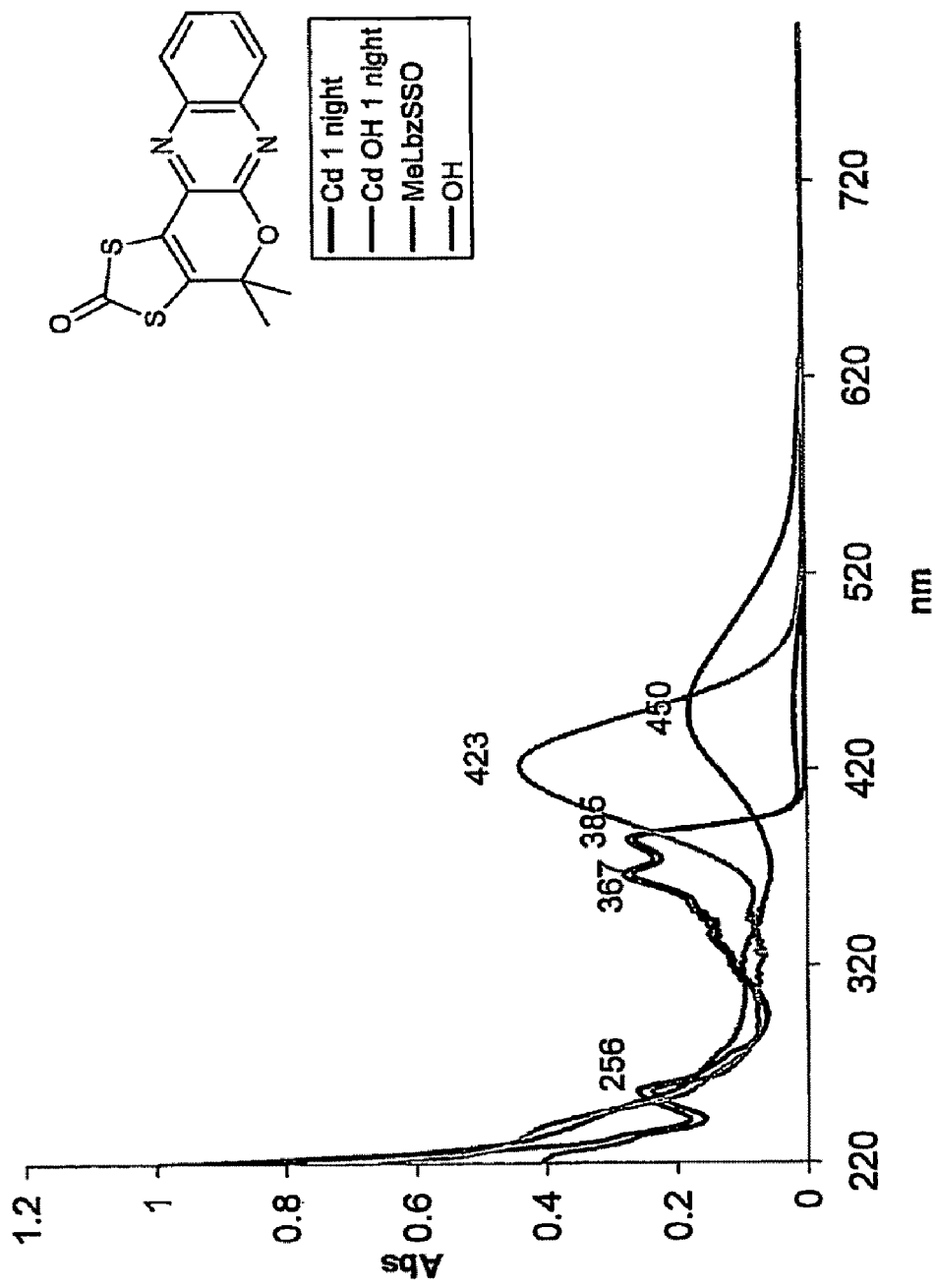
Figure 32:
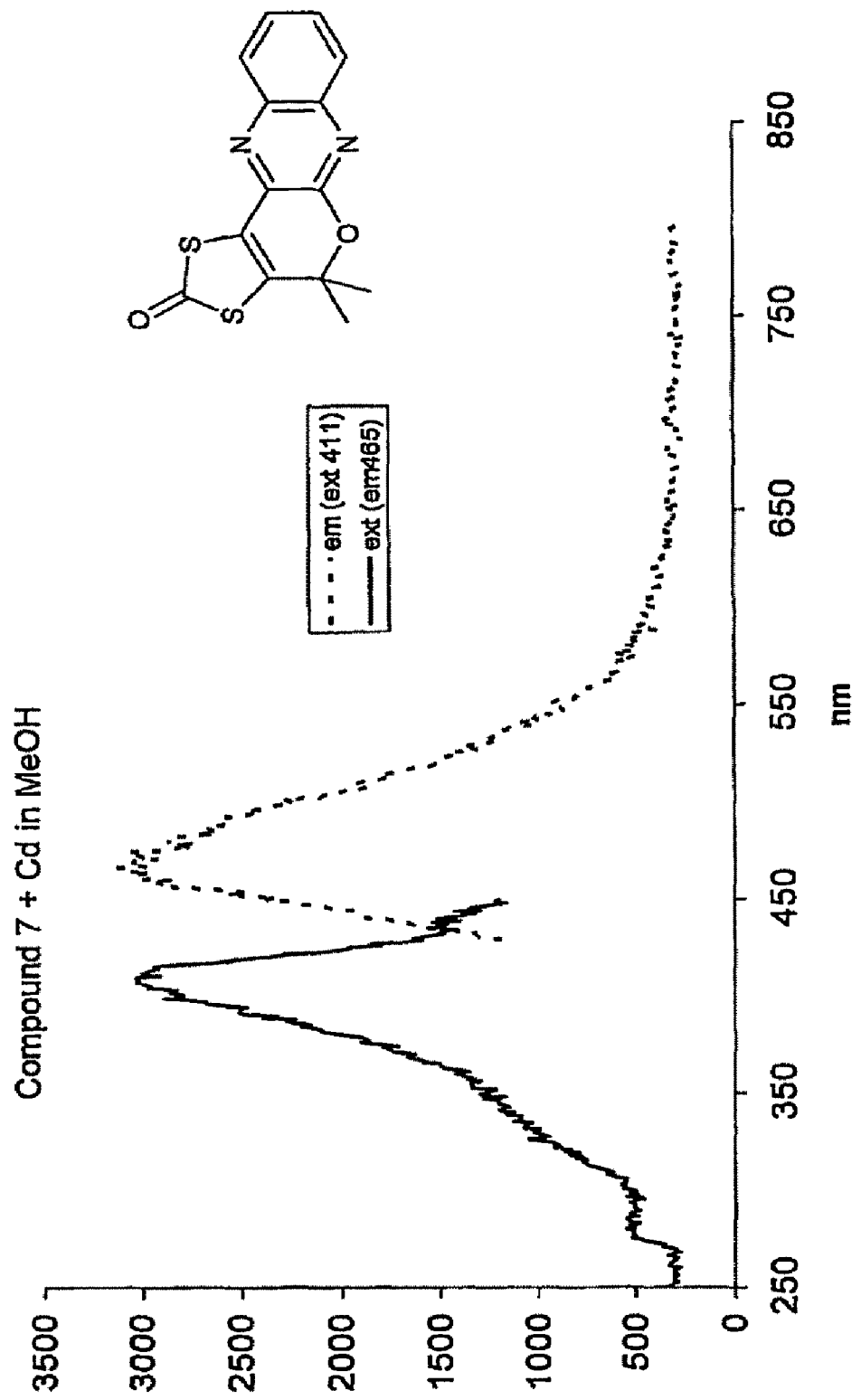
Figure 33:
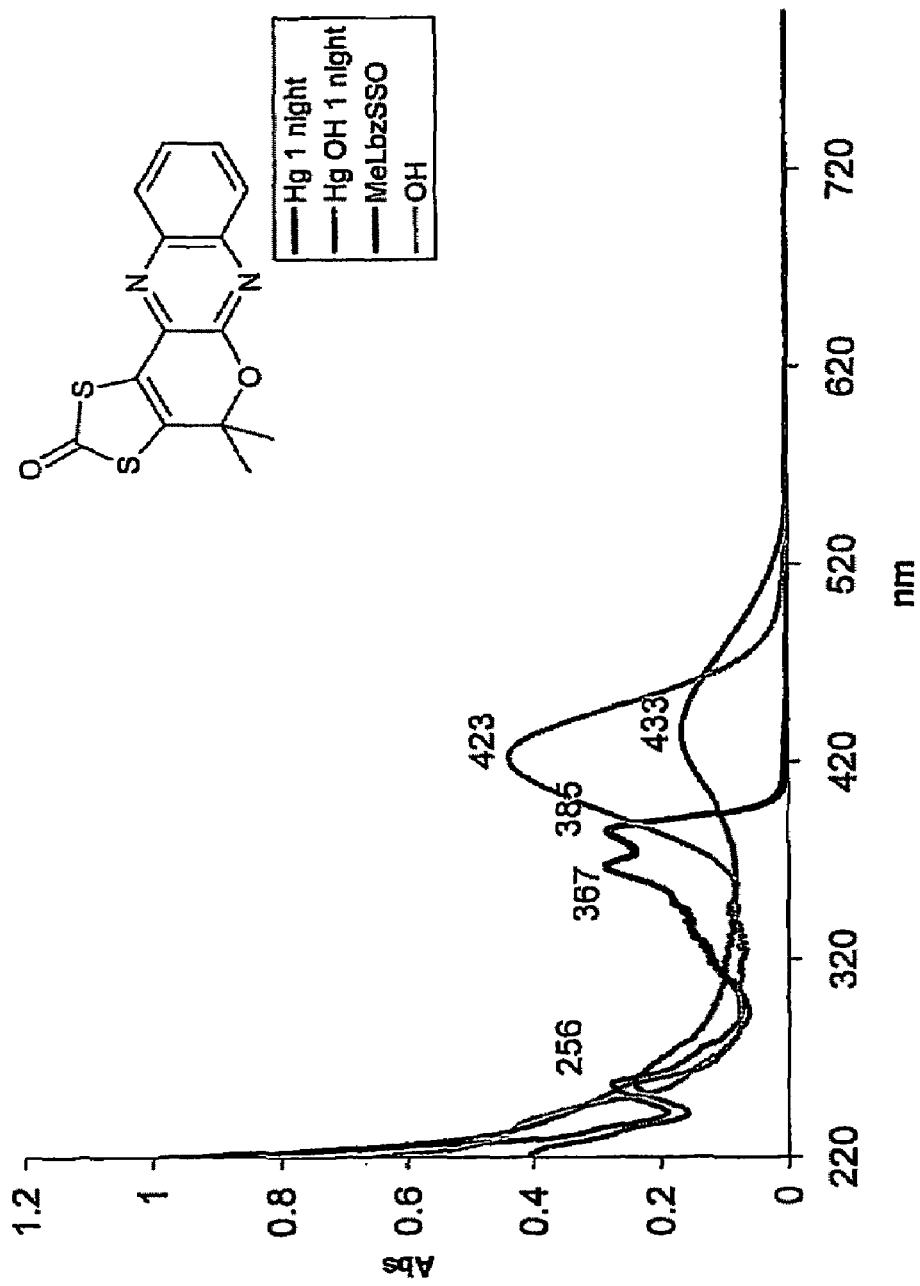
Figure 34:
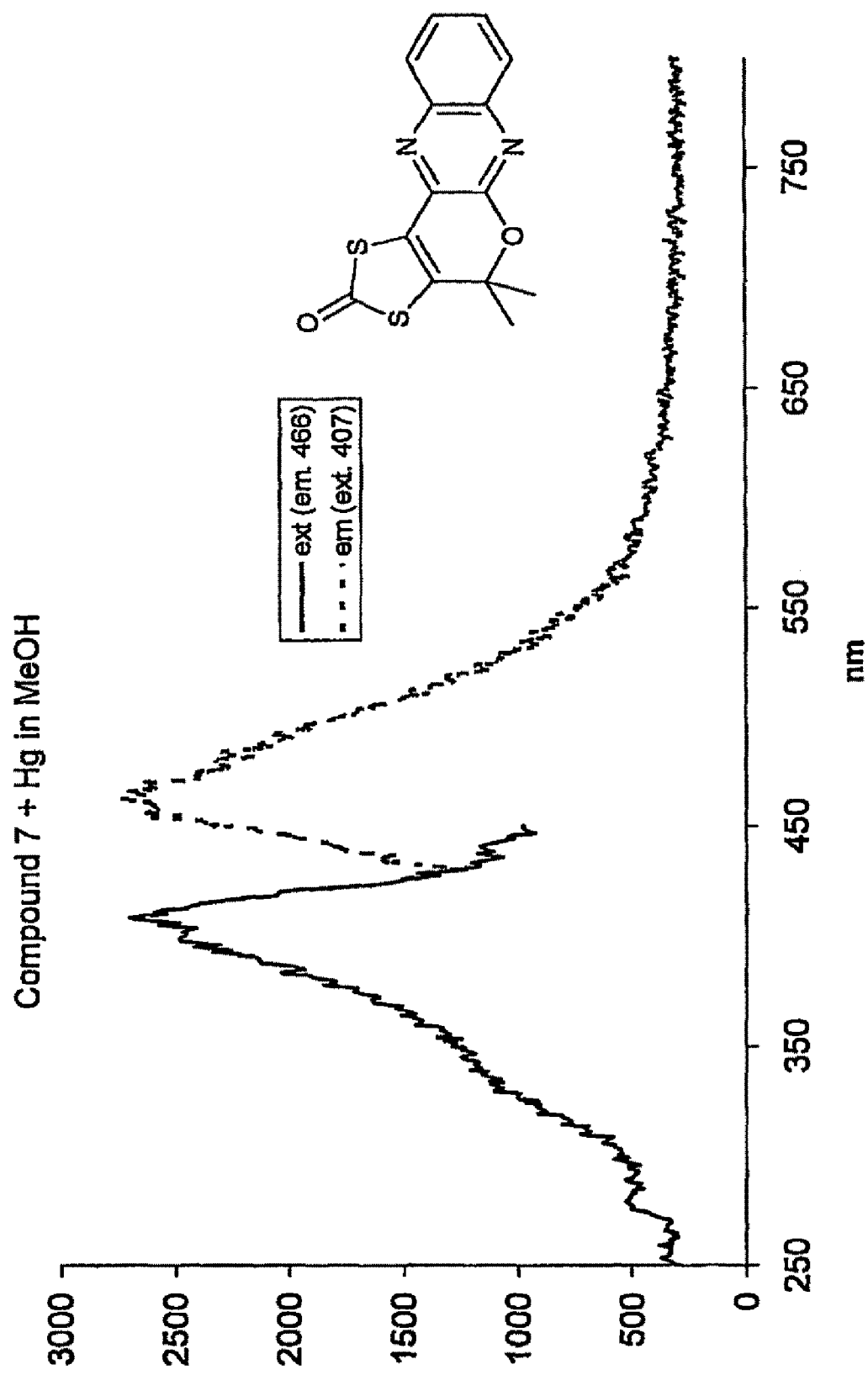
Figure 35:
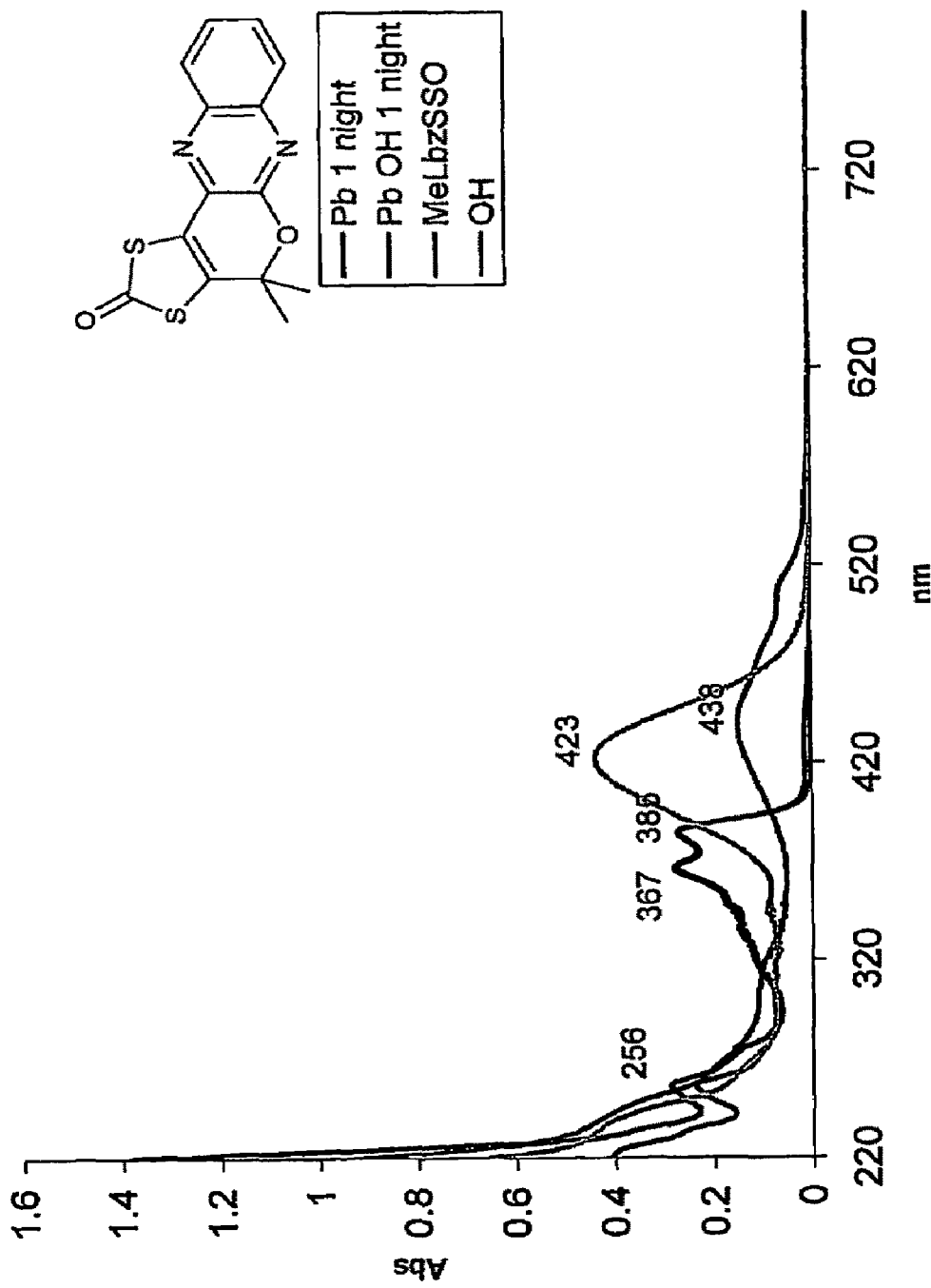
Figure 36:
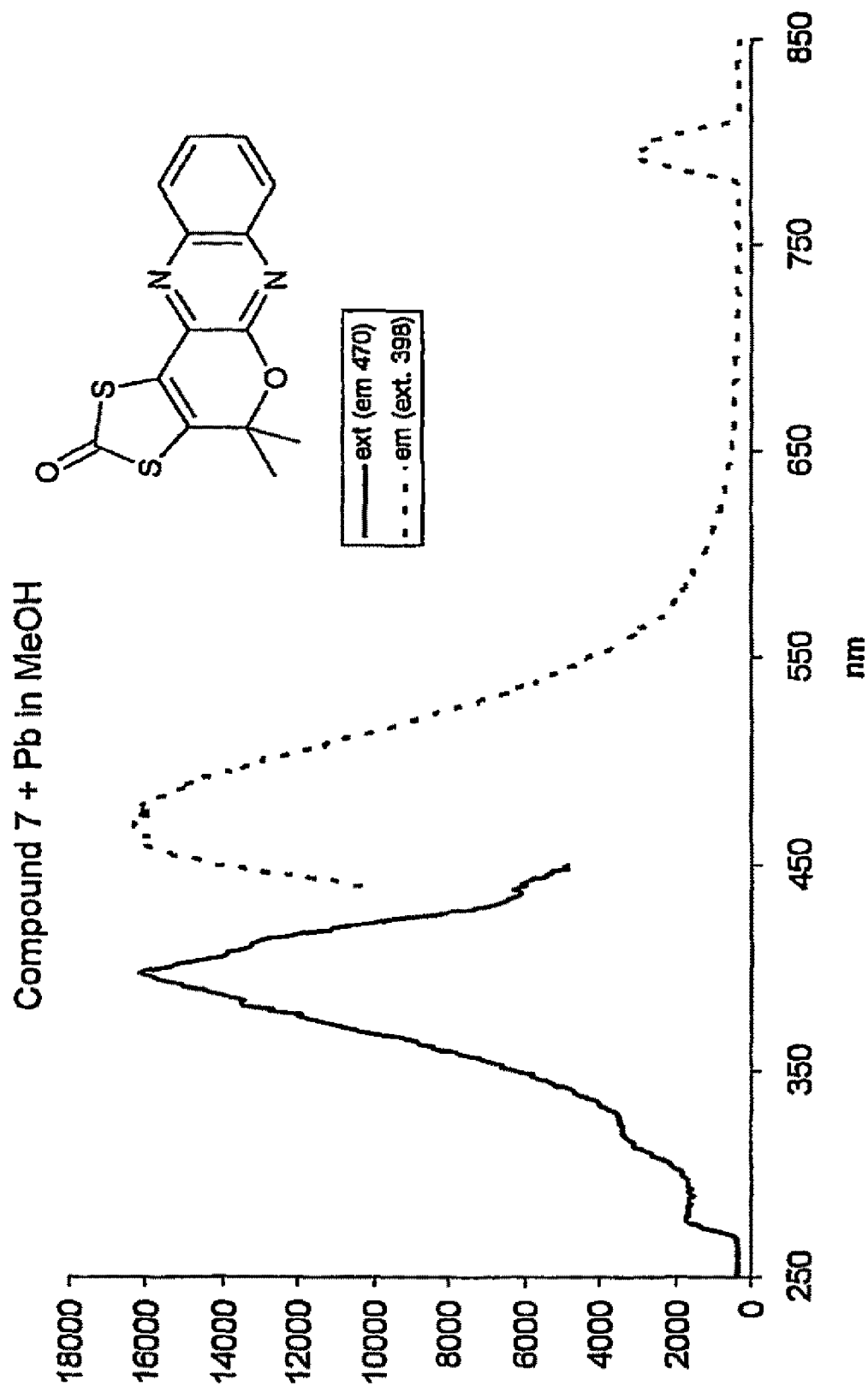
Figure 37:
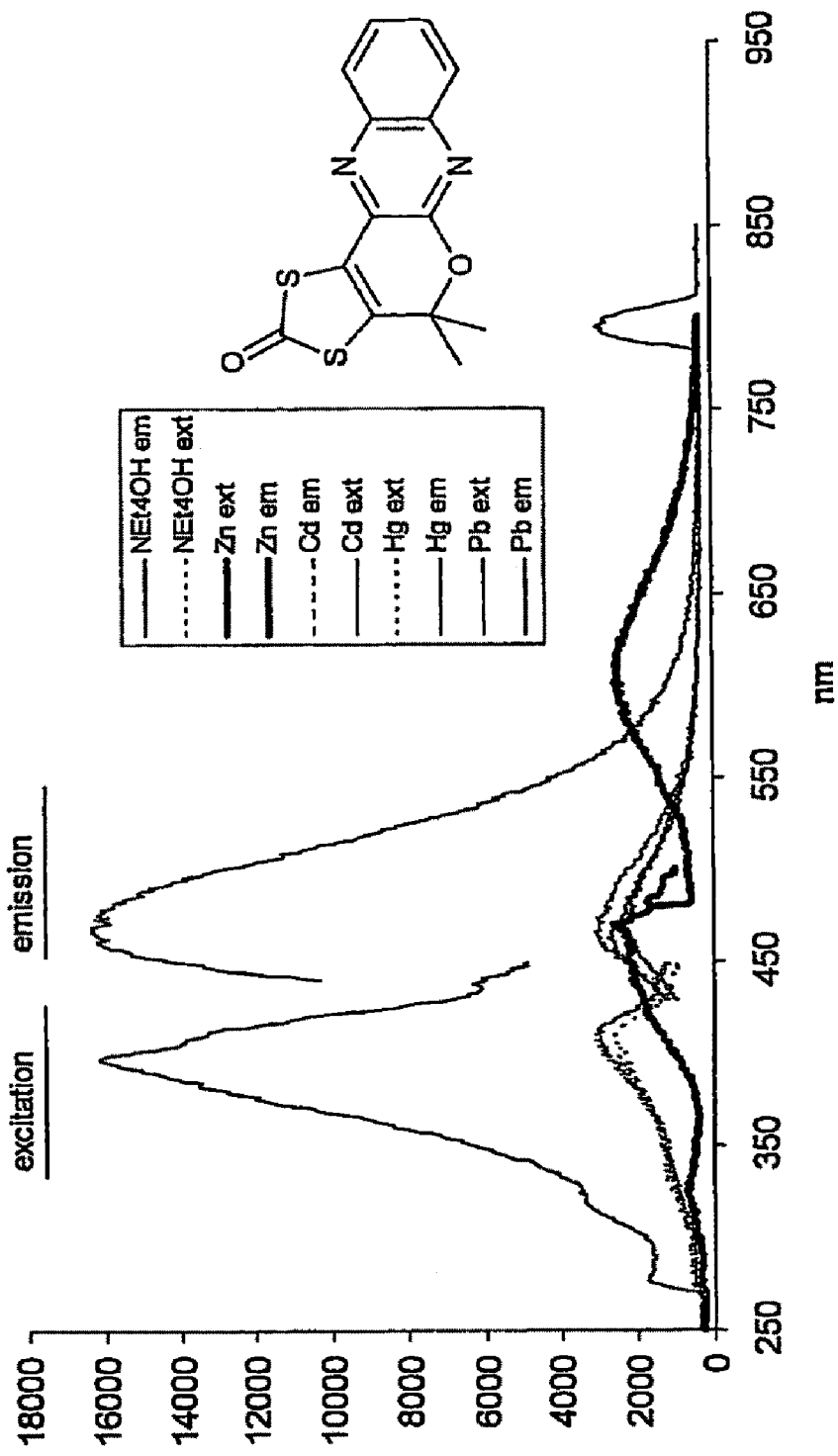
Figure 38:
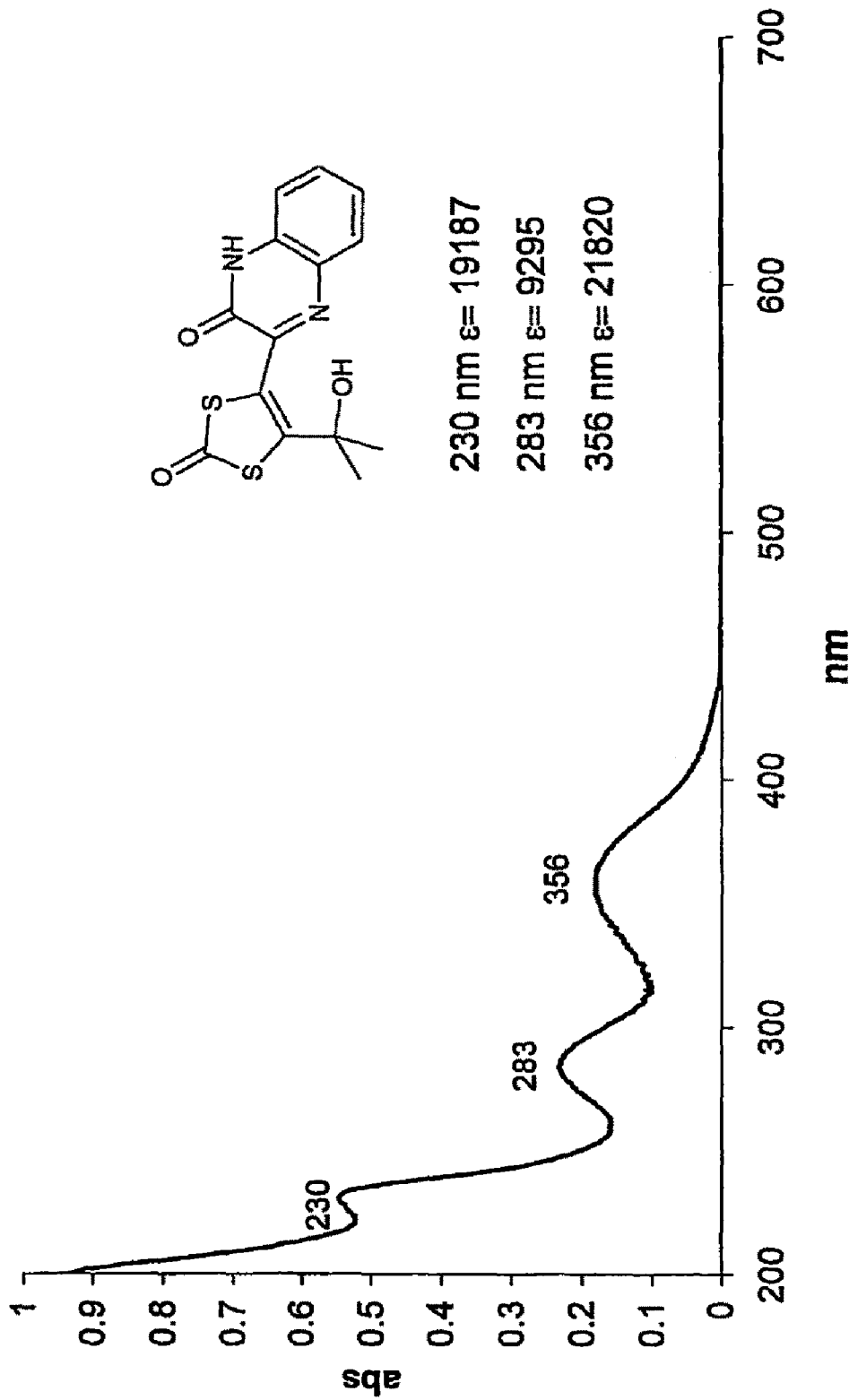
FIGS. 38-39 illustrate electronic spectra and excitation and emission spectra of the open form of one fluorophore of the present disclosure.
Figure 39:
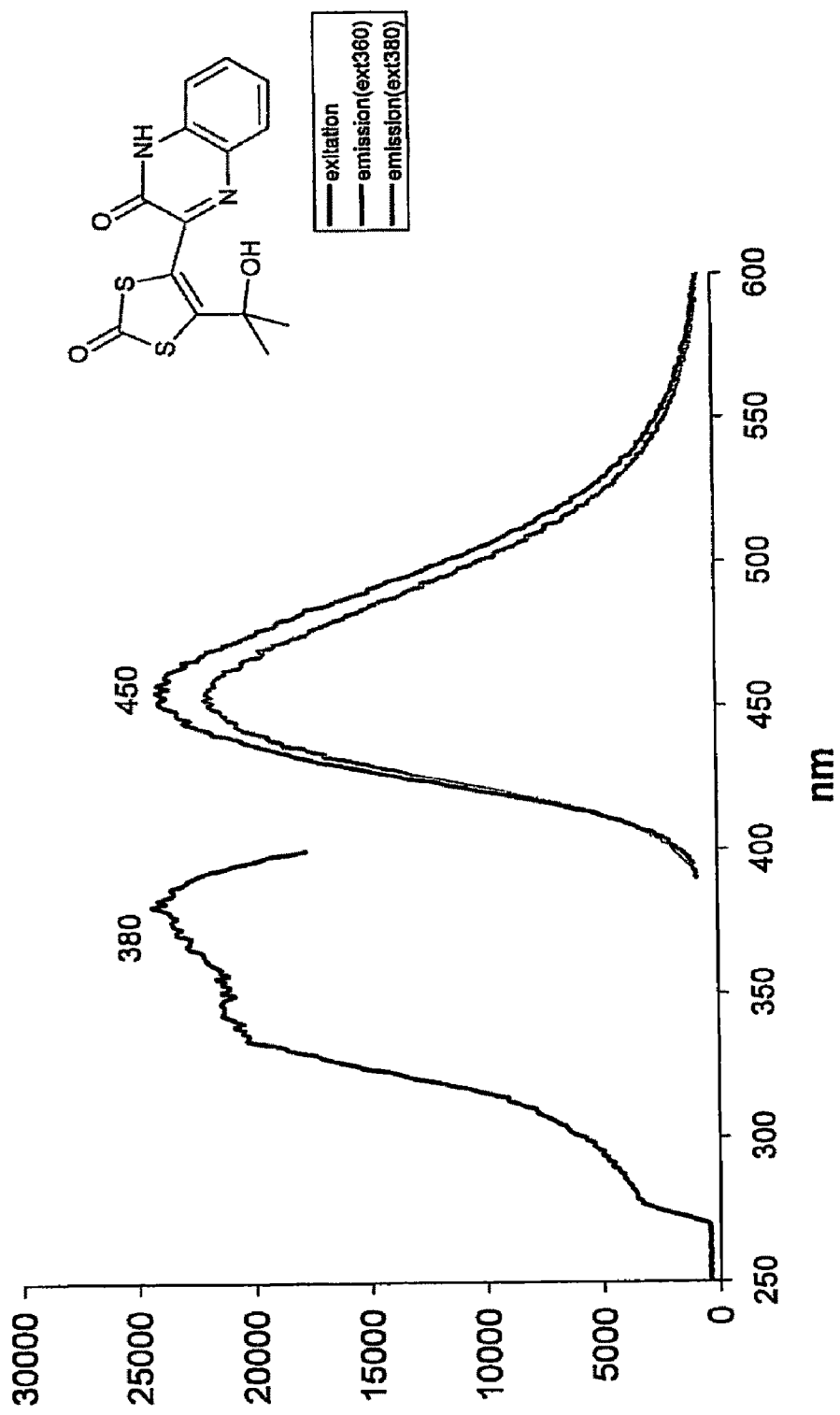
Figure 40:
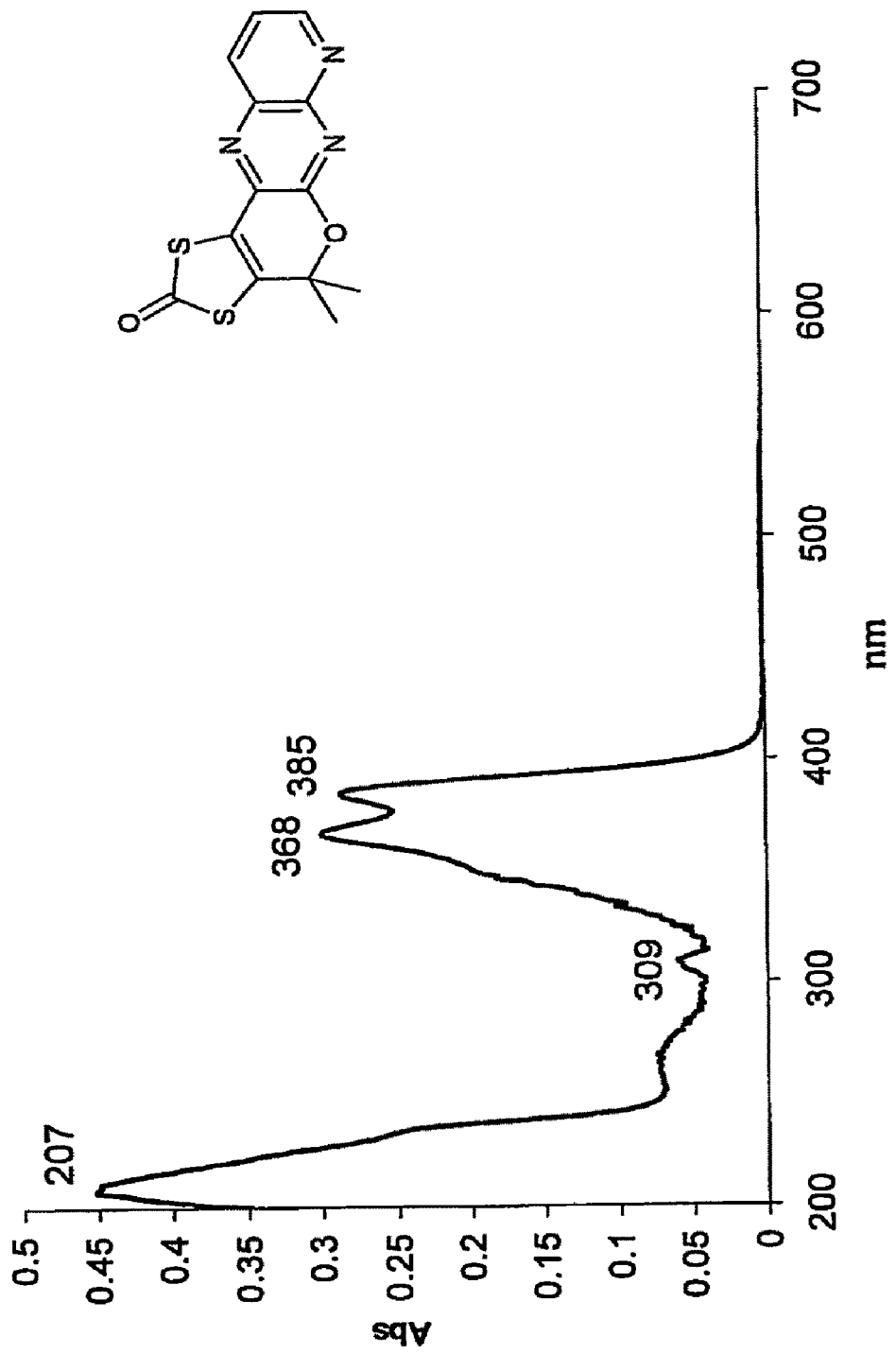
FIGS. 40-41 illustrate electronic spectra and excitation and emission spectra of one fluorophore of the present disclosure.
Figure 41:
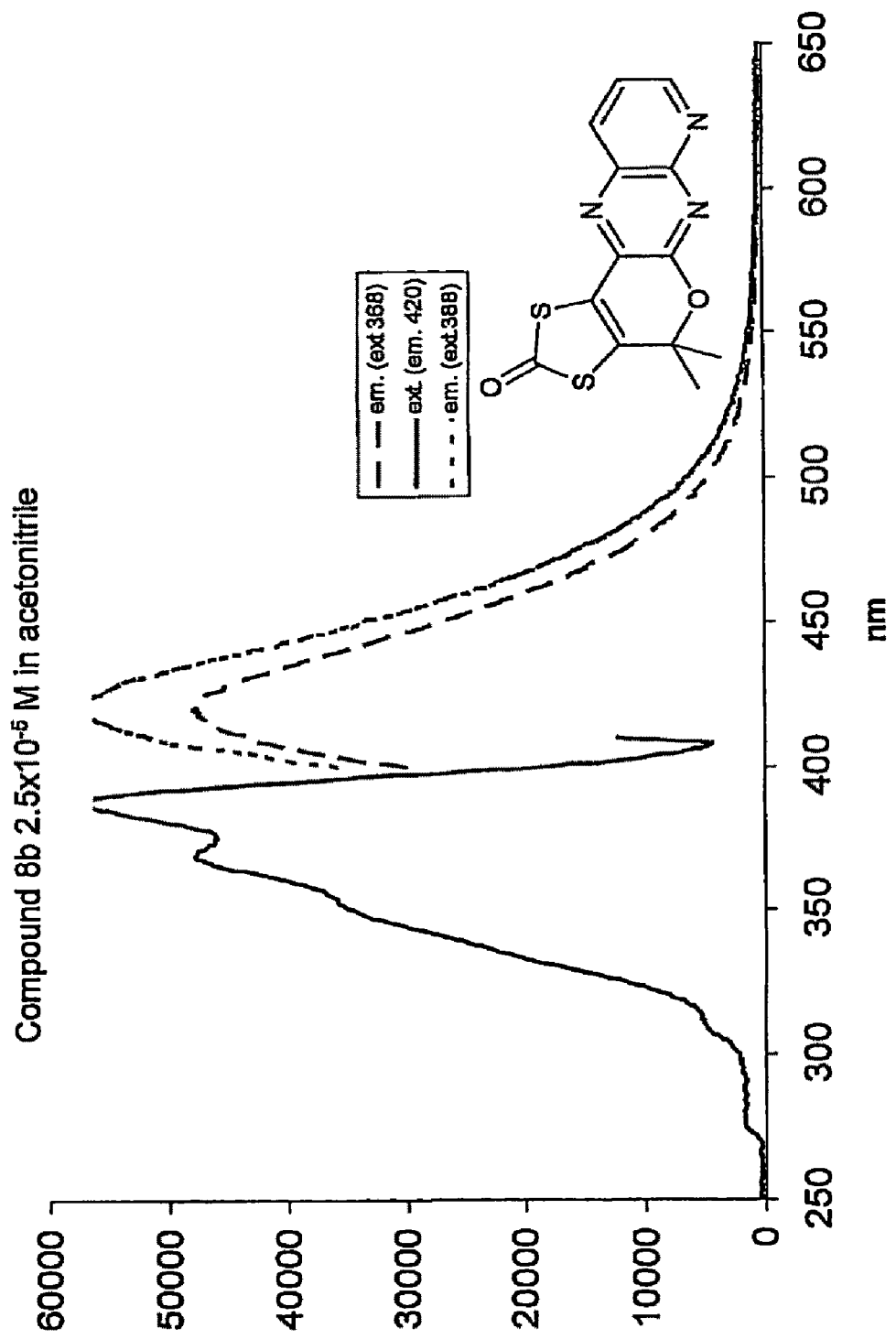
Figure 42:
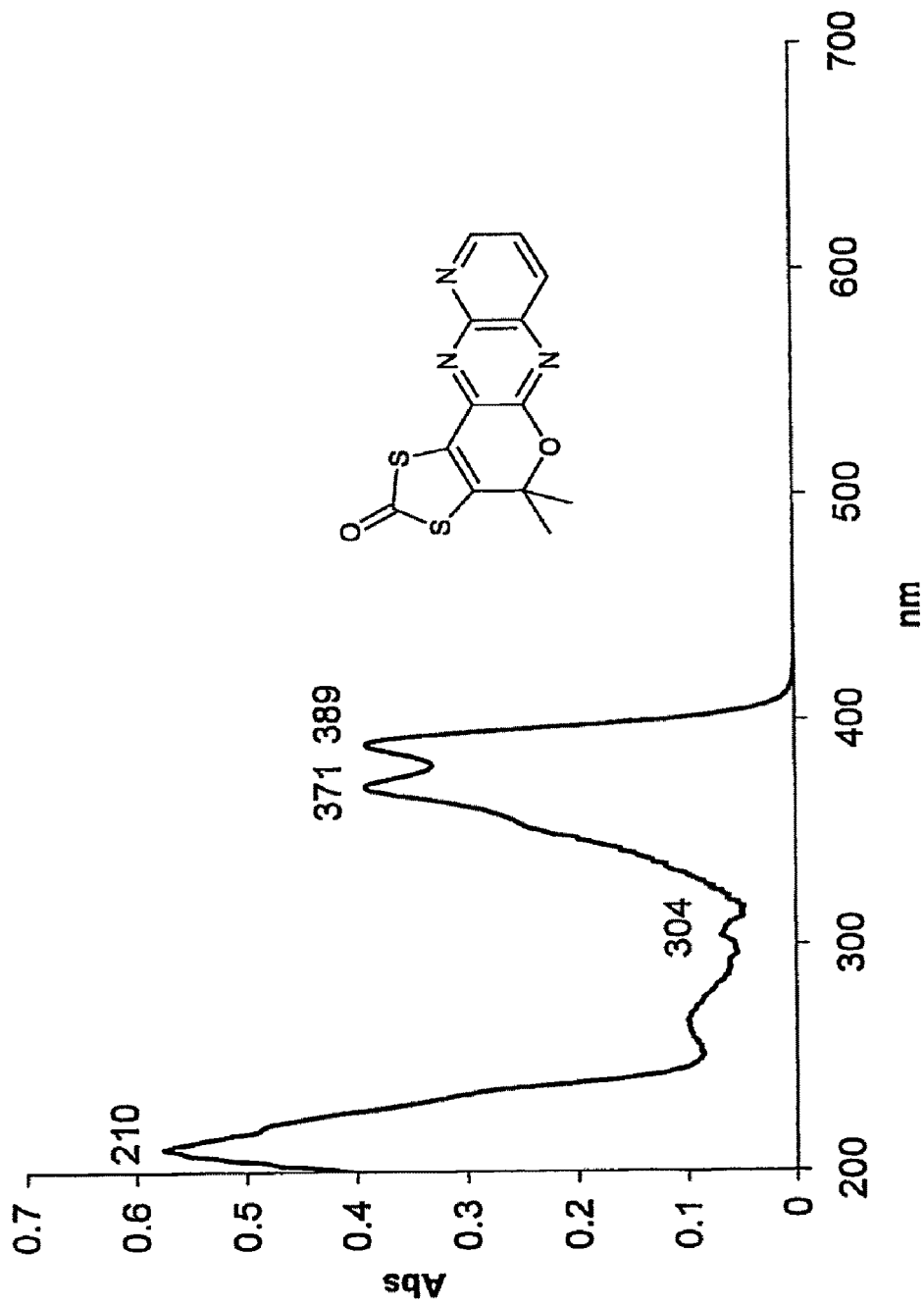
FIGS. 42-44 illustrate electronic spectra and excitation and emission spectra of one fluorophore of the present disclosure.
Figure 43:
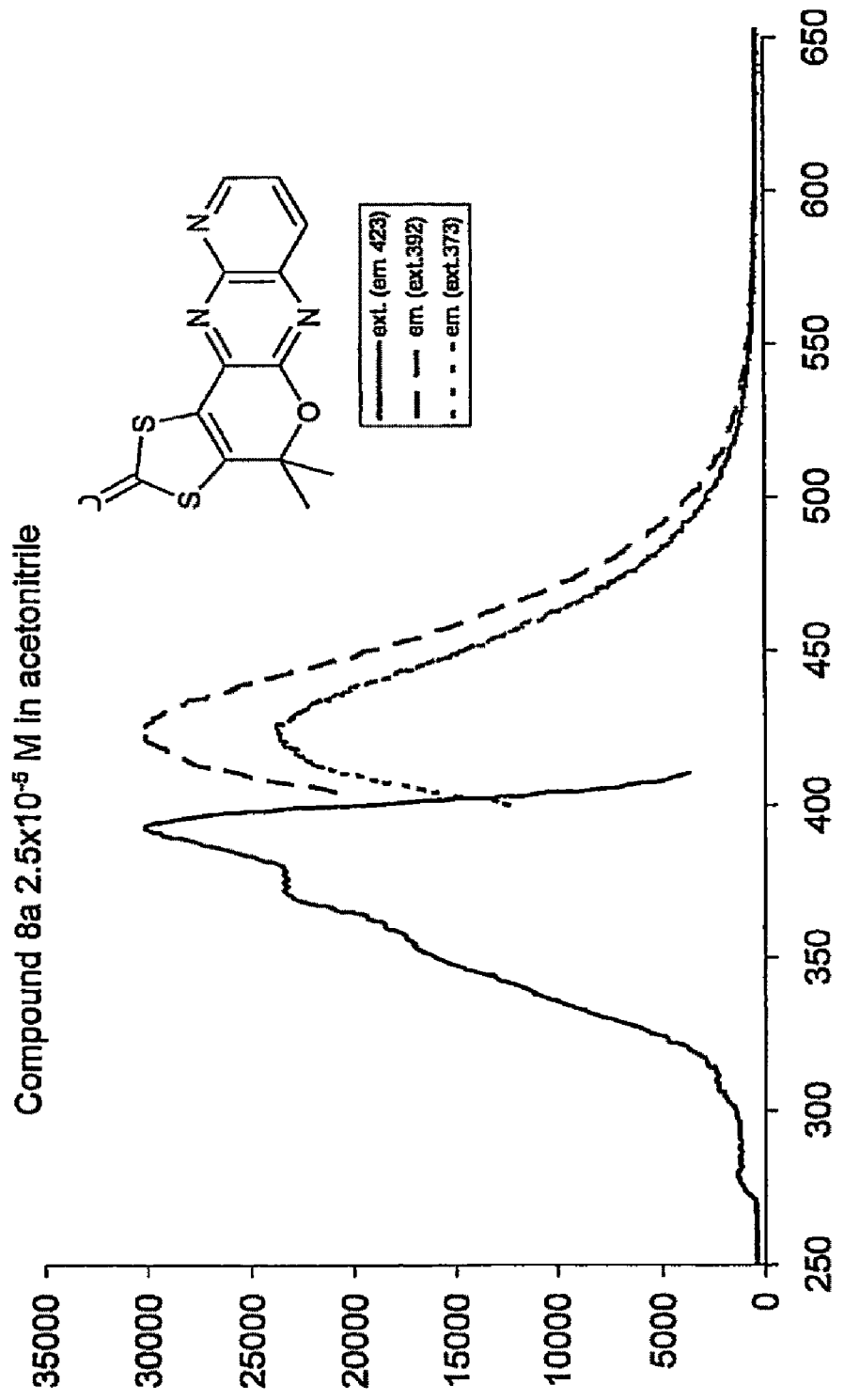
Figure 44:
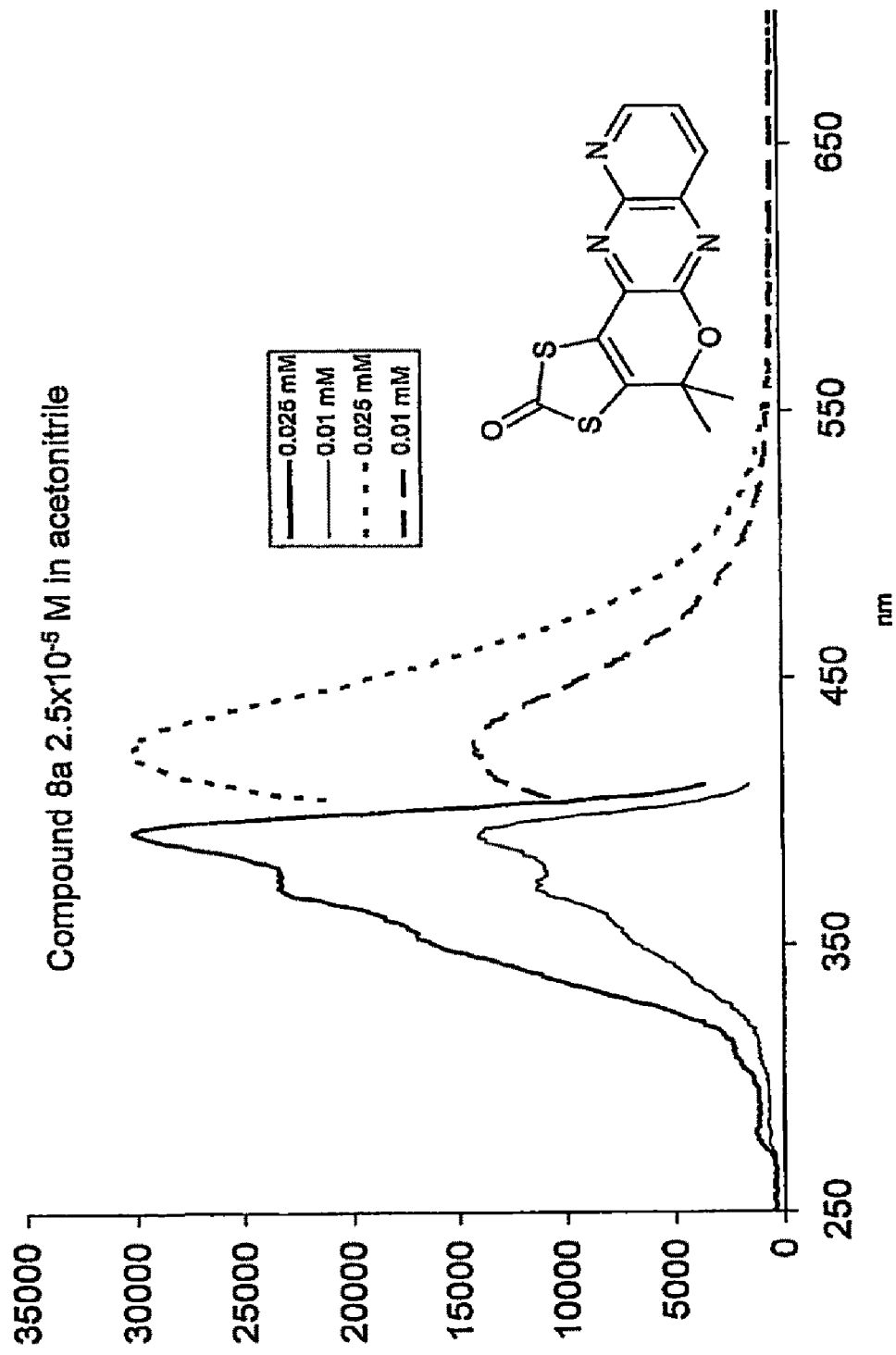
Figure 45:
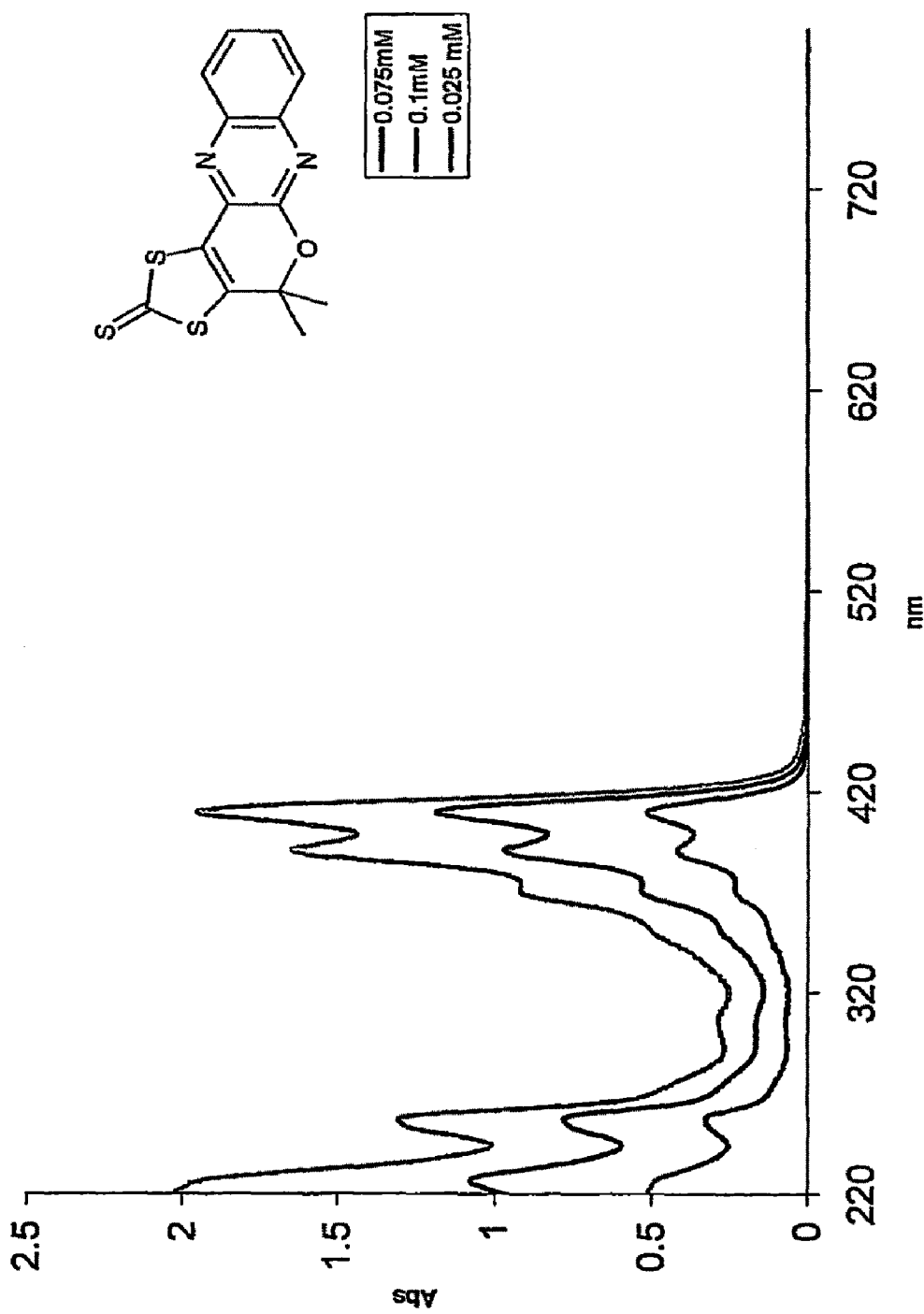
FIGS. 45-46 illustrate electronic spectra and excitation and emission spectra of one fluorophore of the present disclosure.
Figure 46:
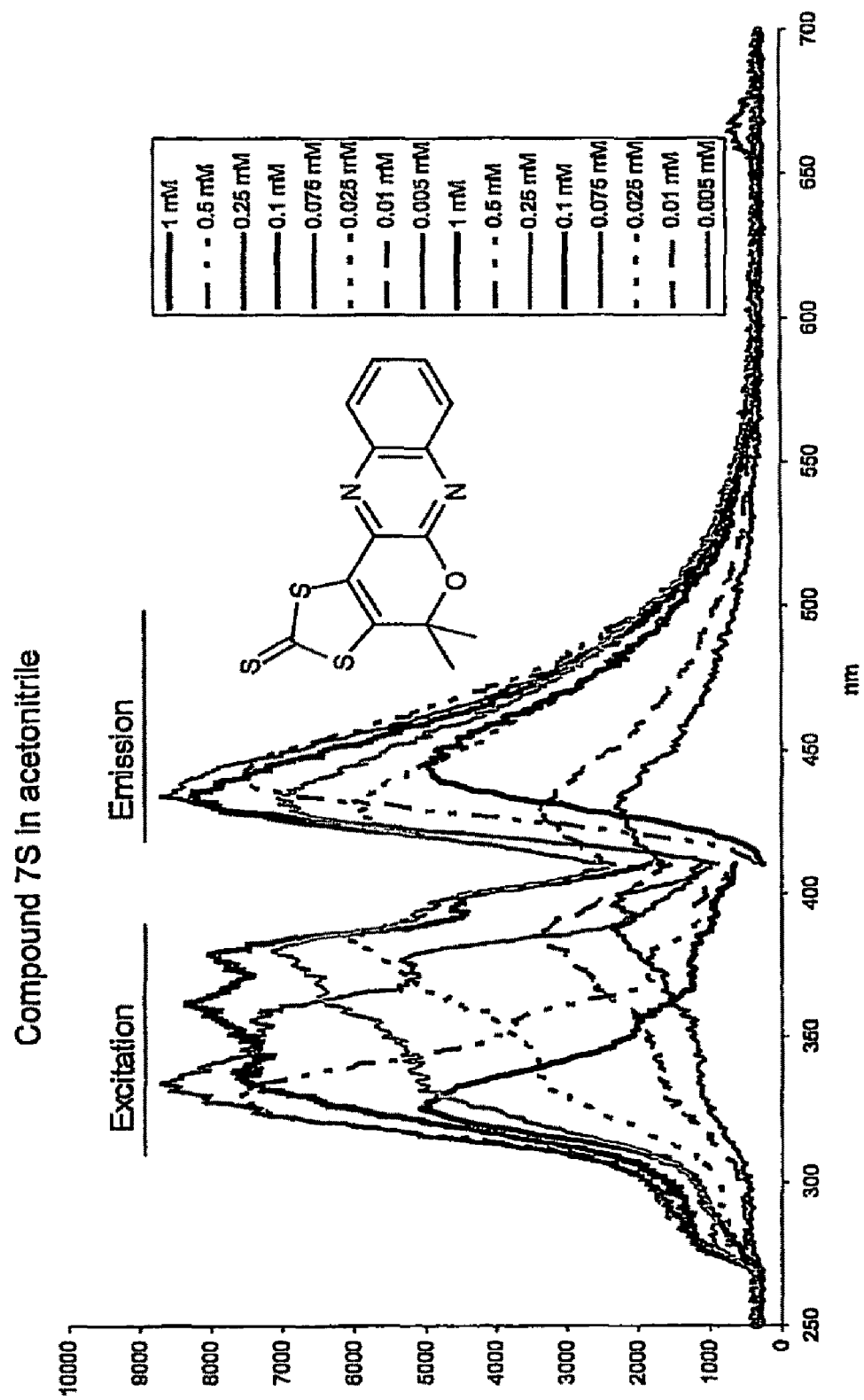
Figure 47:
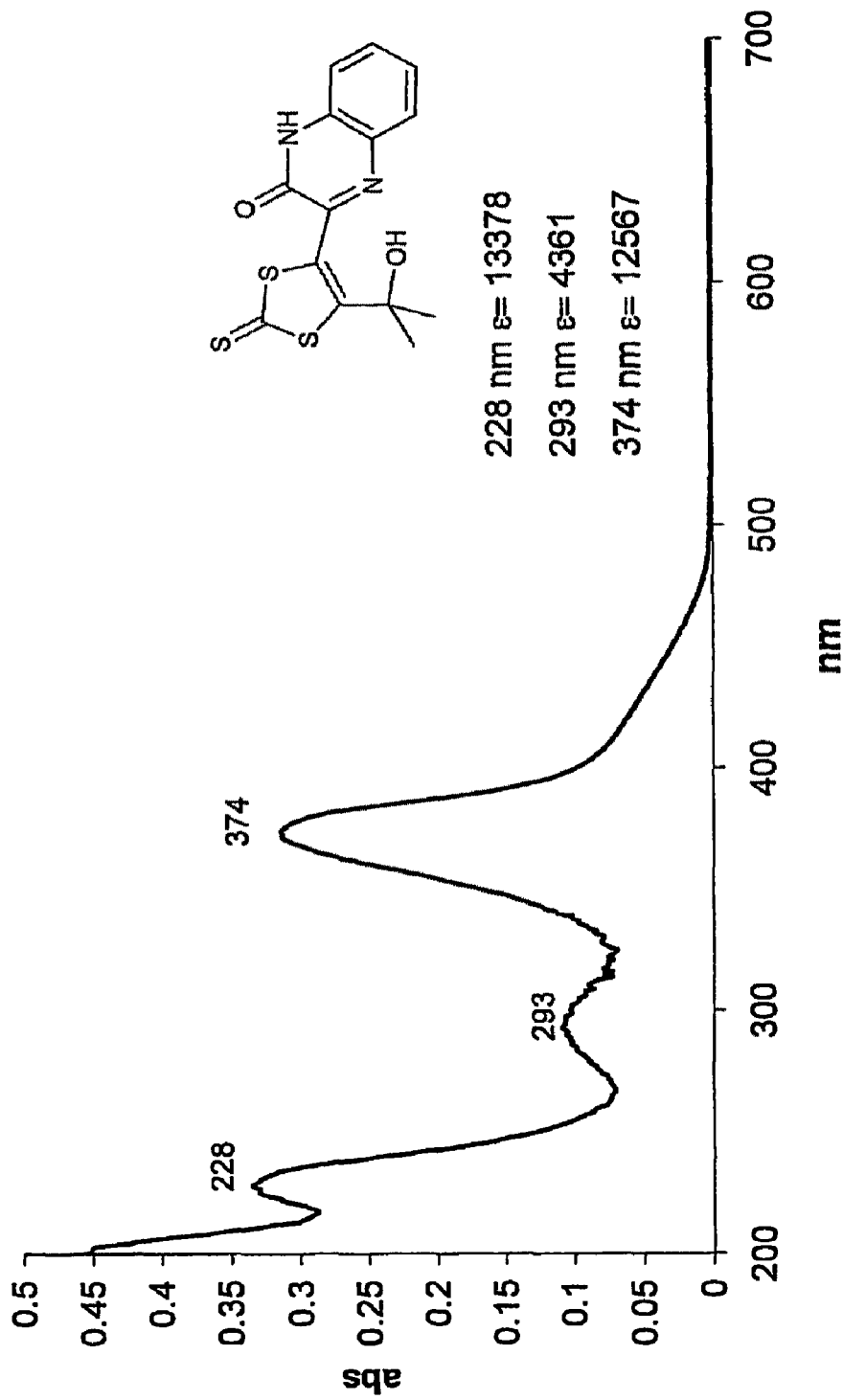
FIGS. 47-48 illustrate electronic spectra and excitation and emission spectra of the open form of one fluorophore of the present disclosure.
Figure 48:
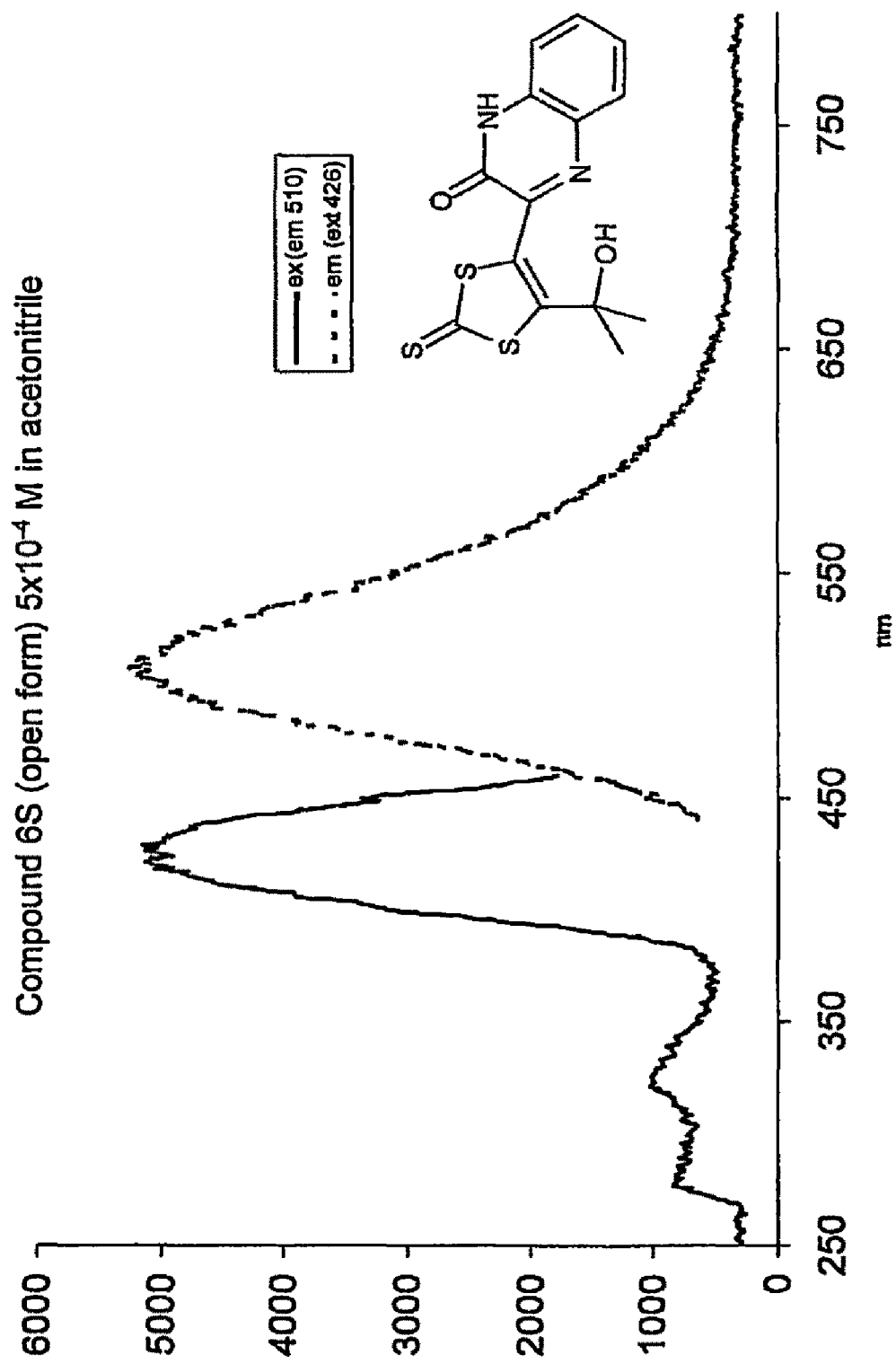

According to other embodiments, the fluorophores of the present disclosure may be used as markers for metal ions, for example, to determine the presence of metal ions (such as a metal sensor). For example, under basic conditions, fluorescence of the fluorophores may be quenched when in the presence of certain transition metal ions. However, in the presence of other closed shell metal ions (such as, for example, $Zn^{2+}$, $Cd^{2+}$, $Hg^{2+}$, and $Pb^{2+}$) the fluorescence of the fluorophores may still be present. In certain embodiments, differential fluorescence wavelengths between complexes of the fluorophores and the metal ions can be used as sensors for such metal ions. For example, fluorophore 7 may be complexed with different metal ions and, depending on the type and charge of the metal ion, have a fluorescent emission of light with a different wavelength according to the complexed metal ion. As can be seen in FIG. 8, significant fluorescence is observed when fluorophore 7 is complexed with $Pb^{2+}$ ions, where the fluorescence is at a wavelength which is different from fluorescence wavelength observed from the other ions. In this example, the $Pb^{2+}$/fluorophore complex fluoresces at a wavelength of ~470 nm, whereas the $Zn^{2+}$/fluorophore complex fluorescence shifts to a higher energy wavelength of ~606 nm after 24 hours of incubation. The structure of the complex of fluorophore 7 and the $Cu^{2+}$, $Ni^{2+}$, and $Mo^{4+}$ is shown in FIG. 11. In certain embodiments, the intensity of the fluorescent emission spectrum of the complex may be determined. According to specific embodiments, the fluorescent emission spectrum of the complex may be qualitatively used to determine the presence of a metal ion in a solution or, alternatively, may be quantitatively used (for example, by the intensity of the emission spectrum) to determine the concentration of the metal ion in the composition. For example, FIG. 12 shows how the intensity of fluorescence varies according to the concentration of the metal/fluorophore complex. Thus, the fluorophores of the present disclosure may be used as potential markers for metal ions.

The fluorophores according to certain embodiments of the present disclosure may be used as a component in an electronic device. For example, the fluorophores of the present disclosure may be used as an organic electronic material. In other embodiments, the fluorophores may be used in a molecular electronic device. For example, the fluorophores of the present disclosure may be used as a component in an LCD (liquid crystal display) screen or organic LED (light emitting diode), for example as a photostable fluorophore having a blue or bluish emission maximum. Non-limiting examples of the use of fluorophores as components of electronic devices are disclosed in PCT Publication No. WO/2004/051616, the disclosure of which is incorporated in its entirety by reference herein.

Figure 2:
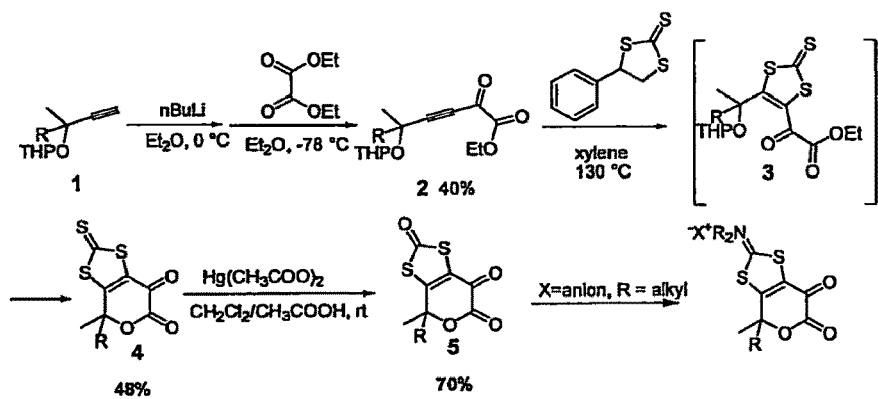
FIG. 2 illustrates a synthetic scheme for the synthesis of an intermediate for the preparation of the fluorophores according to the present disclosure.

According to various embodiments, the fluorophores of the present disclosure may be readily synthesized using organic chemistry techniques. For example, the synthesis of various embodiments of the fluorophores is described herein. It should be noted that the featured embodiments are intended to be exemplary and are in no way limiting to the scope of the fluorophores as described herein. Certain specific examples are discussed in detail in FIGS. 2 through 5, and similar methodologies can be used for synthesizing other fluorophores described herein. As illustrated in FIG. 2, the synthetic approach begins with the protection of the substituted propargyl alcohol with tetrahydropyran protecting group resulting in alkyne 1. The terminal alkyne in compound 1 is then deprotonated with n-butyl lithium and the reaction of the resulting acetylide with diethyl oxalate at a low temperature yields keto ester 2. The presence of an electron-withdrawing group (i.e., the ketone) activates the alkyne functionality toward the reaction with styrene trithiocarbonate to introduce the protected dithiolene moiety. When the reaction was performed neat, the open intermediate 3 was isolated and then transformed to the pyran-dione 4 upon addition of trifluoroacetic acid. Conversely, when the reaction was performed in xylene, the pyran-dione 4 was isolated directly. Next, the dithiolethione functionality may be converted to the dithiolone by treating compound 4 with mercuric acetate. The resulting dithiolone 5 can be converted to an imine or iminium ion, 5a or 5b respectively, by reacting the dithiolone with an appropriate amine. As will be understood by one having ordinary skill in the art, any of compounds 4, 5, 5a, or 5b may be converted to the fluorophore, thereby resulting in variations of X as shown in Formula I.

Figure 3:
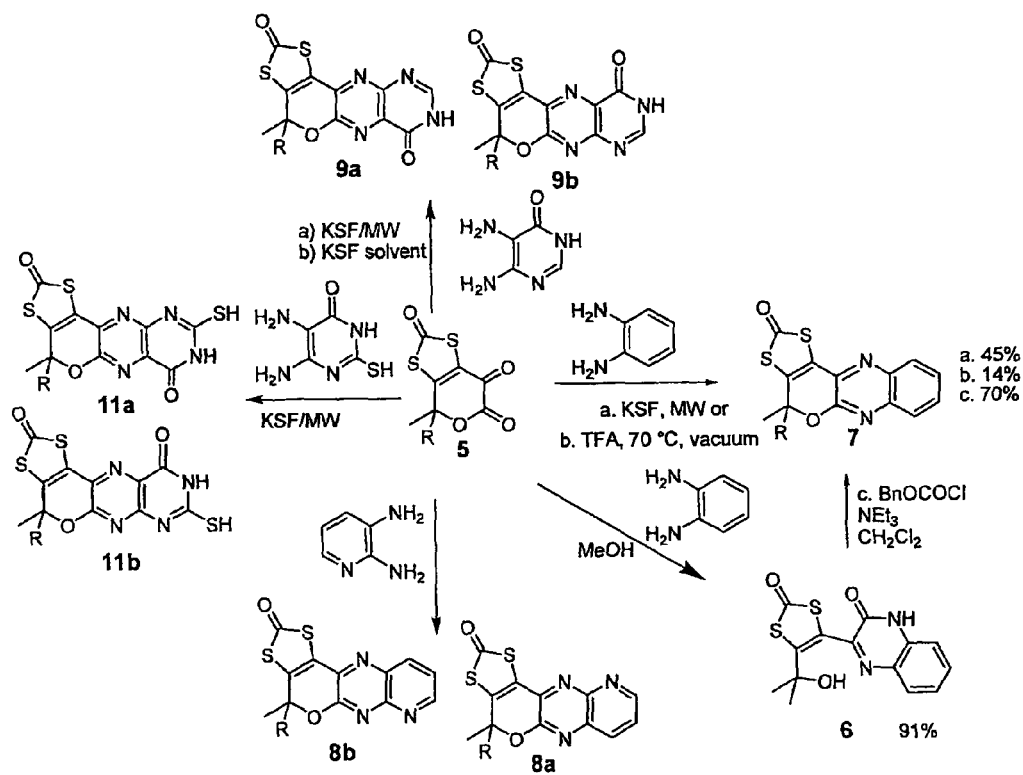
FIGS. 3 through 5 illustrate synthetic schemes for generating fluorophores possessing structurally distinct formulas according to various embodiments of the present disclosure.
Figure 4:
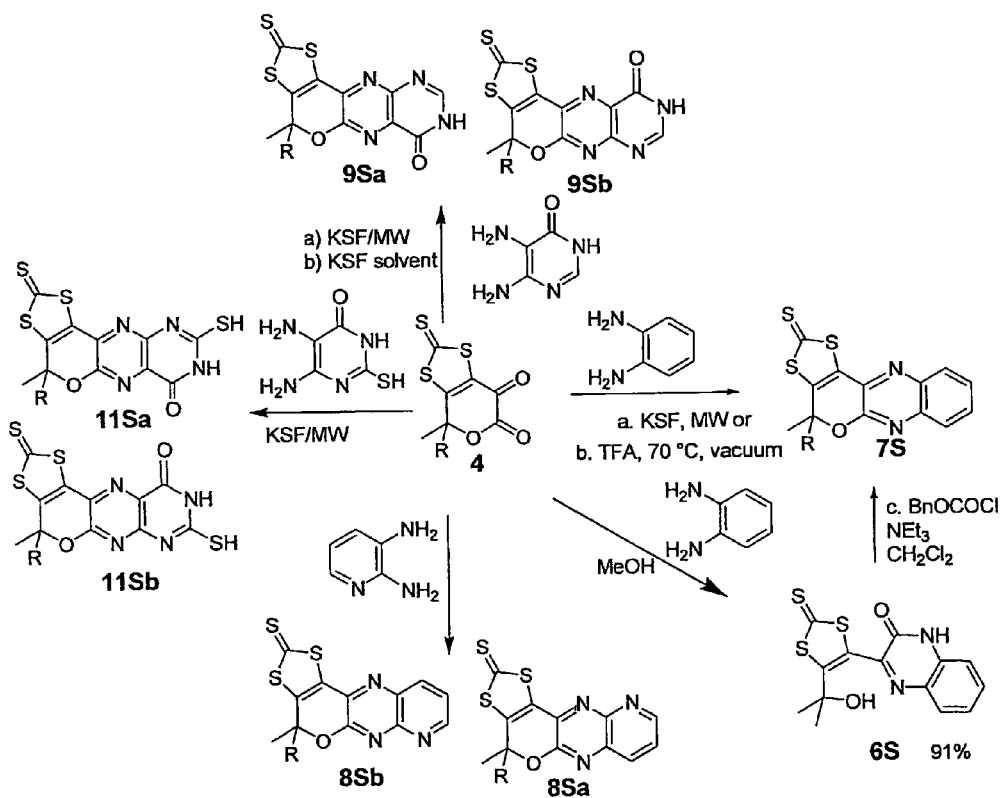
Figure 5:
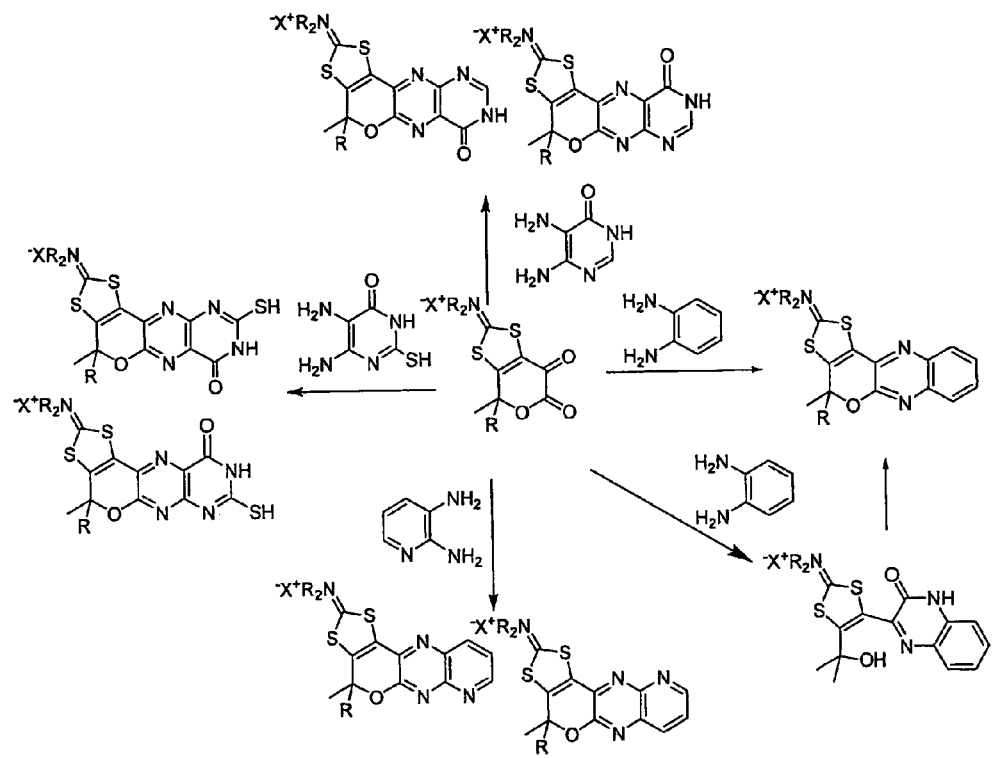

Once the diketo-compounds 4, 5, 5a, or 5b are prepared they may be reacted with a variety of diamines to produce different sets of compounds as desired. The condensation reactions resemble the Isay synthesis of pteridines reported by Isay, O., "Eine Synthese des Purins," *Berichte der deutschen Chemischen Gesellschaft.*, 1906, 39, 250-265, the disclosure of which is incorporated in its entirety by reference herein. The synthetic schemes for such reactions are shown in FIGS. 3-5. The structures of the resulting fluorophores have been confirmed by nuclear magnetic resonance spectroscopy and mass spectrometry, and certain fluorophore structures have been confirmed by X-ray crystallography.

Figure 6:
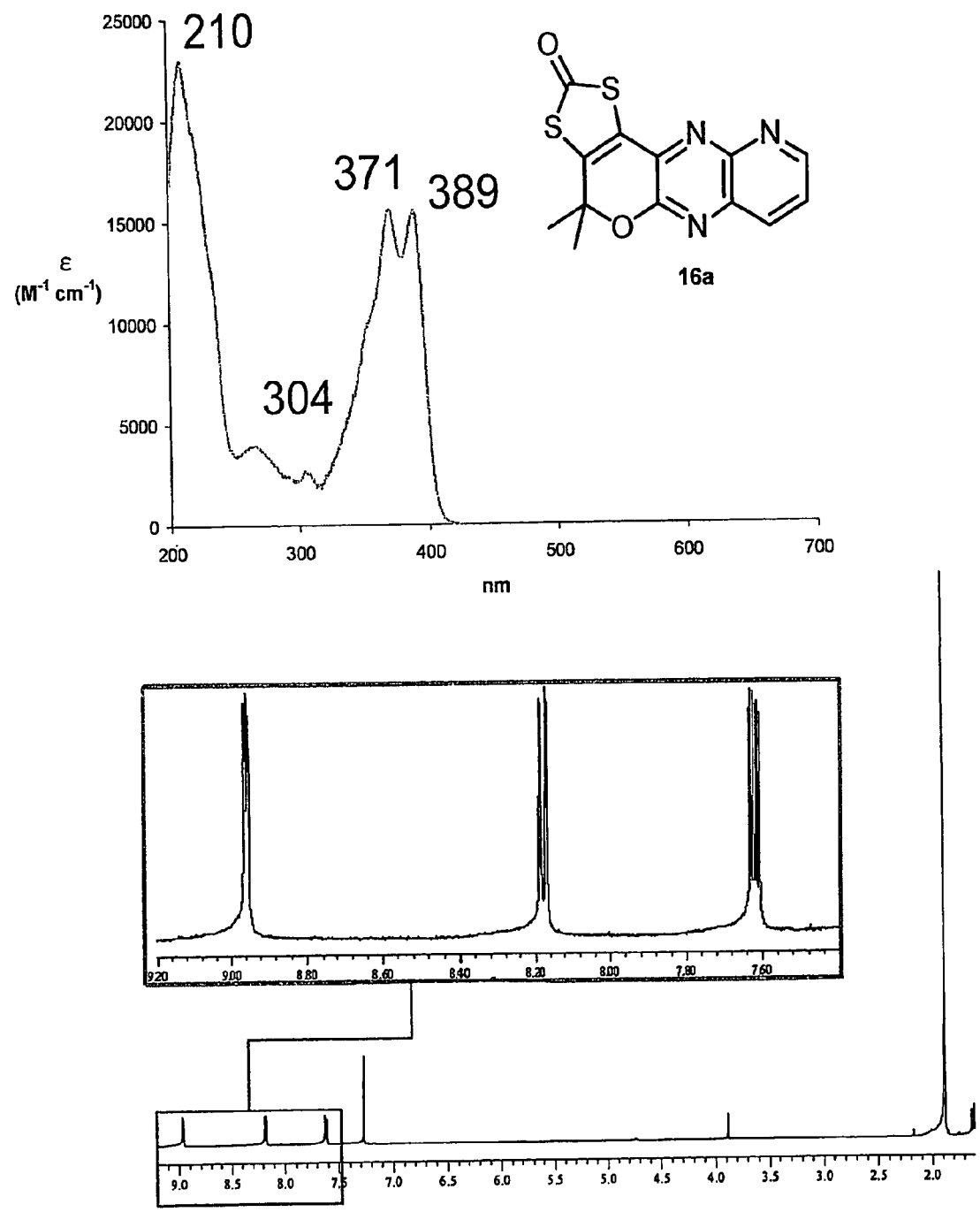
FIGS. 6 and 7 illustrate the electromagnetic absorption spectra and $^1H$ NMR spectra of two embodiments of the present disclosure.
Figure 7:
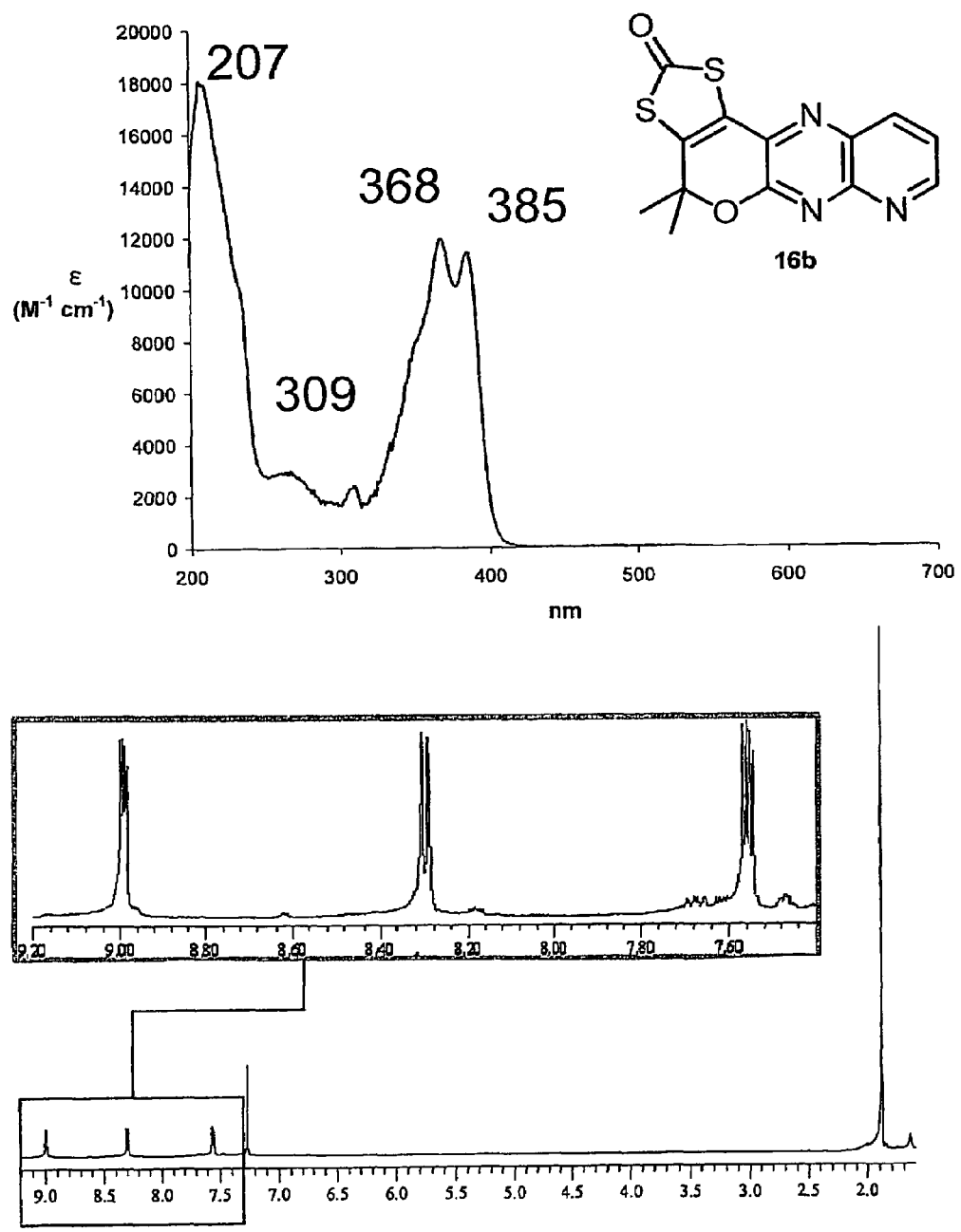

According to one embodiment, diketone 5 (R=methyl) may be condensed with 2,3-diamino pyridine using microwave irradiation ("MW") (equation 1). The resulting pair of isomeric fluorophores may be separated and exhibit different absorption spectrum. The absorption spectra and $^1$H NMR spectra of the two isomeric fluorophores are shown in FIGS. 6 and 7.

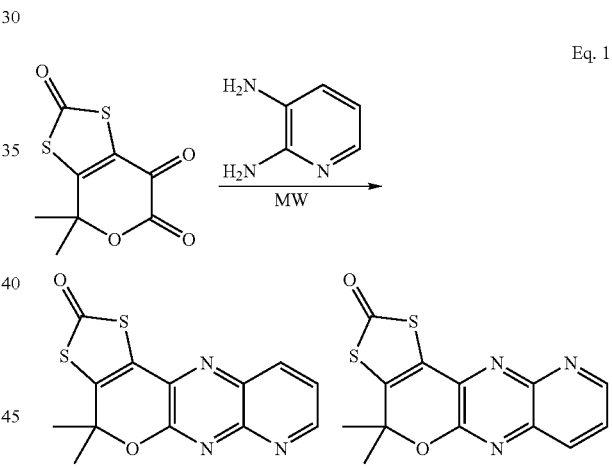

Eq. 1

According to another embodiment, diketone 5 (R=ethyl) may be condensed with 5,6-diamino pyrimidone (R=H) using microwave irradiation ("MW") (equation 2). The resulting two isomeric fluorophores may be separated and exhibit different absorption and fluorescence spectra.

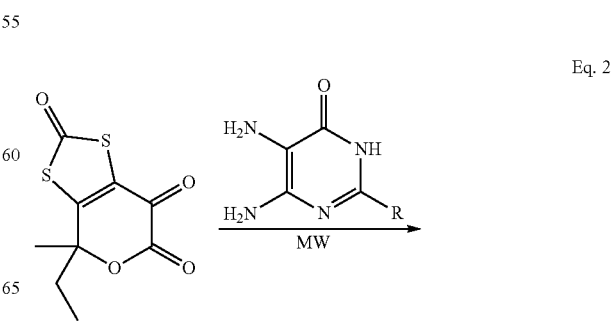

Eq. 2

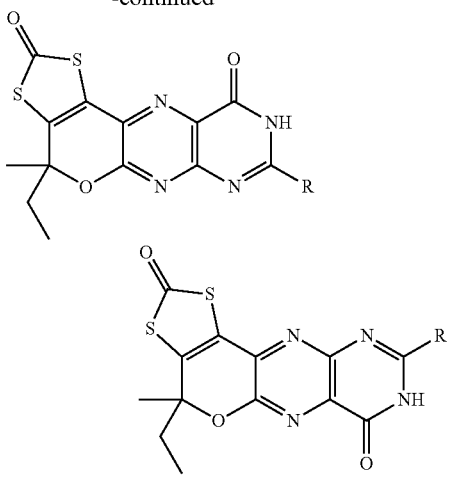

Figure 9:
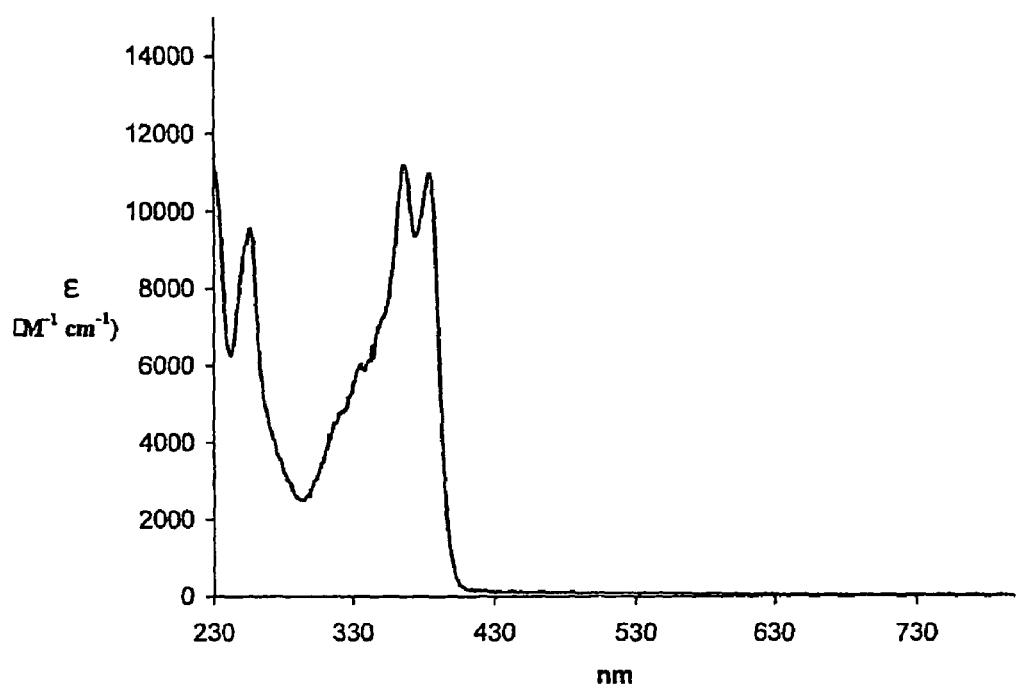
FIG. 9 illustrates the electromagnetic absorption spectrum in methanol of a fluorophore according to the present disclosure.

These fluorophores are soluble in common organic solvents, for example, but not limited to, chloroform, methylene chloride, acetonitrile, and methanol and in mixtures of methanol and water. They exhibit fluorescence properties, with the case of fluorophore 7 as an exemplary example. As shown in FIG. 9, the electronic spectrum of a methanolic solution of fluorophore 7 shows three strong absorption bands at 256 nm, 367 nm, and 385 nm, respectively. There is a shoulder near 330 m and no transition was observed beyond 430 nm. The molar extinction coefficients of these bands are near 10000 or higher. Acetonitrile solutions of fluorophore 7 exhibit very similar spectral features with bands 208 nm, 255 nm, 365 nm, and 383 nm. The spectral features remain unchanged in a mixed solvent such as 2.5% methanol 97.5% water. Fluorophore 7 displays fluorescence, for example, solutions of fluorophore 7 produce blue florescence (that is, emit electromagnetic radiation having a wavelength in the blue region of the visible spectrum) when irradiated with a UV radiation. Fluorophore 7 is stable in acid while in base (i.e., pH>7) it transforms into a less fluorescent substance. Thus, in principle, this compound can be used as a pH sensor. That is, the fluorescence emission intensity may vary according to the pH of the environment or solution that the fluorophore is in.

Figure 10:
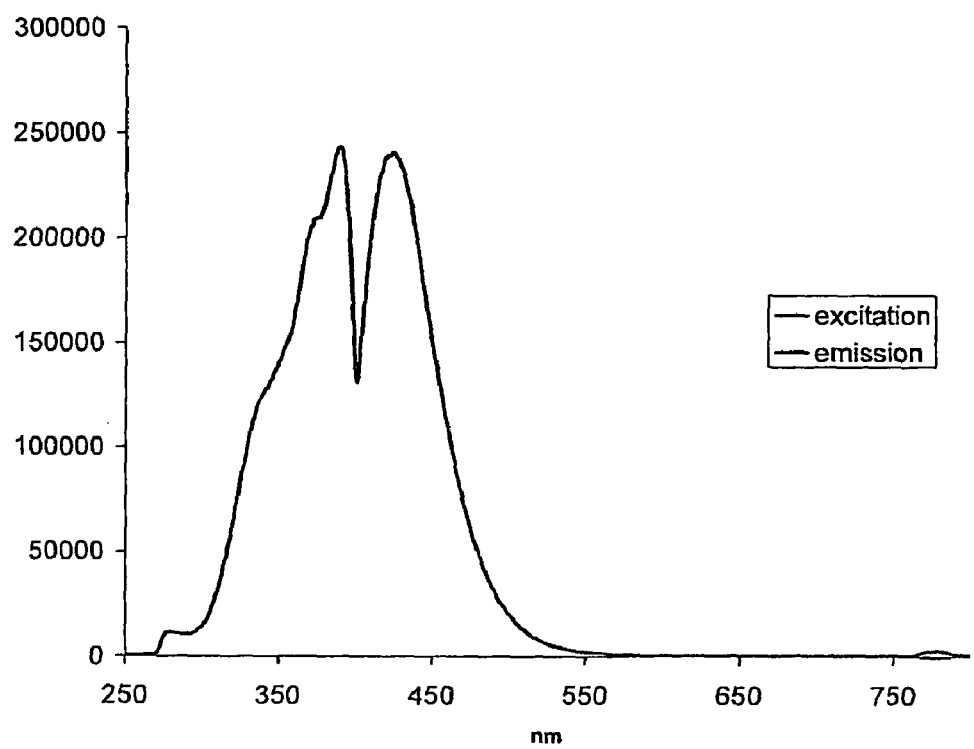
FIG. 10 illustrates the electromagnetic absorption/excitation spectrum and the fluorescence emission spectrum in a mixed solvent system of a fluorophore according to the present disclosure.

Fluorophore 7 exhibits strong fluorescence in acetonitrile as solvent, in methanol as solvent, and in the methanol-water mixed solvent. For an acetonitrile solution of fluorophore 7, when excited at 366 mm or 384 nm band, an emission at 411 nm is observed. Similarly when a methanolic solution of fluorophore 7 is excited at 385 nm or 367 nm, an emission at 415 nm is observed. Finally for a solution of fluorophore 7 in the mixed solvent, when excited at 389 nm, an emission is observed at 423 nm (see FIG. 10). A 0.12 value for the quantum yield of fluorophore 7 in methanol was determined in reference to fluorescein in 0.1 M NaOH ($\phi$=0.95) (using the procedure reported by Brannon, et al., *J. Phys. Chem.* 1978, 82, 705). Fluorophores of the present disclosure are further described in U.S. application Ser. No. 12/020,343, filed Jan. 25, 2008, the disclosure of which is incorporated in its entirety by this reference.

Specific Binding and Detection of Lead in Samples

In one specific embodiment of the present disclosure, a fluorescing detector for lead ions in samples, such as, but not limited to, aqueous environmental and other water samples, is disclosed. As discussed herein, lead poisoning leads to significant developmental problems in children, resulting in neurological, reproductive, cardiovascular, and other developmental damage. As a result, the EPA has set limits for the exposure to lead in the environment (for example, the upper limit for lead in drinking water is currently set at 15 ppb). Current methods of quantifying $Pb^{2+}$ in environmental samples may require expensive instrumentation, are not readily portable and are restricted to in vitro measurement. The presently disclosed compounds, lead sensors and methods provide cost effective, portable, rapid and reliable methods for detecting and quantifying lead content in samples that are also highly sensitive and selective for lead over other metal ion contaminants. In addition, the lead binding fluorophore is water soluble and also may be cell permeable and thus has the potential for detecting lead contamination in environmental and cellular applications. Further details regarding the fluorescing detector for lead ions are disclosed in *Angewante Chemie International Edition*, 2009, 48, 3996-3998, the disclosure of which is incorporated in its entirety by this reference.

It has been discovered that one embodiment of the novel fluorophores disclosed herein provides for a highly sensitive and specific binder for $Pb^{2+}$ ions. Accordingly, this embodiment of the present disclosure provides for a fluorescent binder of $Pb^{2+}$ ions. The fluorescent binder has a structure represented in its protected form by Formula IV below.

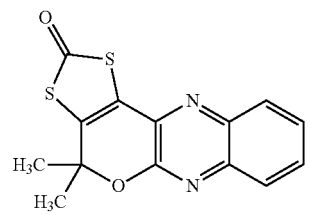

IV

Formula IV may be also be represented by Formula I (where X is O, $R^1$ and $R^2$ are each methyl, and $R^3$ and $R^4$ come together to form a benzo ring) or Formula II (where X is O, $R^1$ and $R^2$ are each methyl, and the benzo ring is unsubstituted with n=0). According to this embodiment, the structure represented by Formula IV may be hydrolyzed, for example by acid or base hydrolysis, including, for example, hydrolysis with $Et_4NOH$, to form the active fluorescent binder which binds to $Pb^{2+}$ to form a highly fluorescent complex. The active fluorophore compound is believed to have a structure represented by Formula V:

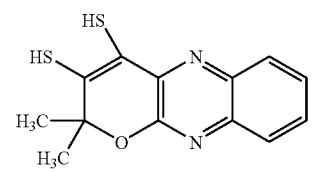

V or the corresponding thiolate compound (i.e., where one or both thiols of the ene-dithiol are deprotonated). In the presence of $Pb^{2+}$ ions and a hydrolyzing agent, the dithiocarbonate functionality of compound IV may be hydrolyzed and the resulting fluorescent binder compound binds with the $Pb^{2+}$ to form a $Pb^{2+}$/binder complex. According to specific embodiments, the fluorescent binder of the present disclosure has a high sensitivity for $Pb^{2+}$ ions, even in the presence of other metal ions. For example, in one embodiment, the fluorescent binder has a sensitivity for $Pb^{2+}$ as measured by apparent dissociation coefficient, $K_d$ (as determined by measuring the fluorescence of the complex and according to the procedure in He et al., *J. Am. Chem. Soc.*, 2006, 128, 9316) that may be less than 500 nanomolar (nM). In other embodiments, the $K_d$ may be less than 300 nM, or in certain embodiments less than 250 nM. In specific embodiments, the fluorescent binder may have a sensitivity for $Pb^{2+}$ at $K_d=217$ nM at pH=10. As will be understood by one of ordinary skill in the art, the $K_d$ for binding of $Pb^{2+}$ may vary according to the conditions of the experiment, including, but not limited to solvent, temperature, pH, etc. It should be noted that in other embodiments, other compounds represented by Formula I may also serve as selective binders of lead, or other metal ions.

Figure 49:
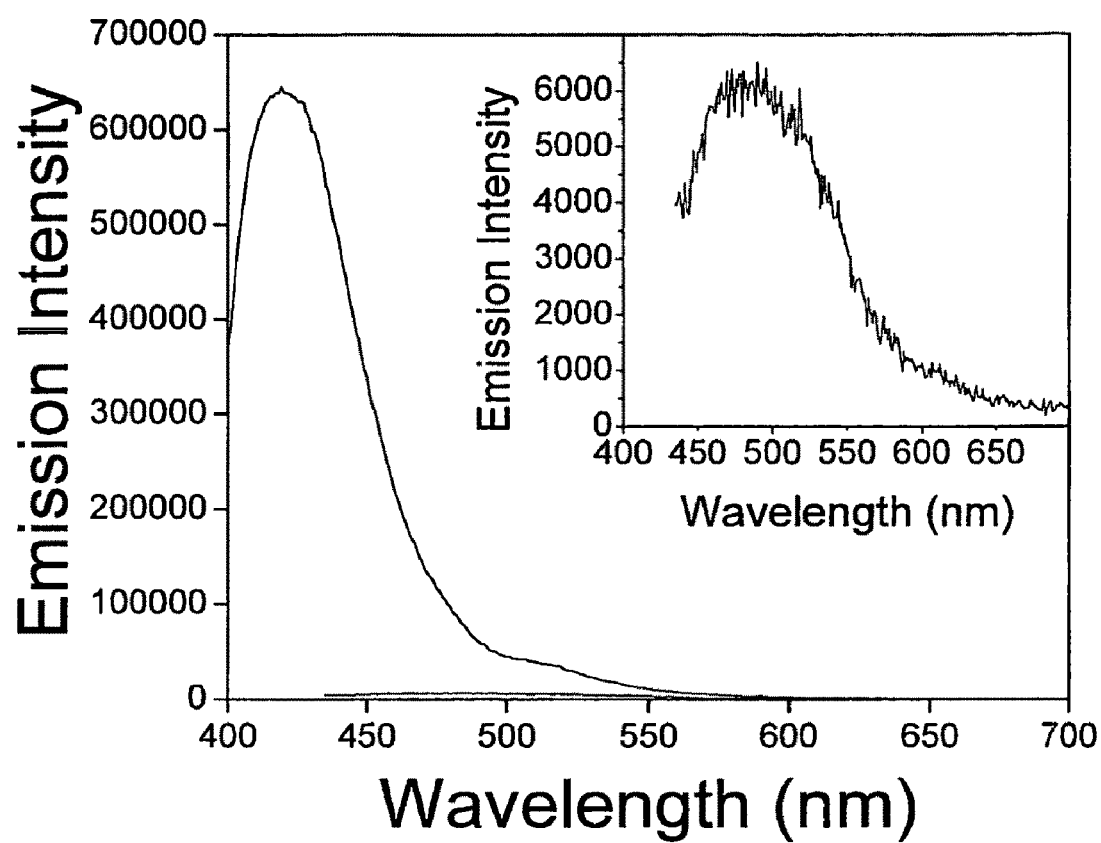
FIG. 49 illustrates the emission spectrum of free fluorophore compared to the emission spectrum of the complex formed by the fluorophore and $Pb^{2+}$.

When the fluorescent binder according to the present embodiments binds with $Pb^{2+}$ to form a $Pb^{2+}$/binder complex, the complex fluoresces with a high optical brightness. For example, according to the present embodiments, the unbound fluorescent binder represented by Formula V (or Formula IV, in its protected form) may have an excitation band with a absorbance maximum $\lambda_{max}$ at a wavelength centered around 415 nm, an emission band with a emission maximum $\lambda_{max}$ centered around 465 and a quantum yield for the fluorescence emission of $\phi=0.12$. When the fluorescent binder is bound to $Pb^{2+}$ ions, the resulting $Pb^{2+}$/binder complex may have an excitation band with a $\lambda_{max}$ centered around 389 nm, an emission band with a $\lambda_{max}$ centered around 423 nm, and a quantum yield of $\phi=0.63$. Quantum yields were calculated with reference to the quantum yield of fluorescein ($\phi=0.95$). As reported herein, the wavelength band for excitation and emission of the unbound fluorescent binder and the $Pb^{2+}$/binder complex may have excitation and emission λmax values that vary by plus or minus 50 nm (i.e., the unbound fluorescent binder may have an excitation band with a $\lambda_{max}$ value ranging from 365 nm to 465 nm and an emission band with a $\lambda_{max}$ value ranging from 415 nm to 515 nm; and the bound fluorescent binder complex may have a excitation band with a $\lambda_{max}$ value ranging from 339 nm to 439 nm and an emission band with $\lambda_{max}$ value ranging from 373 nm to 473 nm). Referring now to FIG. 49, the intensity of an emission spectrum of unbound fluorescent binder (Formula V) (at 5 micromolar (µM) unbound binder, maximum intensity of ~6000 counts/second at $\lambda_{max}$ centered around 465 nm, see inset in FIG. 49) is compared to an emission spectrum of the $Pb^{2+}$/binder complex (at 5 µM of the $Pb^{2+}$/binder complex at a ratio of $Pb^{2+}$ to binder to $Et_4NOH$ of 1:2:4, maximum intensity of ~640,000 counts/second at $\lambda_{max}$ centered around 423 µm). FIG. 49 demonstrates that the $Pb^{2+}$/binder complex fluoresces at a significantly greater intensity (approximately greater than two orders of magnitude) and different wavelength than the unbound fluorescent binder. The examples illustrated by FIG. 49 display a 1:2 ratio of $Pb^{2+}$ to fluorescent binder, while not intending to be limited by any assumed structure, the inventors believe that the stoichiometry of the $Pb^{2+}$/binder complex may be more similar to a cluster of $Pb^{2+}$ ions and fluorescent binder molecules. The ligand to lead ratio in the complex may change depending on the conditions used.

Figure 50:
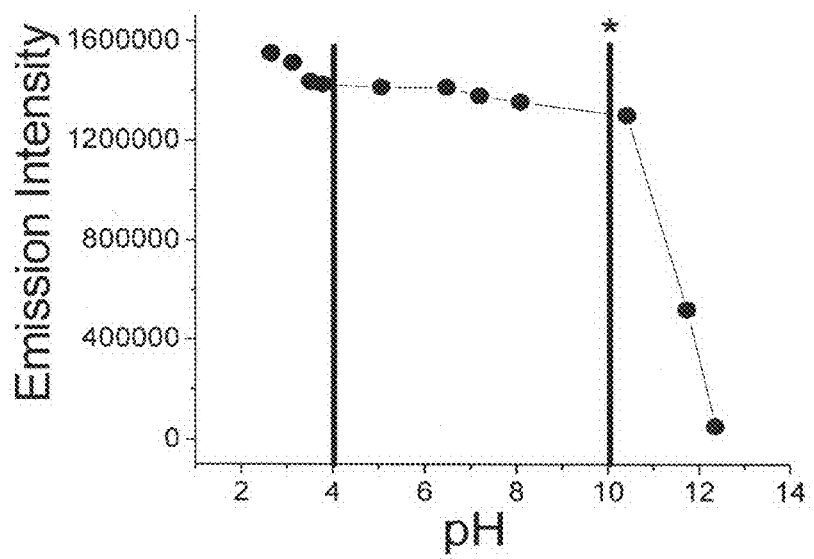
FIG. 50 illustrates the pH profile of $Pb^{2+}$ bound with the fluorophore.

Both the unbound fluorescent binder and the $Pb^{2+}$/binder complex are soluble in aqueous solution making the system suitable for measuring lead ion concentrations in aqueous samples, aqueous extractions or in vitro and in vivo cellular applications. In addition, the $Pb^{2+}$/binder complex fluoresces with greater emission intensity over a wide pH range in aqueous solutions. According to one embodiment the $Pb^{2+}$/binder complex fluoresces with a high fluorescence emission intensity, for example with a quantum yield of greater than 0.5 ($\phi>0.5$), at pH values of 10 or less. For example, under certain conditions the $Pb^{2+}$/binder complex fluoresce with an emission intensity of greater than 1,200,000 counts/sec (for fluorescent species concentration as shown in Example 4) at pH values of 10 or less. One of ordinary skill in the art will recognize that emission intensity may be dependent on experimental factors such as, but not limited to, concentration of the fluorescent species. Thus, the term "high fluorescence emission intensity" means a fluorescence emission intensity having a quantum efficiency of greater than 0.5 ($\phi>0.5$ as measured relative to a fluorescein reference). At pH values of greater 10, the $Pb^{2+}$/binder complex may still have a suitable emission intensity up to pH of about 11.5. Referring now to FIG. 50, a plot of the fluorescence emission intensity vs. pH demonstrates that the $Pb^{2+}$/binder complex fluoresces with a high emission intensity at pH values of 10.5 or less, or at values of 1,200,000 counts/sec at pH values of 10 or less, or alternatively at pH values ranging from about 4 to about 10. With other fluorophores, the fluorescence emission intensity of the fluorophore may decrease at low pH levels. For comparison, as discussed herein, the quantum yield for fluorescence emission of fluorescein decreases at pH levels less than ~8.

Figure 51:
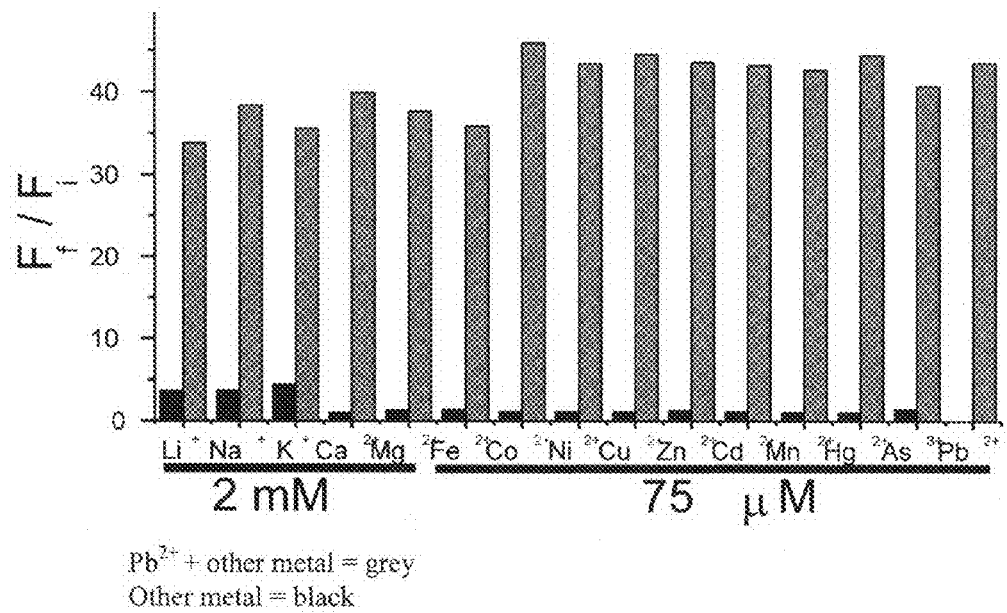
FIG. 51 illustrates the fluorescence emission intensity of the fluorophore in a mixture of $Pb^{2+}$ and other metal ions.

According to certain embodiments, the fluorescent binder discussed herein selectively binds to $Pb^{2+}$ over other metal ions including other transition metal ions. According to various embodiments, the fluorescence emission intensity of the $Pb^{2+}$/binder complex is greater than a fluorescence emission intensity of other metal ion/binder complexes. Other metal ions that may form a metal ion/binder complex that has a lower fluorescence emission intensity than that of the $Pb^{2+}$/binder complex include, but are not limited to $Li^+$, $Na^+$, $K^+$, $Ca^{2+}$, $Mg^{2+}$, $Fe^{2+}$, $Co^{2+}$, $Ni^{2+}$, $Cu^{2+}$, $Zn^{2+}$, $Cd^{2+}$, $Mn^{2+}$, $Hg^{2+}$, $Sn^{2+}$, $As^{3+}$, and mixtures thereof. For example, according to one non-limiting embodiment, the $Pb^{2+}$/binder complex in the presence of the other metal ions may have a fluorescence emission intensity at least about 10 times greater than the fluorescence emission intensity of another metal ion/binder complex. In other embodiments, the $Pb^{2+}$/binder complex in the presence of the other metal may have a fluorescence emission intensity at least about 20 times greater than the fluorescence emission intensity of another metal ion/binder complex. FIG. 51 compares the fluorescence emission intensity of the $Pb^{2+}$/binder complex in the presence of the other metal with the fluorescence emission intensity of the other metal ion/binder complexes (i.e., in the absence of $Pb^{2+}$). As shown in FIG. 51, ions other than $Pb^{2+}$ have little effect on the fluorescence emission intensity of the $Pb^{2+}$/binder complex and when in the presence of $Pb^{2+}$ and another metal ion, the fluorescent binder appeared to be selective for $Pb^{2+}$. Since the $Pb^{2+}$/binder complex fluoresces with a significantly greater intensity than other metal ion/binder complexes, the fluorescent binder may serve as a selective detector for lead ions in various samples, such as, aqueous samples including environmental samples, including samples that may contain other metal ions.

Figure 52:
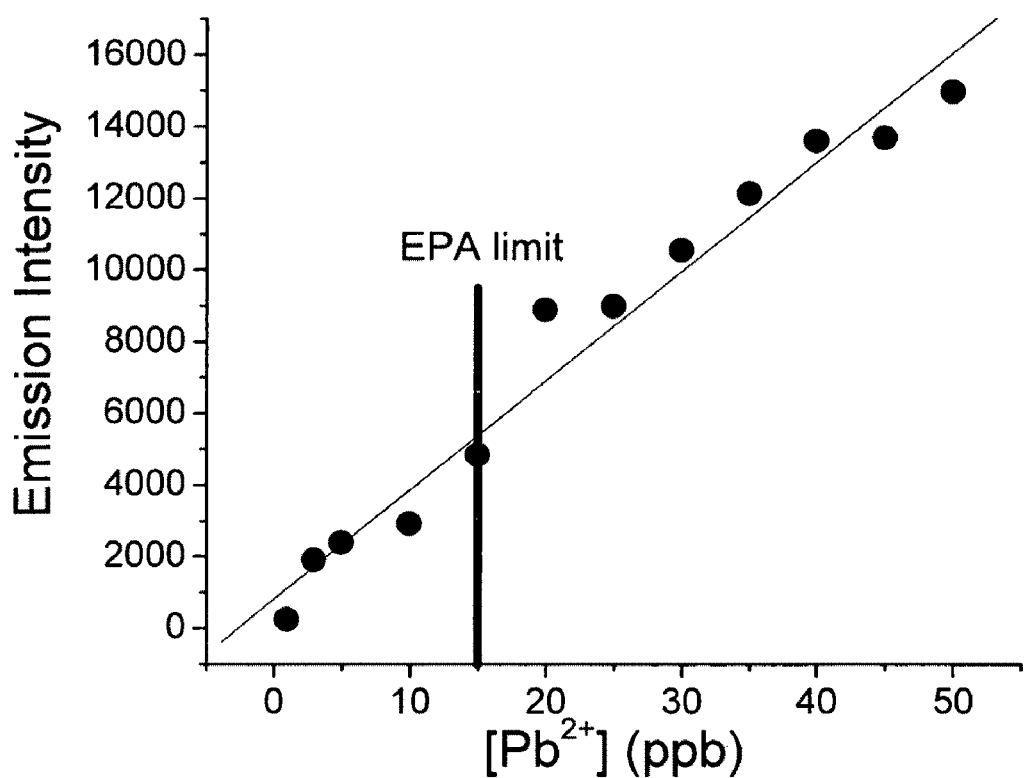
FIG. 52 illustrates a comparison between fluorescence emission intensity of a fluorescent binder complex with $Pb^{2+}$ versus $Pb^{2+}$ concentration (ppb).

In one embodiment, the fluorescent binder may be used to determine the $Pb^{2+}$ ion concentration in water samples. As illustrated in FIG. 52, a calibration plot was established using 10 µM of the fluorescent binder and plotting the fluorescence emission intensity values of the $Pb^{2+}$/fluorophore complex (Y axis, counts/second) versus $Pb^{2+}$ ion concentration (X axis, ppb). Using this calibration plot, the EPA limit for lead in drinking water (15 ppb), as measured by the $Pb^{2+}$/binder complex fluorescence emission intensity has a fluorescence emission intensity of approximately 5,500 counts/sec. Four water samples (a river water sample and three domestic water samples taken from different sources) were tested for lead contamination and showed the following $Pb^{2+}$ ion concentrations: a) a sample of river water was determine to have a $Pb^{2+}$ concentration of 41.5 ppb (±3.4); b) domestic water sample 1 was determined to have a $Pb^{2+}$ concentration of 30.5 ppb (±2.7); c) domestic water sample 2 was determined to have a $Pb^{2+}$ concentration of 11.6 ppb (±1.4); and domestic water sample 3 was determined to have a $Pb^{2+}$ concentration of 31.5 ppb (±1.4).

Another embodiment of the present disclosure provides a $Pb^{2+}$ sensor for $Pb^{2+}$ ions in a sample. According to this embodiment, the $Pb^{2+}$ sensor comprises a matrix material and a fluorophore represented in its protected form by Formula IV, as described in detail herein with reference to the fluorescent binder, wherein the fluorophore is dissolved in, embedded in, affixed in, absorbed in, or suspended in the matrix material and forms a fluorescent complex when bound in its unprotected form (represented by Formula V) to $Pb^{2+}$. As used in these embodiments, the terms "fluorescent binder" and "fluorophore" refer to a compound having a structure represented by Formula IV (in the fluorophore's protected form) or Formula V. According to specific embodiments, the $Pb^{2+}$ sensor is selective for $Pb^{2+}$ over other metal ions, such as, but not limited to metal ions selected from $Li^+$, $Na^+$, $K^+$, $Ca^{2+}$, $Mg^{2+}$, $Fe^{2+}$, $Co^{2+}$, $Ni^{2+}$, $Cu^{2+}$, $Zn^{2+}$, $Cd^{2+}$, $Mn^{2+}$, $Hg^{2+}$, $Sn^{2+}$, $As^{3+}$, and mixtures thereof. In addition, the $Pb^{2+}$/fluorophore complex may have a greater fluorescence emission intensity compared to the fluorescence emission intensity of complexes between the fluorophore in other metal ions.

The fluorescence emission intensity of the $Pb^{2+}$/complex in a sample may be measured and compared to a standard calibration plot or values to determine the $Pb^{2+}$ ion concentration in the sample. For example, To further examine the sensitivity and accuracy of the sensor, a NIST standard of trace elements in water (SRM® 1643e) in the concentration range of 1-50 ppb $Pb^{2+}$ was used and probed with 1 μM of a compound having the structure of Formula IV. In this case, accurate fluorescence responses were observed from 50 ppb to as low as 10 ppb. Further, compound IV was also used in quantitating the concentration of $Pb^{2+}$ in solutions prepared from a lead standard (NIST SRM® 3128). These results were compared with those obtained from inductively coupled plasma mass spectrometry ("ICPMS") measurement. The two methods were found to be comparable by F-test and t-test analyses.

The matrix material may be any material suitable for dissolving, embedding, affixing, absorbing, or suspending the fluorophore that can be used to test a sample composition for $Pb^{2+}$ ion concentration. For example, the matrix material may be, but is not limited to, a material selected from the group consisting of an aqueous solvent, a gel, a sol-gel material, a solvent, a paper, a polymer, a nanoparticle, a solid state material, and a surface modified material. One having ordinary skill in the art will recognize that other matrix materials may be used without departing from the intent of the invention as described herein.

In one embodiment, a $Pb^{2+}$ sensor may be immobilized in the form of a gel. For example, according to one embodiment, the gel may be prepared using sol-gel technology from an appropriate starting material. It may be important to have a matrix material with minimal absorption in the regions in which the fluorophore or the $Pb^{2+}$/fluorophore complex absorb or emit light. Suitable materials for gels may include gels based on silicon and aluminum. Such gels may be produced in numerous ways and methods of preparation of such gels are known in the art. For example, hydrolysis of silicon-alkoxide in the presence of an alcohol would produce a suitable gel material. Common precursors for preparing silica based gels include, but are not limited to, tetramethoxysilane ($Si(OCH_3)_4$) and tetraethoxysilane ($Si(OC_2H_5)_4$) and the corresponding alcohols. In addition, various silica based gel materials are commercially available with particle sizes ranging from 10 nm to 40 nm and are known to those of ordinary skill in the art. In certain embodiments, the fluorophore may be doped into the gel to produce $Pb^{2+}$ sensors of the present disclosure. Gel materials may also be made having differentially shaped and sized particles, which may be doped with the fluorophore to provide versatile devices. One critical component of the functioning of the gel may be the response time, which can, at least in part, be controlled by manipulating the porosity of the gel. The porosity of the gel may be controlled, for example, by the method of gel preparation using methods reported in the literature and known to those of ordinary skill. According to one embodiment, the gel may be engineered to have functionality which may be reactive with a functionalized fluorophore and thus can chemically or physically link the fluorophore to the structure of the gel. For example, the functionalized fluorophore may be polymerized with the gel and thus, incorporated into the structure of the gel.

Another embodiment may include a lead sensing paper, analogous to a pH paper. According to this embodiment, a known concentration of fluorophore may be impregnated into a porous paper. The fluorophore impregnated paper may then be contacted with a composition comprising $Pb^{2+}$ ions and the paper would fluoresce with an emission intensity, as determined by a fluorophoric device, that may correspond to the $Pb^{2+}$ ion concentration in the composition.

In those embodiments where the fluorophore may be linked to the structure of the matrix material, one or more of the hydrogens on the fluorophore may be replaced with a group reactive with a functionality in the matrix material. For example, as discussed herein, one or more hydrogens on the fluorophore as represented in its protected form by Formula IV may be replaced by the group -L-$R^y$ (as described herein) and the group $R^y$ may be reacted with a functionality in the matrix material such that a bond, for example a covalent bond, an ionic bond, or other non-covalent interaction (such as a hydrogen bond or a hydrophobic interaction) is formed between the fluorophore and the matrix material. In these embodiments, the fluorophore is linked to, bonded to, or otherwise attached to the matrix material.

In specific embodiments of the $Pb^{2+}$ sensor, the sensor may further comprise a device capable of measuring an intensity of a fluorescence emission spectrum. According to these embodiments, the device may be used to measure the fluorescence emission spectrum of the $Pb^{2+}$/fluorophore complex in the matrix material. Examples of devices include, but are not limited to, fluorophoric devices and spectrometers, such as fluorescence spectrometers or fluorometers, laser fluorescence spectrometers, and the like. The fluorescence emission spectrum may be compared to emissions of known standards, for example a calibration plot, to determine the concentration of $Pb^{2+}$ in the sample. For certain embodiments, the determination of the $Pb^{2+}$ may be automated, such as by use of a computer, sampler, or other electronic device. For example, the computer or other electronic device may compare the fluorescence emission spectrum with the spectra of standards and determine the $Pb^{2+}$ ion concentration in the sample. In other embodiments, the sample and standard spectra may be compared by a user of the sensor and a $Pb^{2+}$ ion concentration of the sample may be determined based on the emission intensity of the $Pb^{2+}$/complex.

Further embodiments of the present disclosure provide methods for detecting $Pb^{2+}$ ion concentrations, for example the Pb$^{2+}$ ion concentration in a sample. According to one embodiment, the methods may comprise contacting a Pb sensor comprising a fluorophore represented in its protected form by Formula IV, as described in detail herein with reference to the fluorescent binder, with a composition, wherein at least a portion (and in certain embodiments all or substantially all) of the Pb$^{2+}$ ions in the composition binds with the fluorophore in its unprotected form (represented by Formula V) to form a complex; and measuring a fluorescence emission intensity of the complex. As used herein, the term "substantially all" when used in reference to metal ion binding means an amount of metal ions equivalent to the concentration of the metal ion/binder complex as determined by the equilibrium expression for the reaction/complexation of the metal ion with the fluorophore. As described herein, the complex may have a fluorescence emission intensity that is greater than the fluorescence emission intensity of a complex formed from the fluorophore binding with another metal, such as, but not limited to, the other metals described herein. In specific embodiments, the method may be used to selectively detect Pb$^{2+}$ ions in the composition in the presence of other metal ions.

In certain embodiments, the method may further comprise irradiating the complex with electromagnetic radiation having a wavelength(s) equal to the excitation wavelength or band of the Pb$^{2+}$/fluorophore complex, as described herein. In specific embodiments, the method may further comprise quantifying the lead ion concentration by calculating a concentration of Pb$^{2+}$ ions in the composition based on the fluorescence emission intensity of the Pb$^{2+}$/fluorophore complex. For example, the fluorescence emission intensity, as determined by the fluorescence emission spectrum, may be compared to a standard fluorescence emission calibration plot for the Pb$^{2+}$/fluorophore complex to determine the Pb$^{2+}$ ion concentration in the composition.

According to specific embodiments, the composition being tested for the presence of Pb$^{2+}$ ions by these methods may be an aqueous composition. For example, suitable aqueous compositions of which the Pb$^{2+}$ ion concentrations may be determined include, but are not limited to, a drinking water sample, a ground water sample, a sample from a body of water (including an ocean, lake, river, stream, pond, and the like), an environmental sample, a biological fluid sample, an air sample, or an aqueous extraction (including but not limited to paint chip extractions, soil extractions, and food sample extractions). Other aqueous extractions may also be tested for Pb$^{2+}$ ion concentration and are within the scope of the present invention. In other embodiments, the composition being tested by these methods for the presence of Pb$^{2+}$ ions may be a non-aqueous composition, such as a neat liquid or a solution or suspension, such as where the sample to be tested is extracted, suspended, or dissolved in a suitable solvent including an organic or inorganic solvent. In specific embodiments, the organic or inorganic solvent may be a solvent in which Pb$^{2+}$ ions are at least partially soluble.

According to specific embodiments of the methods herein, the Pb$^{2+}$ sensor may further comprise a matrix material, such as the matrix materials described in detail herein, wherein the fluorophore may be dissolved in, embedded in, affixed in, absorbed in, or suspended in the matrix material. As discussed herein, the fluorophore may be modified by replacing one or more hydrogens on the fluorophore with a group reactive with a functionality in the matrix material. According to specific embodiments, the fluorophore may be linked to or otherwise attached to the matrix material.

While various specific embodiments have been described in detail herein, the present disclosure is intended to cover various different combinations of the disclosed embodiments and is not limited to those specific embodiments described herein. Various embodiments of the present disclosure will be better understood when read in conjunction with the following non-limiting Examples. The procedures set forth in the Examples below are not intended to be limiting herein, as those skilled in the art will appreciate that various modifications to the procedures set forth in the Examples, as well as to other procedures not described in the Examples, may be useful in practicing the invention as described herein and set forth in the appended claims.

EXAMPLES

Example 1

3-Methyl-3-tetrahydropyranyloxy-butyne (compound 1) and 4-phenyl-1,3-dithiolane-thione were prepared according to P. G. Baraldi, et al., *Tetrahedron*, 1989, 45, 1517-1532 and C. C. J. Culvenor, et al., *J. Chem. Soc.*, 1946, 1050, the disclosures of each of which are incorporated in their entirety by reference herein. All reactions were conducted under an atmosphere of argon unless otherwise indicated. $CH_2Cl_2$ was distilled over $CaH_2$, $Et_2O$ over Na wire/benzophenone and methanol over Mg. All the other reagents and solvents were used without further purification. Column chromatography was performed on Silica gel 65×250 mesh (Sorbent Technologies).

$^1$H NMR and $^{13}$C NMR spectra were recorded at 500 and 125 MHz respectively, on a Varian Unity plus spectrometer. Proton peak positions were referenced to tetramethylsilane (TMS, set at $\delta$=0.00) in $CDCl_3$ and to the peak of residual non-deuterated solvent set at $\delta$=3.31 in $CD_3OD$. Carbon peak positions were referenced to the central peak of the solvent set at $\delta$=77.0 in $CDCl_3$, $\delta$=49.0 in $CD_3OD$. Infrared spectra were recorded on a Nicolet 380 FT-IR (Thermo) spectrometer. UV-vis spectra were obtained on a Perkin-Elmer Cary 300 spectrometer and on an Olis Cary-14 spectrophotometer in quartz cells (path length 10 mm). APCI mass spectra were recorded in methanol on a Waters ZMD mass spectrometer set in positive mode (solvent: methanol; cone voltage: 20 V; corona 2.7 kV; source temperature: 130 C; flow rate 100 μL/min) or negative mode (solvent: methanol; cone voltage: −20 V; corona 2.5 kV; source temperature: 130° C.; flow rate 100 μL/min). ESI-MS were recorded on a Waters ZMD mass spectrometer set in the negative ionization mode (solvent: methanol; cone voltage: 20 V; capillary voltage: 2.9 kV; source temperature: 130° C.; flow rate 150 μL/min). X-ray data collections were carried out on a Bruker Smart Apex II diffractometer, equipped with graphite-monochromator and Mo—Kα radiation (λ=0.71073 Å). Microwave reaction were performed under solvent-free conditions in the presence of the catalyst montmorillonite KSF) in a STAR System 2 (CEM Corporation) single mode microwave reactor. Inductively coupled plasma mass spectrometry was conducted in an Agilent 7500ce equipped with a Shield Torch SYSTEM.

Synthesis of Compound 2.

n-Butyl lithium (18 mL, of a 1.6 M solution in hexane, 28 mmol) was added to a solution of 3-methyl-3-tetrahydropyranyloxy-butyne (3.3 g, 19 mmol) in $Et_2O$, previously cooled at 0° C. The resulting solution was stirred for 30 min at 0° C., then cooled to −78° C. and diethyl oxalate (4.3 mL, 29.4 mmol) was added. The reaction was followed by TLC (hexane/AcOEt 90:10). After ca. 2 h the reaction mixture was poured in a cold aqueous solution of $NH_4Cl$. The aqueous layer was extracted with of $Et_2O$ (3 25 mL). The organics were dried over $MgSO_4$, the solvent was removed under reduced pressure and the resulting pale yellow oil was purified by chromatography (silica gel, hexane/AcOEt 90:10) to give ethyl 5-methyl-2-oxo-5-(tetrahydro-2H-pyran-2-yloxy) hex-3-ynoate (2) as a pale yellow liquid. Yield: 2.04 g (40%). $^1$H-NMR spectrum in CDCl$_3$ (ppm): 5.10 (m, 1H), 4.38 (q, 2H), 4.36 (m, 2H), 3.96 (m, 2H), 3.54 (m, 2H), 1.85 (m, 2H), 1.75 (m, 2H), 1.64 (s, 3H), 1.59 (s, 3H), 1.40 (t, 3H). $^{13}$C-NMR spectrum in CDCl$_3$ (ppm): 169.3, 158.7, 101.4, 96.2, 81.6, 70.5, 63.1, 31.5, 29.2, 28.9, 25.2, 19.9, 13.8, 13.8. Selected IR (neat, cm$^{-1}$): 2209, 1741, 1689. MS-APCI calculated for C$_{14}$H$_{20}$O$_5$ [M]$^-$ 268.13; found 267.96.

Synthesis of Compound 4.

Ethyl 5-methyl-2-oxo-5-(tetrahydro-2H-pyran-2-yloxy) hex-3-ynoate (2) (1.0 g, 3.7 mmol) and 4-phenyl-1,3-dithiolane-thione (2.0 g, 9.3 mmol) were dissolved in xylene (15 mL). The deep yellow solution was heated to 130° C. for ca. 4 h under Ar (the reaction was followed by TLC, eluent: CH$_2$Cl$_2$). The solvent was removed under reduced pressure and purification of the residue by chromatography (silica gel, CH$_2$Cl$_2$) provided 4,4-dimethyl-2-thioxo-4H-[1,3]dithiolo [4,5-c]pyran-6,7-dione (4) as a yellow solid. Yield: 0.44 g (48%). $^1$H-NMR spectrum in CDCl$_3$ (ppm): 1.88 (s, 6H). $^{13}$C-NMR spectrum in CDCl$_3$ (ppm): 205.3, 167.7, 162.6, 157.8, 153.6, 83.2, 31.9. Selected IR (neat, cm$^{-1}$): 1747, 1681, 1557, 1460. MS-ESI calculated for C$_7$H$_8$O$_4$S$_2$Na [M+Na]$^+$ 268.96; found 268.79.

Synthesis of Compound 5.

Mercury acetate (181 mg, 0.568 mmol) was added to a stirred solution of 4,4-dimethyl-2-thioxo-4H-[1,3]dithiolo[4,5-c]pyran-6,7-dione (4) (100 mg, 0.406 mmol) in CH$_2$Cl$_2$/AcOH (3:1). The reaction was followed by TLC (silica, CH$_2$Cl$_2$) and after ca. 30 min the mixture is filtered through a celite pad to remove the mercury salts. The resulting solution was washed first with water (3×15 mL) and then with sat. aqueous NaHCO$_3$ (5×10 mL), and dried over MgSO$_4$. Removal of the solvent under reduced pressure afforded pure 4,4-dimethyl-4H-[1,3]dithiolo[4,5-c]pyran-2,6,7-trione (5) a pale beige solid. Yield: 65 mg (70%). $^1$H-NMR spectrum in CDCl$_3$ (ppm): 1.88 (s, 6H). $^{13}$C-NMR spectrum in CDCl$_3$ (ppm): 184.5, 163.5, 160.4, 153.5, 128.3 84.2, 31.8. Selected IR (neat, cm$^{-1}$): 1746, 1693, 1641, 1552, 1453. MS-ESI calculated for C$_7$H$_8$O$_4$S$_2$ [M+H]$^+$230.98; found 230.78; calculated for C$_7$H$_8$O$_4$S$_2$Na [M+Na]$^+$) 252.96; found 252.79.

Synthesis of Compound 6.

o-Phenylenediamine (50 mg, 0.22 mmol) was added to a stirred solution of 4,4-dimethyl-4H-[1,3]dithiolo[4,5-c]pyran-2,6,7-trione (5) (100 mg, 0.43 mmol) in methanol (15 mL). The solution was stirred overnight then the solvent was removed under reduced pressure and the residue was purified by crystallization from CHCl$_3$/hexane yielding pure 3-(5-(2-hydroxypropan-2-yl)-2-oxo-1,3-dithiol-4-yl)quinoxalin-2 (1H)-one (6) as a light orange solid. Yield: 124.5 mg (91%). $^1$H-NMR spectrum in CDCl$_3$ (Ppm): 10.40 (bs, 1H), 7.88 (d, 1H), 7.62 (t, 1H), 7.43 (d, 1H), 7.28 (t, 1H), 4.28 (s, 1H), 1.61 (s, 6H). $^1$H-NMR spectrum in CD$_3$OD (ppm): 7.82 (d, 1H), 7.60 (t, 1H), 7.39 (d, 1H), 7.36 (t, 1H), 1.52 (s, 6H). $^{13}$C-NMR spectrum in CD$_3$OD (ppm): 194.6; 158.7; 156.0; 148.2; 136.0; 132.6; 127.9; 125.5; 123.6; 122.3; 119.2; 77.3; 33.8. Selected IR (neat, cm$^{-1}$): 1667, 1598. MS-ESI calculated for C$_{14}$H$_{11}$N$_2$O$_3$S$_2$ [M–H]–319.03; found 318.87. UV-vis in acetonitrile ($\lambda_{max}$, nm ($\epsilon$, M$^{-1}$ cm$^{-1}$)): 230 (19187), 283 (9295), 356 (21820).

Synthesis of Compound 7.

Method 1: 4,4-Dimethyl-4H-[1,3]dithiolo[4,5-c]pyran-2,6,7-trione (5) (80 mg, 0.347 mmol), o-phenylenediamine (40 mg, 0.347 mmol) and trifluoroacetic acid (70 µL) were mixed in a mortar until a homogeneous solid was obtained. The solid was heated to 70° C. in a vacuum oven for 18 h. The crude was purified by chromatography (silica gel, CH$_2$Cl$_2$). The first fraction collected was pure 4,4-dimethyl-4H-5-oxa-1,3-dithia-6,11-diaza-cyclopenta[a]anthracen-2-one (7). Yield: 15 mg (14%). A second fraction was collected from the column using a mixture of CH$_2$Cl$_2$ and methanol (98:2) as solvent, which was identified as 3-(5-(2-hydroxypropan-2-yl)-2-oxo-1,3-dithiol-4-yl)quinoxalin-2(1H)-one (6). Yield: 25 mg (22%). $^1$H-NMR spectrum in CDCl$_3$ (ppm): 7.96 (d, 1H), 7.83 (d, 1H), 7.66 (t, 1H), 7.60 (t, 1H), 1.84 (s, 6H, Me). $^{13}$C-NMR spectrum in CDCl$_3$ (ppm): 189.0; 152.5; 141.0; 140.7; 139.6; 133.7; 130.5; 128.6; 128.1; 127.5; 124.2; 81.2; 30.0. Selected IR (neat, cm$^{-1}$): 1705, 1664, 1624, 1461, 1409. MS-APCI calculated for C$_{14}$H$_{11}$N$_2$O$_2$S$_2$ [M+H]+303.02; found 302.93. UV-vis in acetonitrile ($\lambda_{max}$, nm ($\epsilon$, M$^{-1}$ cm$^{-1}$)): 208 (19187), 255 (8543), 365 (10418), 383 (10244). UV-vis in methanol ($\lambda_{max}$, nm ($\epsilon$, M$^{-1}$ cm$^{-1}$)): 256 (10988), 367 (11194), 385 (9568).

Method 2: 4,4-Dimethyl-4H-[1,3]dithiolo[4,5-c]pyran-2,6,7-trione (5) (150 mg, 0.65 mmol), o-phenylenediamine (75 mg, 0.65 mmol) and montmorillonite KSF (100 mg) were mixed in a mortar until a homogeneous solid was obtained then the solid mixture was transferred into a test tube and irradiated with microwaves for 4 min. The resulting mixture was purified by chromatography (silica gel, CH$_2$Cl$_2$) to give pure 4,4-dimethyl-4H-5-oxa-1,3-dithia-6,11-diaza-cyclopenta[a]anthracen-2-one (7). Yield: 90 mg (45%).

Method 3: 3-(5-(2-Hydroxypropan-2-yl)-2-oxo-1,3-dithiol-4-yl)quinoxalin-2(1H)-one (6) (130 mg, 0.405 mmol) was partially dissolved in CH$_2$Cl$_2$ (10 mL). Benzylchloroformate (125 µL, 0.81 mmol) and triethylamine (120 µL) were added and the resulting yellow solution was stirred overnight. The volume of the solution was reduced to ca. 3 mL and it was purified by chromatography (silica gel, CH$_2$Cl$_2$) to give pure 4,4-dimethyl-4H-5-oxa-1,3-dithia-6,1,1-diaza-cyclopenta [a]anthracen-2-one (7). Yield: 82 mg (70%).

Example 2

Determination of Stoichiometry of Pb/Ligand Complex: In this Example, the relative intensity of the fluorescence emission of the Pb$^{2+}$/Ligand was determined at varying mole fraction of ligand.

A solution of ligand 4,4-dimethyl-4H-5-oxa-1,3-dithia-6, 11-diaza-cyclopenta[a]anthracen-2-one (7) in 2.5% methanol in water containing a 1:2 ratio of ligand to Et$_4$NOH was titrated with a solution of the metal salt (lead acetate) in 2.5% methanol in water. The mole fraction of the ligand in the solution was varied. The mixture of metal and ligand was incubated for an hour after addition to ensure complex formation and then the fluorescence emission spectrum intensity was measured and plotted against the mole fraction of ligand. The plot of the emission intensity vs. mole fraction of fluorophore is presented in FIG. 12. The maximum fluorescence emission intensity was observed at a mole fraction of 0.5 indicating a 1:1 complex. In addition, the intensity of the fluorescence was greater for the complex than for the uncomplexed ligand. Thus indicating that binding of the metal to the ligand could act as a sensor, showing the presence of Pb$^{2+}$ ion in solution.

Example 3

In this Example, the "turn on" response of the fluorophore corresponding to Formula V (Formula IV in protected form) was determined. The fluorescence emission spectrum of a 5 µM solution of the fluorophore in 2.5% methanol-water was recorded with a maximum emission intensity observed at $\lambda_{max}$=465 nm (expanded spectrum shown in the inset in FIG. 49). In parallel, a solution of 5 µM of the fluorophore and base (10 µM, Et$_4$NOH) in 2.5% methanol-water was prepared and a solution of lead acetate was added to it such that the final total Pb$^{2+}$ ion concentration in the solution was 75 µM. The fluorescence emission spectrum of the resulting Pb$^{2+}$/fluorophore complex was recorded with a maximum fluorescence emission intensity observed at $\lambda_{max}$=423 nm as presented in FIG. 49. The fluorescence emission of the Pb$^{2+}$/fluorophore complex was significantly greater than the free fluorophore demonstrating that the fluorophore can act as a fluorescent detector for Pb$^{2+}$.

Example 4

In this Example, the effect of pH on the fluorescence emission intensity of the Pb$^{2+}$/fluorophore complex was determined using the fluorophore corresponding to Formula V (Formula IV in protected form). Eleven solutions of 10 µM fluorophore were prepared in 2.5% methanol-water. The solutions also contained Et$_4$NOH in 2:1 mole ratio (base: fluorophore). To each of the solutions, lead acetate was added such that each solution had a final concentration of 5 µM of Pb$^{2+}$ ion and the solutions were incubated in the dark for one hour. The pH of each of the solutions was recorded to be 10. The pH's of these solutions were individually adjusted for pH ranging between 12.7 to 1.6 either by the addition of Et$_4$NOH (for alkaline pH) or acetic acid (acidic solutions). The fluorescence emission of each of the solutions with adjusted pH were measured, recorded, and plotted against pH as measured for the solution. The data plot is presented in FIG. 50. The Pb$^{2+}$/fluorophore complex displayed a high fluorescence emission intensity over a broad pH range.

Example 5

In this Example, the fluorescence emission of the Pb$^{2+}$/fluorophore complex was compared to the fluorescence emission of metal ion/fluorophore complexes of certain other metal ions. The fluorophore used in this example was the fluorophore corresponding to Formula V (Formula IV in protected form). Stock solutions of each metal ion were made such that the final metal ion concentration (of total volume 3 mL) of the solution is either 75 µM or 2 millimolar. Metal ions examined in this Example were Li$^+$, Na$^+$, K$^+$, Ca$^{2+}$, Mg$^{2+}$, Fe$^{2+}$, Co$^{2+}$, Ni$^{2+}$, Cu$^{2+}$, Zn$^{2+}$, Cd$^{2+}$, Mn$^{2+}$, Hg$^{2+}$, and As$^{3+}$ ions. To each solution was added the requisite amount of a fluorophore solution (in 2.5% methanol-water) containing base (Et$_4$NOH) in 1:2 molar ratio of fluorophore to base such that the concentration of the fluorophore in each solution was 5 µM. The solutions were incubated for 1 hour in the dark. The UV-visible and fluorescence spectra of each solution were recorded. In parallel, another set of solutions were prepared with the same concentration of metal ion, fluorophore, and base, but this time in addition to the other metal ion and the fluorophore, each solution had 75 µM of lead ion (Pb$^{2+}$ from lead acetate) in it. These solutions were incubated in the dark for an hour, their UV-visible and fluorescence spectra were recorded. The results are shown in FIG. 51 (black bar showing fluorescence emission intensity of the metal ion/fluorophore solution, grey bar showing the fluorescence emission intensity of the metal ion/Pb$^{2+}$/fluorophore solution). As shown in FIG. 51, each solution containing Pb$^{2+}$ in addition to the metal ion displayed a significantly greater fluorescence emission intensity compared to the corresponding metal ion/fluorophore solution without Pb$^{2+}$.

Example 6

In this example, a standard curve showing Pb$^{2+}$ concentration versus fluorescence intensity of the Pb$^{2+}$/fluorophore complex was prepared using the fluorophore corresponding to Formula V (Formula IV in protected form) and used to determine the Pb$^{2+}$ ion concentration in water samples.

A standard curve for fluorescence intensity as a function of Pb$^{2+}$ ion concentration was first created. Thirteen solutions of the fluorophore at 10 µM concentration containing base (Et$_4$NOH) were prepared in 2.5% methanol-water. To twelve of these solutions, a solution of lead acetate was added such that the final concentration of Pb$^{2+}$ in the solutions varied from 1 ppb to 50 ppb. The final volume in each solution was 10 mL. The solutions were incubated in the dark for one hour and the fluorescence spectra were measured. The solution containing no added lead was considered baseline and fluorescence intensity of that solution was subtracted from the fluorescence intensity of all other solutions. The fluorescence emission intensity was plotted as a function of concentration of lead (Pb$^{2+}$) to give a linear plot: Em. Int.=305 (±17)×[Pb$^{2+}$]+809 (±486). The $R^2$ of this linear regression analysis was 0.985.

Next, a river water sample and three local domestic water samples were collected in clean screw cap plastic vials. Five 10 mL sample solutions containing a water sample or a standard sample; and the fluorophore and base (Et$_4$NOH) were made by taking 1 mL of a stock solution of the fluorophore/base in 2.5% methanol-water and 9 ml of the water sample or standard to be tested. Each water sample solution was incubated for an hour and the fluorescence spectra of the solutions were measured. The fluorescence emission intensity of the standard sample was subtracted from the fluorescence emission intensity of each of the water samples. The resulting fluorescence intensity was compared to the standard curve to calculate the concentration of lead in solution. The river water sample showed a Pb$^{2+}$ concentration of 41.5 (±3.4) ppb and the three domestic water samples showed Pb$^{2+}$ concentrations of 30.5 (±2.7) ppb, 11.6 (±1.4) ppb, and 31.5 (±1.4) ppb. Spectroscopic Materials and Methods.

All spectroscopic measurements were recorded in a solution of 2.5% methanol (for solubility reason) and water. HPLC grade MeOH and distilled water were used for each measurement. Absorption spectra were measured on a Varian Cary 300 spectrometer. Samples for absorption measurement were performed in 1-cm 1-cm quartz cuvettes (3.5 mL volume, Starna). Fluorescence spectra were measured on a Photon Technology International QuantaMaster™4 spectrofluorometer. Fluorescence measurements were performed in 1-cm 1-cm quartz cuvettes (3.5 mL volume, NSG Precision Cells). Fluorescence quantum yields were determined in reference to fluorescein in 0.1 NaOH ($\phi$=0.95). The binding ratio was determined using Job's method of continuous variation. The binding affinity of Pb$^{2+}$ to compound IV was also found. Excitation was provided at 389 nm. The dissociation constant, $K_d$, was determined by using the Hill1 function in OriginPro 8, which is as follows: y=START+(END−START) $x^n$/($k^n$+$x^n$). START is the first data point where the curve begins, END is the last data point where the curve ends, x is the concentration of Pb$^{2+}$, k is the $K_d$ for the binding reaction, and n is the Hill coefficient or the cooperativity of the dependence on x. A 10 μM solution (1:2:4 $Pb^{2+}$:compound IV:$NEt_4OH$) was pH adjusted down by adding AcOH and adjusted up by adding $NEt_4OH$. SRM® 1643e Trace Elements in Water (1-50 ppb $Pb^{2+}$) was probed with 1 μM compound IV in $NEt_4OH$ (2:1 $NEt_4OH$:compound IV) and 2.5% MeOH and water. Compound IV was able to detect $Pb^{2+}$ quantitatively by an increase in fluorescence response from 10-50 ppb $Pb^{2+}$. For ICPMS measurements, solutions were scanned for $^{204}Pb$, $^{206}Pb$, $^{207}Pb$, $^{208}Pb$ isotopes, the sums of the counts for all isotopes were used for analyses. For quantitative analyses, (ICPMS and fluorescence) calibration curves at pH ~6.6 were created using a multi-element (3.1 elements) calibration standard (ICP-MSCS-M) obtained from High Purity Standards, Charleston, S.C. In both cases, linearity with >99% correlation was maintained with $Pb^{2+}$ concentration in the range 1-50 ppm. Using the linear equations, concentrations of $Pb^{2+}$ present in samples prepared from lead standard solution (SRM® 3128) via serial dilution were determined. The results from two methods (ICPMS and fluorescence) passed the F-test with 95% confidence limit. The t-test with 95% confidence interval showed the results of the methods are statistically equivalent.

Although the invention has been described in detail in the foregoing embodiment for the purpose of illustration, it is to be understood that such detail is solely for that purpose and that variations can be made therein by those skilled in the art without departing from the spirit and scope of the invention.

We claim:

1. A fluorescent binder for $Pb^{2+}$ ions represented in its protected form by Formula IV:

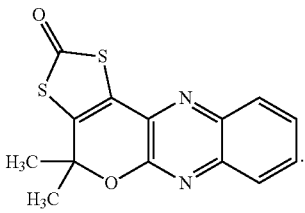

IV

2. The fluorescent binder of claim 1, wherein the binder has a sensitivity for $Pb^{2+}$ with a $K_d$ of less than 500 nM.

3. The fluorescent binder of claim 1, wherein the $Pb^{2+}$ and the fluorescent binder form a $Pb^{2+}$/binder complex.

4. The fluorescent binder of claim 3, wherein the $Pb^{2+}$/binder complex has an excitation band centered around 389 nm and a fluorescence emission band centered around 423 nm.

5. The fluorescent binder of claim 3, wherein the $Pb^{2+}$/binder complex fluoresces with a high fluorescence emission intensity at a pH value of 10 or less.

6. The fluorescent binder of claim 3, wherein the binder selectively binds to $Pb^{2+}$ over other metal ions.

7. The fluorescent binder of claim 6, wherein the other metal ions are selected from the group consisting of $Li^+$, $Na^+$, $K^+$, $Ca^{2+}$, $Mg^{2+}$, $Fe^{2+}$, $Co^{2+}$, $Ni^{2+}$, $Cu^{2+}$, $Zn^{2+}$, $Cd^{2+}$, $Mn^{2+}$, $Hg^{2+}$, $As^{3+}$, and mixtures thereof.

8. The fluorescent binder of claim 3, wherein the fluorescence emission intensity of the $Pb^{2+}$/binder complex is greater than a fluorescence emission intensity of other metal/binder complexes.

9. A $Pb^{2+}$ sensor comprising:
a matrix material; and
a fluorophore represented in its protected form by Formula IV:

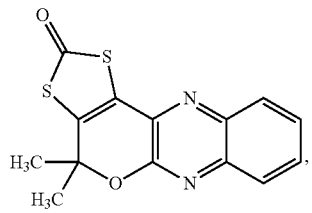

IV wherein the fluorophore is dissolved in, embedded in, affixed in, absorbed in, or suspended in the matrix material and forms a fluorescent complex when bound in its unprotected form to $Pb^{2+}$.

10. The $Pb^{2+}$ sensor of claim 9, wherein the matrix comprises a material selected from the group consisting of an aqueous solvent, a gel, a sol-gel material, a solvent, a paper, a polymer, a nanoparticle, a solid state material, and a surface modified material.

11. The $Pb^{2+}$ sensor of claim 9, further comprising a device capable of measuring an intensity of a fluorescence emission spectrum.

12. The $Pb^{2+}$ sensor of claim 9, wherein one or more of the hydrogens on the fluorophore is replaced with a group reactive with a functionality in the matrix material.

13. A method of detecting $Pb^{2+}$ comprising:
contacting a $Pb^{2+}$ sensor comprising a fluorophore represented in its protected form by Formula IV:

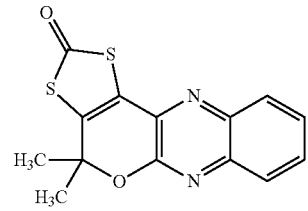

IV with a composition, wherein $Pb^{2+}$ in the composition binds with the fluorophore in its unprotected form to form a complex; and
measuring a fluorescence emission intensity of the complex.

14. The method of claim 13, wherein the method selectively detects $Pb^{2+}$ in the presence of other metal ions.

15. The method of claim 14, wherein the fluorescence emission intensity of the complex formed with $Pb^{2+}$ is greater than the fluorescence emission intensity of a complex formed from the fluorophore binding with another metal.

16. The method of claim 13, further comprising:
calculating a concentration of $Pb^{2+}$ ions in the composition based on the fluorescence emission intensity of the complex.

17. The method of claim 13, wherein the composition is an aqueous composition.

18. The method of claim 17, wherein the aqueous composition is selected from a drinking water sample, a ground water sample, a sample from a body of water, a paint chip extraction, an environmental sample, a soil extraction, a biological fluid sample, a food sample extraction, and an air sample.

19. The method of claim 13, wherein the $Pb^{2+}$ sensor further comprises a matrix material selected from the group consisting of an aqueous solvent, a gel, a sol-gel material, a solvent, a paper, a polymer, a nanoparticle, a solid state material, and a surface modified material, and the fluorophore is dissolved in, embedded in, affixed in, absorbed in, or suspended in the matrix material.

* * * * *